US012582710B2

(12) United States Patent
Ruan et al.

(10) Patent No.: US 12,582,710 B2
(45) Date of Patent: Mar. 24, 2026

(54) SINGLE-CHAIN CORONAVIRUS VIRAL MEMBRANE PROTEIN COMPLEXES

(71) Applicant: University of Houston System, Houston, TX (US)

(72) Inventors: Ke-He Ruan, Bellaire, TX (US); Xinli Liu, Sugar Land, TX (US); Renzhong Lu, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 609 days.

(21) Appl. No.: 18/023,891

(22) PCT Filed: Aug. 27, 2021

(86) PCT No.: PCT/US2021/047982
§ 371 (c)(1),
(2) Date: Feb. 28, 2023

(87) PCT Pub. No.: WO2022/047176
PCT Pub. Date: Mar. 3, 2022

(65) Prior Publication Data
US 2023/0338511 A1    Oct. 26, 2023

Related U.S. Application Data

(60) Provisional application No. 63/071,681, filed on Aug. 28, 2020.

(51) Int. Cl.

| | |
|---|---|
| *A61K 39/215* | (2006.01) |
| *A61K 9/127* | (2025.01) |
| *A61K 39/00* | (2006.01) |
| *A61K 39/12* | (2006.01) |
| *A61P 31/14* | (2006.01) |
| *C07K 14/005* | (2006.01) |
| *C12N 15/86* | (2006.01) |

(52) U.S. Cl.
CPC ............ *A61K 39/215* (2013.01); *A61K 9/127* (2013.01); *A61P 31/14* (2018.01); *C07K 14/005* (2013.01); *C12N 15/86* (2013.01); *A61K 2039/53* (2013.01); *A61K 2039/55505* (2013.01); *A61K 2039/55572* (2013.01); *A61K 2039/55577* (2013.01); *C12N 2770/20022* (2013.01); *C12N 2770/20034* (2013.01); *C12N 2770/20043* (2013.01); *C12N 2770/20071* (2013.01)

(58) Field of Classification Search
None
See application file for complete search history.

(56) References Cited

U.S. PATENT DOCUMENTS

| | | |
|---|---|---|
| 5,166,320 A | 11/1992 | Wu et al. |
| 6,228,844 B1 | 5/2001 | Wolff et al. |
| 11,382,968 B2 * | 7/2022 | Georges ................. C12N 15/86 |

FOREIGN PATENT DOCUMENTS

| | | |
|---|---|---|
| CN | 111088283 A | 5/2020 |
| CN | 111303254 A | 6/2020 |
| CN | 111533790 A | 8/2020 |
| CN | 111537743 A | 8/2020 |
| EP | 0187702 B1 | 3/1990 |
| WO | 2018115527 A2 | 6/2018 |
| WO | 2020169755 A2 | 8/2020 |

OTHER PUBLICATIONS

Ruan, Ke-He, Hui Deng, and Shui-Ping So., "Engineering of a protein with cyclooxygenase and prostacyclin synthase activities that converts arachidonic acid to prostacyclin," Biochemistry, Nov. 2006, pp. 14003-14011, 45.47.

Brunetti-Pierri, Nicola, and Philip Ng, "Helper-dependent adenoviral vectors for liver-directed gene therapy," Human molecular genetics, Apr. 2011, R7-R13, 20.R1.

International Search Report and Written Opinion for related case PCT/US21/47982, Feb. 16, 2022, 32 pages.

Hoffmann, Markus, Hannah Kleine-Weber, and Stefan Pöhlmann, "A multibasic cleavage site in the spike protein of SARS-CoV-2 is essential for infection of human lung cells," Molecular cell, May 2020, pp. 779-784, 78.4.

Nieto-Torres, Jose L., et al., "Severe acute respiratory syndrome coronavirus envelope protein ion channel activity promotes virus fitness and pathogenesis," PLoS pathogens, May 2014, e1004077, 10.5.

Liu, Qi, et al., "Engineered endothelial progenitor cells that overexpress prostacyclin protect vascular cells," Journal of Cellular Physiology, Jul. 2012, pp. 2907-2916, 227.7.

Vollert, Craig, et al., "Elevated prostacyclin biosynthesis in mice impacts memory and anxiety-like behavior," Behavioural brain research, Jan. 2014, pp. 138-144, 258.

Ling, Qing-Lan, et al., "Creating a mouse model resistant to induced ischemic stroke and cardiovascular damage," Scientific reports, Jan. 2018, 1653, 8.1.

Ruan, Ke-He, Vanessa Cervantes, and Shui-Ping So, "Engineering of a novel hybrid enzyme: an anti-inflammatory drug target with triple catalytic activities directly converting arachidonic acid into the inflammatory prostaglandin E2," Protein Engineering, Design & Selection, Dec. 2009, pp. 733-740, 22.12.

Carrillo, Humberto, and David Lipman, "The multiple sequence alignment problem in biology," SIAM journal on applied mathematics, Oct. 1988, pp. 1073-1082, 48.5.

(Continued)

*Primary Examiner* — Manjunath N Rao
*Assistant Examiner* — Jae W Lee
(74) *Attorney, Agent, or Firm* — Carter, DeLuca & Farrell LLP; George Likourezos

(57) ABSTRACT

Recombinant protein coronavirus antigens and vaccine compositions using the same, include a recombinant protein that is a single-chain (SC) viral membrane protein complex derived from the spike (S), envelop (E) and membrane (M) protein of a coronaviruses such as SARS-CoV-2, the causal agent for COVID-19. Methods for immunization of a subject using the vaccine compositions treats or prevents clinical signs caused by coronaviruses infection.

21 Claims, 14 Drawing Sheets
Specification includes a Sequence Listing.

(56)                References Cited

OTHER PUBLICATIONS

Devereux, John, Paul Haeberli, and Oliver Smithies, "A comprehensive set of sequence analysis programs for the VAX," Nucleic Acids Research, Jan. 1984, pp. 387-395, 12,1.

Altschul, Stephen F., et al., "Gapped Blast and PSI-Blast: a new generation of protein database search programs," Nucleic acids research, Sep. 1997, pp. 3389-3402, 25.17.

Froehler, Brian C., Peter G. Ng, and Mark D. Matteucci, "Synthesis of DNA via deoxynudeoside H-phosphonate intermediates," Nucleic Acids Research, Jul. 1986, pp. 5399-5407, 14.13.

Froehler, Brian C., "Deoxynucleoside H-phosphonate diester intermediates in the synthesis of internucleotide phosphate analogues," Tetrahedron letters, Jan. 1986, pp. 5575-5578, 27.46.

Dower, William J., Jeff F. Miller, and Charles W. Ragsdale, "High efficiency transformation of E. coli by high voltage electroporation," Nucleic Acids Research, May 1988, pp. 6127-6145.

Graham, Frank L., and Alex J. Van Der Eb, "A new technique for the assay of infectivity of human adenovirus 5 DNA," virology, Apr. 1973, pp. 456-467, 52.2.

Tai-Kin Wong, Claude Nicolau, and Peter Hans Hofschneider, "Appearance of ß-lactamase activity in animal cells upon liposome-mediated gene transfer," Gene, Jul. 1980, pp. 87-94, 10.2.

Gopal, T. Venkat, "Gene transfer method for transient gene expression, stable transformation, and cotransformation of suspension cell cultures," Molecular and Cellular Biology, May 1985, pp. 1188-1190, 5.5.

Yang, Ning-Sun, et al., "In vivo and in vitro gene transfer to mammalian somatic cells by particle bombardment," Proceedings of the National Academy of Sciences, Dec. 1990, pp. 9568-9572, 87.24.

Hitzeman, Ronald A., Louise Clarke, and John Carbon, "Isolation and characterization of the yeast 3-phosphoglycerokinase gene (PGK) by an immunological screening technique," Journal of Biological Chemistry, Dec. 1980, pp. 12073-12080, 255.24.

Luchansky, J. B., P. M. Muriana, and T. R. Klaenhammer, "Application of electroporation for transfer of plasmid DNA to lactobacillus, lactococcus, leuconostoc, listeria, pediococcus, bacillus, Staphylococcus, enterococcus and propionibacterium," Molecular microbiology, Sep. 1988, pp. 637-646, 2.5.

Wada, Ken-nosuke, et al., "Codon usage tabulated from the GenBank genetic sequence data," Nucleic acids research, May 1992, pp. 2111-2118, 20. Suppl.

Eagle, Harry, "Amino acid metabolism in mammalian cell cultures," Science, Aug. 1959, pp. 432-437, 130.3373.

Stanners, C. P., G. L. Eliceiri, and H. Green, "Two types of ribosome in mouse-hamster hybrid cells," Nature New Biology, Mar. 1971, pp. 52-54, 230.10.

Iscove, N. N., and F. Melchers, "Complete replacement of serum by albumin, transferrin, and soybean lipid in cultures of lipopolysaccharide-reactive B lymphocytes," The Journal of experimental medicine, Mar. 1978, pp. 923-933, 147.3.

Dulbecco, R., and G. Freeman, "Plaque production by the polyoma virus," Virology, 1959, pp. 396-397, 8.3.

Acsadi, Gyula, et al., "Human dystrophin expression in mdx mice after intramuscular injection of DNA constructs," Nature, Aug. 1991, pp. 815-818, 352.6338.

Wolff, Jon A., et al., "Direct gene transfer into mouse muscle in vivo," Science, Mar. 1990, pp. 1465-1468, 247.4949.

Wu, George Y., and Catherine H. Wu, "Receptor-mediated gene delivery and expression in vivo," Journal of Biological Chemistry, Oct. 1988, pp. 14621-14624, 263.29.

Wilson, James M., et al., "Hepatocyte-directed gene transfer in vivo leads to transient improvement of hypercholesterolemia in low density lipoprotein receptor-deficient rabbits," Journal of Biological Chemistry, Jan. 1992, pp. 963-967, 267.2.

Curiel, David T., et al., "Adenovirus enhancement of transferrin-polylysine-mediated gene delivery," Proceedings of the National Academy of Sciences, Oct. 1991, pp. 8850-8854, 88.19.

Cristiano, Richard J., Louis C. Smith, and SLe Woo, "Hepatic gene therapy: adenovirus enhancement of receptor-mediated gene delivery and expression in primary hepatocytes," Proceedings of the National Academy of Sciences, Mar. 1993, pp. 2122-2126, 90.6.

Stamatatos, Leonidas, et al., "Interactions of cationic lipid vesicles with negatively charged phospholipid vesicles and biological membranes," Biochemistry, May 1988, pp. 3917-3925, 27.11.

Eibl, Hansjörg, and Paul Woolley, "Electrostatic interactions at charged lipid membranes. Hydrogen bonds in lipid membrane surfaces," Biophysical Chemistry, Nov. 1979, pp. 261,271, 10.3-4.

Sokolovska, Anna, Stanley L. Hem, and Harm HogenEsch, "Activation of dendritic cells and induction of CD4+ T cell differentiation by aluminum-containing adjuvants," Vaccine, Jun. 2007, pp. 4575-4585, 25.23.

O'Hagan, Derek T., and Rino Rappuoli, "Novel approaches to vaccine delivery," Pharmaceutical research, Sep. 2004, pp. 1519-1530, 21.

SM Wold, William, and Karoly Toth, "Adenovirus vectors for gene therapy, vaccination and cancer gene therapy," Current gene therapy, Dec. 2013, pp. 421-433, 13.6.

Amanat, Fatima, and Florian Krammer, "SARS-CoV-2 vaccines: status report," Immunity, Apr. 2020, pp. 583-589, 52.4.

Tuchscherr, Lorena PN, et al., "Antibodies to capsular polysaccharide and clumping factor A prevent mastitis and the emergence of unencapsulated and small-colony variants of Staphylococcus aureus in mice," Infection and immunity, Dec. 2008, pp. 5738-5744, 76.12.

Ruan, Ke-He, et al., "Large-scale expression, purification, and characterization of an engineered prostacyclin-synthesizing enzyme with therapeutic potential," Archives of biochemistry and biophysics, Dec. 2008, pp. 41-50, 480.1.

Ruan, Ke-He, et al., "An active triple-catalytic hybrid enzyme engineered by linking cyclo-oxygenase isoform-1 to prostacyclin synthase that can constantly biosynthesize prostacyclin, the vascular protector," The FEBS journal, Dec. 2008, pp. 5820-5829, 275.23.

Ravichandran, Supriya, et al., "Antibody signature induced by SARS-CoV-2 spike protein immunogens in rabbits," Science translational medicine, Jul. 2020, eabc3539, 12.550.

Kishimoto, Takashi Kei, and Roberto A. Maldonado, "Nanoparticles for the induction of antigen-specific immunological tolerance," Frontiers in immunology, Feb. 2018, p. 230, 9.

Johnson, Litty, Albert Duschl, and Martin Himly, "Nanotechnology-based vaccines for allergen-specific immunotherapy: Potentials and challenges of conventional and novel adjuvants under research," Vaccines May 2020, p. 237, 8.2.

Kratzer, Bernhard, et al., "All the small things: How virus-like particles and liposomes modulate allergic immune responses," European Journal of Immunology, Jan. 2020, pp. 17-32, 50.1.

Qhattal, Hussaini Syed Sha, et al., "Hyaluronan polymer length, grafting density, and surface poly (ethylene glycol) coating influence in vivo circulation and tumor targeting of hyaluronan-grafted liposomes," ACS nano, Jun. 2014, pp. 5423-5440, 8.6.

Qhattal, Hussaini Syed Sha, and Xinli Liu, "Characterization of CD44-mediated cancer cell uptake and intracellular distribution of hyaluronan-grafted liposomes," Molecular pharmaceutics, Aug. 2011, pp. 1233-1246, 8.4.

Fofaria, Neel M., et al., "Nanoemulsion formulations for anti-cancer agent piplartine-Characterization, toxicological, pharmacokinetics and efficacy studies," International journal of pharmaceutics, Feb. 2016, pp. 12-22, 498.1-2.

Qhattal, Hussaini Syed Sha, et al., "Nanoemulsions of cancer chemopreventive agent benzyl isothiocyanate display enhanced solubility, dissolution, and permeability," Journal of agricultural and food chemistry, Dec. 2011, pp. 12396-12404, 59.23.

International Preliminary Report on Patentability for application No. PCT/US2021/047982, Feb. 28, 2023, 22 pages.

Ling, Qing-Lan, et al., "The protective effects of up-regulating prostacyclin biosynthesis on neuron survival in hippocampus," Journal of Neuroimmune Pharmacology, Jun. 2020, pp. 292-308 15.

Deng, Yuxiao, et al., "Prostacyclin-producing human mesenchymal cells target H19 lncRNA to augment endogenous progenitor function in hindlimb ischaemia," Nature communications, Apr. 2016, p. 11276, 7.1.

(56) References Cited

OTHER PUBLICATIONS

Zhou, Lei, et al., "Endothelial-like progenitor cells engineered to produce prostacyclin rescue monocrotaline-induced pulmonary arterial hypertension and provide right ventricle benefits," Circulation, Aug. 2013, pp. 982-994, 128.9.

Chen, Nanshan, et al., "Epidemiological and clinical characteristics of 99 cases of 2019 novel coronavirus pneumonia in Wuhan, China: a descriptive study," The lancet, Feb. 2020, pp. 507-513, 395.10223.

Han, Xiaoyu, et al., "Novel coronavirus pneumonia (Covid-19) progression course in 17 discharged patients: comparison of clinical and thin-section CT features during recovery," Clinical infectious diseases: an official publication of the Infectious Diseases Society of America (2020).

Nussbaumer-Streit, Barbara, et al., "Quarantine alone or in combination with other public health measures to control Covid-19: a rapid review," Cochrane Database of Systematic Reviews 9 (2020).

Hui, David S., et al., "The continuing 2019-nCoV epidemic threat of novel coronaviruses to global health—The latest 2019 novel coronavirus outbreak in Wuhan, China," International journal of infectious diseases, Feb. 2020, pp. 264-266, 91.

Press Release, "WHO Director-General's opening remarks at the media briefing on Covid-19," Mar. 11, 2020, 4 pages.

FDA news release: Coronavirus (Covid-19) Update: FDA Takes New Actions to Accelerate Development of Novel Prevention, Treatment Options for Covid-19, May 11, 2020, https://www.fda.gov/news-events/press-announcements/coronavirus-covid-19-update-fda-takes-new-actions-accelerate-development-novel-prevention-treatment, 3 pages.

Knibbs, Kate, "The Promise of Antibody Treatments for Covid-19," Wired, May 22, 2020, https://www.wired.com/story/coronavirus-covid-19-antibody-treatment/, 15 pages.

Smith, Trevor RF, et al., "Immunogenicity of a DNA vaccine candidate for Covid-19," Nature communications, May 2020, p. 2601, 11.1.

Zhu, Feng-Cai, et al., "Safety, tolerability, and immunogenicity of a recombinant adenovirus type-5 vectored Covid-19 vaccine: a dose-escalation, open-label, non-randomised, first-in-human trial," The Lancet, Jun. 2020, pp. 1845-1854, 395.10240.

Amawi, Haneen, et al., "Covid-19 pandemic: an overview of epidemiology, pathogenesis, diagnostics and potential vaccines and therapeutics," Therapeutic delivery, Apr. 2020, pp. 245-268, 11.4.

Uddin, Mohammed, et al., "SARS-CoV-2/Covid-19: viral genomics, epidemiology, vaccines, and therapeutic interventions," Viruses, May 2020, p. 526, 12.5.

Pagliusi, Sonia, et al., "Emerging manufacturers engagements in the Covid-19 vaccine research, development and supply," Vaccine, Jul. 2020, pp. 5418-5423, 38.34.

Hanney, Stephen R., et al., "From Covid-19 research to vaccine application: why might it take 17 months not 17 years and what are the wider lessons?" Health Research Policy and Systems, Dec. 2020, pp. 1-10, 18.1.

Zhang, Lei, and Yunhui Liu, "Potential interventions for novel coronavirus in China: A systematic review," Journal of medical virology, May 2020, pp. 479-490, 92.5.

De Alwis, Ruklanthi, et al., "Impact of immune enhancement on Covid-19 polyclonal hyperimmune globulin therapy and vaccine development," EBioMedicine, May 2020, 7 pages, 55.

Yung-Fang, Tu, et al., "A review of SARS-CoV-2 and the ongoing clinical trials," International Journal of Molecular Sciences, Apr. 2020, p. 2657, 21.7.

Wang, Fuzhou, Richard M. Kream, and George B. Stefano, "An evidence based perspective on mRNA-SARS-CoV-2 vaccine development," Medical science monitor: international medical journal of experimental and clinical research, 26 (2020): e924700-1.

Calina, Daniela, et al., "Towards effective Covid-19 vaccines: Updates, perspectives and challenges," International journal of molecular medicine, Jul. 2020, pp. 3-16, 46.1.

Wu, Fan, et al., "Neutralizing antibody responses to SARS-CoV-2 in a Covid-19 recovered patient cohort and their implications," MedRxiv, Jan. 2020, 20 pages.

Diamond, Michael S., and Theodore C. Pierson, "The challenges of vaccine development against a new virus during a pandemic," Cell Host & Microbe, May 2020, pp. 699-703, 27.5.

Grenfell, Rob, and Trevor Drew, "Here's why it's taking so long to develop a vaccine for the new coronavirus," Science Alert Archived from the original, Feb. 2020, 28.

Anonymous, Clinical trial No. NCT04336410 for "Safety, Tolerability and Immunogenicity of INO-4800 for Covid-19 in Healthy Volunteers" at ClinicalTrials.gov, https://classic.clinicaltrials.gov/ct2/show/study/NCT04336410, Jan. 10, 2024, 8 pages.

Anonymous, Clinical trial No. NCT04412538 for "Safety and Immunogenicity Study of an Inactivated SARS-CoV-2 Vaccine for Preventing Against Covid-19" at ClinicalTrials.gov., https://clinicaltrials.gov/study/NCT04412538id=NCT04412538&rank=1, Jan. 10, 2024, 18 pages.

Anonymous, Clinical trial No. NCT04299724 for "Safety and Immunity of Covid-19 aAPC Vaccine" at ClinicalTrials.gov., https://clinicaltrials.gov/study/NCT04299724?id=NCT04299724&rank=1, Jan. 10, 2024, 10 pages.

Anonymous, Clinical trial No. NCT04276896 for "Immunity and Safety of Covid-19 Synthetic Minigene Vaccine" at ClinicalTrials.gov, https://clinicaltrials.gov/study/NCT04276896?id=NCT04276896&rank=1, Jan. 10, 2024, 10 pages.

Lacaille-Dubois, Marie-Aleth, "Updated insights into the mechanism of action and clinical profile of the immunoadjuvant QS-21: A review," Phytomedicine, Jul. 2019, 152905, 60.

Hirose, T., R. Crea, and K. Itakura. "Rapid synthesis of trideoxyribonucleotide blocks." Tetrahedron Letters 19.28 (1978): 2449-2452.

Tebas, Pablo, et al., "Safety and immunogenicity of INO-4800 DNA vaccine against SARS-CoV-2: A preliminary report of an open-label, Phase 1 clinical trial," EClinicalMedicine, Jan. 2021, 9 pages, 31.

* cited by examiner

MFVFLVLLPLVSSQCVNLTTRTQLPPAYTNSFTRGVYYPDKVFRSSVLHSTQDLF

LPFFSNVTWFHAIHVSGTNGTKRFDNPVLPFNDGVYFASTEKSNIIRGWIFGTTL

DSKTQSLLIVNNATNVVIKVCEFQFCNDPFLGVYYHKNNKSWMESEFRVYSSAN

NCTFEYVSQPFLMDLEGKQGNFKNLREFVFKNIDGYFKIYSKHTPINLVRDLPQ

GFSALEPLVDLPIGINITRFQTLLALHRSYLTPGDSSSGWTAGAAAYYVGYLQPR

TFL

LKYNENGTITDAVDCALDPLSETKCTLKSFTVEKGIYQTSNFRVQPTESIVRFPNI

TN

LCPFGEVFNATRFASVYAWNRKRISNCVADYSVLYNSASFSTFKCYGVSPTKLN

DLCFTNVYADSFVIRGDEVRQIAPGQTGKIADYNYKLPDDFTGCVIAWNSNNLD

SKVGGNYNYLYRLFRKSNLKPFERDISTEIYQAGSTPCNGVEGFNCYFPLQSYGF

QPTNGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITPGTNTSN

QVAVLYQDVNCTEVPVAIHADQLTPTWRVYSTGSNVFQTRAGCLIGAEHVNNS

YECDIPIGAGICASYQTQTNSPRRARSVASQSIIAYTMSLGAENSVAYSNNSIAIPT

NFTISVTTEILPVSMTKTSVDCTMYICGDSTECSNLLLQYGSFCTQLNRALTGIA

VEQDKNTQEVFAQVKQIYKTPPIKDFGGFNFSQILPDPSKPSKRSFIEDLLFNKVT

LADAGFIKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAIGKIQD

SLSSTASALGKLQDVVNQNAQALNTLVKQLSSNFGAISSVLNDILSRLDKVEAEV

QIDRLITGRLQSLQTYVTQQLIRAAEIRASANLAATKMSECVLGQSKRVDFCGK

GYHLMSFPQSAPHGVVFLHVTYVPAQEKNFTTAPAICHDGKAHFPREGVFVSN

GTHWFVTQRNFYEPQIITTDNTFVSGNCDVVIGIVNNTVYDPLQPELDSFKEELD

KYFKNHTSPDVDLGDISGINASVVNIQKEIDRLNEVAKNLNESLIDLQELGKYEQ

YIKWPWYIWLGFIAGLIAIVMVTIMLCCMTSCCSCLKGCCSCGSCCKFDEDDSE

PVLKGVKLHYT-P-10aa or 22aa-linker-P-*mysfvseetg tlivnsvllf lafvvfllvt lailtalrlc*

*ayccnivnvs lvkpsfyvys rvknlnssrv pdllv*-P-10aa or 22aa linker-P-madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq FIG. 4A-B
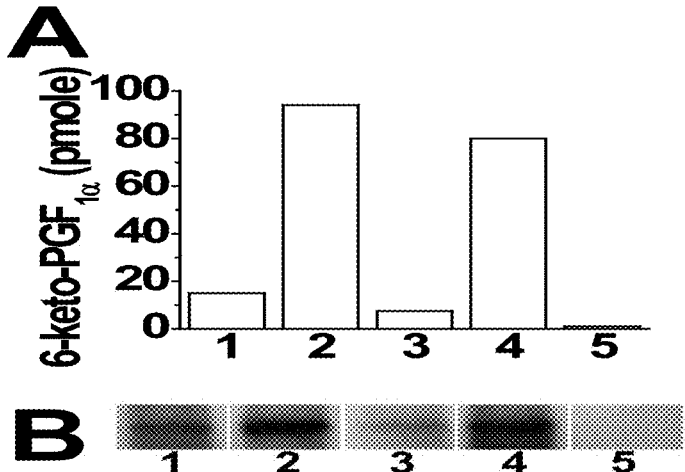

ꞁ Lane 1: Cloned pcDNA3.1-SC-SEM-1 plasmid
ꞁ Lane 2: Cloned pcDNA3.1-SC-SEM-1 plasmid
ꞁ digested by BAMHI
  Lane M: KB Ladder

Digestion Conditions:

About 300ng plasmid digested

Digestion in water-bath 37°C for 40 minutes

1% Agarose Gel

FIG. 9B

SC-V0-V3 protein sequence with 822 amino acid residues. (SEQ ID NO:14)

N-terminus.
TNLCPFGEVFNATRFASVYAWNRKRISNCVADYSVLYNSASFSTFKCYGVSPTKLNDLC
FTNVYADSFVIRGDEVRQIAPGQTGKIADYNYKLPDDFTGCVIAWNSNNLDSKVGGNY
NYLYRLFRKSNLKPFERDISTEIYQAGSTPCNGVEGFNCYFPLQSYGFQPTNGVGYQPY
RVVVLSFELLHAPATVCGP*PTIKPSPPSKSPAP*TNLCPFGEVFNATRFASVYAWNRKRI
SNCVADYSVLYNSASFSTFKCYGVSPTKLNDLCFTNVYADSFVIRGDEVRQIAPGQTGKI
ADYNYKLPDDFTGCVIAWNSNNLDSKVGGNYNYLYRLFRKSNLKPFERDISTEIYQAG
STPCNGVEGFNCYFPLQSYGFQPTYGVGYQPYRVVVLSFELLHAPATVCGP*PTIKPSPP*
*SKSPAP*TNLCPFGEVFNATRFASVYAWNRKRISNCVADYSVLYNSASFSTFKCYGVSPT
KLNDLCFTNVYADSFVIRGDEVRQIAPGQTGNIADYNYKLPDDFTGCVIAWNSNNLDS
KVGGNYNYLYRLFRKSNLKPFERDISTEIYQAGSTPCNGVKGFNCYFPLQSYGFQPTYG
VGYQPYRVVVLSFELLHAPATVCGP*PTIKPSPPSKSPAP*TNLCPFGEVFNATRFASVYA
WNRKRISNCVADYSVLYNSASFSTFKCYGVSPTKLNDLCFTNVYADSFVIRGDEVRQIA
PGQTGTIADYNYKLPDDFTGCVIAWNSNNLDSKVGGNYNYLYRLFRKSNLKPFERDIS
TEIYQAGNTPCNGVKGFNCYFPLQSYGFQPTYGVGYQPYRVVVLSFELLHAPATVCGP*
C-terminus.

V0/V3/V4

Gamma Variant

V3 (Variant 3)
Brazil, P.1/501Y.V3,
(K417T, E484K, N501Y)and
New York, B.1.526/S477N, E484K)

V0
Wild Type highly flexible 14 residue
linker

N-terminal

C-terminal

Delta Variant

V4 (Variant 4)
Indian, Delta, B.1.617.2
(T478K, L452R)

FIG. 10B

SC-V0/V3/V4 protein sequence with 613 amino acid residues. (SEQ ID NO:15)

N-terminus

TNLCPFGEVFNATRFASVYAWNRKRISNCVADYSVLYNSASFSTFKCYGVS
PTKLNDLCFTNVYADSFVIRGDEVRQIAPGQTGKIADYNYKLPDDFTGCVI
AWNSNNLDSKVGGNYNYLYRLFRKSNLKPFERDISTEIYQAGSTPCNGVE
GFNCYFPLQSYGFQPTNGVGYQPYRVVVLSFELLHAPATVCGP*PTIKPSPP*
*SKSPAP*TNLCPFGEVFNATRFASVYAWNRKRISNCVADYSVLYNSASFSTF
KCYGVSPTKLNDLCFTNVYADSFVIRGDEVRQIAPGQTGTIADYNYKLPD
DFTGCVIAWNSNNLDSKVGGNYNYLYRLFRKSNLKPFERDISTEIYQAGN
TPCNGVKGFNCYFPLQSYGFQPTYGVGYQPYRVVVLSFELLHAPATVCGP
*PTIKPSPPSKSPAP*TNLCPFGEVFNATRFASVYAWNRKRISNCVADYSVLY
NSASFSTFKCYGVSPTKLNDLCFTNVYADSFVIRGDEVRQIAPGQTGKIAD
YNYKLPDDFTGCVIAWNSNNLDSKVGGNYNYRYRLFRKSNLKPFERDIS
TEIYQAGSKPCNGVEGFNCYFPLQSYGFQPTNGVGYQPYRVVVLSFELLH
APATVCGP* C-terminus

SEQUENCE LISTING

<160> NUMBER OF SEQ ID NOS: 18

<210> SEQ ID NO 1
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile

```
            115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
        500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540
```

-continued

```
Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960
```

```
Thr Leu Val Lys Gln Leu Ser Ser Asn Phe Gly Ala Ile Ser Ser Val
              965                 970                 975

Leu Asn Asp Ile Leu Ser Arg Leu Asp Lys Val Glu Ala Glu Val Gln
              980                 985                 990

Ile Asp Arg Leu Ile Thr Gly Arg  Leu Gln Ser Leu Gln  Thr Tyr Val
         995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125

Val Ile  Gly Ile Val Asn Asn  Thr Val Tyr Asp Pro  Leu Gln Pro
    1130                 1135                1140

Glu Leu  Asp Ser Phe Lys Glu  Glu Leu Asp Lys Tyr  Phe Lys Asn
    1145                 1150                1155

His Thr  Ser Pro Asp Val Asp  Leu Gly Asp Ile Ser  Gly Ile Asn
    1160                 1165                1170

Ala Ser  Val Val Asn Ile Gln  Lys Glu Ile Asp Arg  Leu Asn Glu
    1175                 1180                1185

Val Ala  Lys Asn Leu Asn Glu  Ser Leu Ile Asp Leu  Gln Glu Leu
    1190                 1195                1200

Gly Lys  Tyr Glu Gln Tyr Ile  Lys Trp Pro Trp Tyr  Ile Trp Leu
    1205                 1210                1215

Gly Phe  Ile Ala Gly Leu Ile  Ala Ile Val Met Val  Thr Ile Met
    1220                 1225                1230

Leu Cys  Cys Met Thr Ser Cys  Cys Ser Cys Leu Lys  Gly Cys Cys
    1235                 1240                1245

Ser Cys  Gly Ser Cys Cys Lys  Phe Asp Glu Asp Asp  Ser Glu Pro
    1250                 1255                1260

Val Leu  Lys Gly Val Lys Leu  His Tyr Thr
    1265                 1270
```

```
<210> SEQ ID NO 2
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
              20                  25                  30
```

```
Ile Leu Thr Ala Leu Arg Leu Cys Ala Tyr Cys Cys Asn Ile Val Asn
        35              40              45

Val Ser Leu Val Lys Pro Ser Phe Tyr Val Tyr Ser Arg Val Lys Asn
    50              55              60

Leu Asn Ser Ser Arg Val Pro Asp Leu Leu Val
65              70              75

<210> SEQ ID NO 3
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Asp Ser Asn Gly Thr Ile Thr Val Glu Glu Leu Lys Lys Leu
1               5               10              15

Leu Glu Gln Trp Asn Leu Val Ile Gly Phe Leu Phe Leu Thr Trp Ile
            20              25              30

Cys Leu Leu Gln Phe Ala Tyr Ala Asn Arg Asn Arg Phe Leu Tyr Ile
        35              40              45

Ile Lys Leu Ile Phe Leu Trp Leu Leu Trp Pro Val Thr Leu Ala Cys
    50              55              60

Phe Val Leu Ala Ala Val Tyr Arg Ile Asn Trp Ile Thr Gly Gly Ile
65              70              75              80

Ala Ile Ala Met Ala Cys Leu Val Gly Leu Met Trp Leu Ser Tyr Phe
                85              90              95

Ile Ala Ser Phe Arg Leu Phe Ala Arg Thr Arg Ser Met Trp Ser Phe
            100             105             110

Asn Pro Glu Thr Asn Ile Leu Leu Asn Val Pro Leu His Gly Thr Ile
        115             120             125

Leu Thr Arg Pro Leu Leu Glu Ser Glu Leu Val Ile Gly Ala Val Ile
        130             135             140

Leu Arg Gly His Leu Arg Ile Ala Gly His His Leu Gly Arg Cys Asp
145             150             155             160

Ile Lys Asp Leu Pro Lys Glu Ile Thr Val Ala Thr Ser Arg Thr Leu
                165             170             175

Ser Tyr Tyr Lys Leu Gly Ala Ser Gln Arg Val Ala Gly Asp Ser Gly
            180             185             190

Phe Ala Ala Tyr Ser Arg Tyr Arg Ile Gly Asn Tyr Lys Leu Asn Thr
        195             200             205

Asp His Ser Ser Ser Ser Asp Asn Ile Ala Leu Leu Val Gln
    210             215             220

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ala Ile Met Gly Val Ala Phe Thr Trp
1               5               10

<210> SEQ ID NO 5
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ala Ile Met Gly Val Ala Phe Thr Trp Val Met Ala Leu Ala Cys
1               5                   10                  15

Ala Ala Pro Pro Leu Val
            20

<210> SEQ ID NO 6
<211> LENGTH: 1606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285
```

-continued

```
Val Asp Cys Ala Leu Asp Pro Leu Ser Glu Thr Lys Cys Thr Leu Lys
    290             295             300
```

```
Ser Phe Thr Val Glu Lys Gly Ile Tyr Gln Thr Ser Asn Phe Arg Val
305             310             315             320
```

```
Gln Pro Thr Glu Ser Ile Val Arg Phe Pro Asn Ile Thr Asn Leu Cys
            325             330             335
```

```
Pro Phe Gly Glu Val Phe Asn Ala Thr Arg Phe Ala Ser Val Tyr Ala
            340             345             350
```

```
Trp Asn Arg Lys Arg Ile Ser Asn Cys Val Ala Asp Tyr Ser Val Leu
            355             360             365
```

```
Tyr Asn Ser Ala Ser Phe Ser Thr Phe Lys Cys Tyr Gly Val Ser Pro
    370             375             380
```

```
Thr Lys Leu Asn Asp Leu Cys Phe Thr Asn Val Tyr Ala Asp Ser Phe
385             390             395             400
```

```
Val Ile Arg Gly Asp Glu Val Arg Gln Ile Ala Pro Gly Gln Thr Gly
            405             410             415
```

```
Lys Ile Ala Asp Tyr Asn Tyr Lys Leu Pro Asp Asp Phe Thr Gly Cys
            420             425             430
```

```
Val Ile Ala Trp Asn Ser Asn Asn Leu Asp Ser Lys Val Gly Gly Asn
    435             440             445
```

```
Tyr Asn Tyr Leu Tyr Arg Leu Phe Arg Lys Ser Asn Leu Lys Pro Phe
    450             455             460
```

```
Glu Arg Asp Ile Ser Thr Glu Ile Tyr Gln Ala Gly Ser Thr Pro Cys
465             470             475             480
```

```
Asn Gly Val Glu Gly Phe Asn Cys Tyr Phe Pro Leu Gln Ser Tyr Gly
            485             490             495
```

```
Phe Gln Pro Thr Asn Gly Val Gly Tyr Gln Pro Tyr Arg Val Val Val
            500             505             510
```

```
Leu Ser Phe Glu Leu Leu His Ala Pro Ala Thr Val Cys Gly Pro Lys
            515             520             525
```

```
Lys Ser Thr Asn Leu Val Lys Asn Lys Cys Val Asn Phe Asn Phe Asn
    530             535             540
```

```
Gly Leu Thr Gly Thr Gly Val Leu Thr Glu Ser Asn Lys Lys Phe Leu
545             550             555             560
```

```
Pro Phe Gln Gln Phe Gly Arg Asp Ile Ala Asp Thr Thr Asp Ala Val
            565             570             575
```

```
Arg Asp Pro Gln Thr Leu Glu Ile Leu Asp Ile Thr Pro Cys Ser Phe
            580             585             590
```

```
Gly Gly Val Ser Val Ile Thr Pro Gly Thr Asn Thr Ser Asn Gln Val
            595             600             605
```

```
Ala Val Leu Tyr Gln Asp Val Asn Cys Thr Glu Val Pro Val Ala Ile
    610             615             620
```

```
His Ala Asp Gln Leu Thr Pro Thr Trp Arg Val Tyr Ser Thr Gly Ser
625             630             635             640
```

```
Asn Val Phe Gln Thr Arg Ala Gly Cys Leu Ile Gly Ala Glu His Val
            645             650             655
```

```
Asn Asn Ser Tyr Glu Cys Asp Ile Pro Ile Gly Ala Gly Ile Cys Ala
            660             665             670
```

```
Ser Tyr Gln Thr Gln Thr Asn Ser Pro Arg Arg Ala Arg Ser Val Ala
    675             680             685
```

```
Ser Gln Ser Ile Ile Ala Tyr Thr Met Ser Leu Gly Ala Glu Asn Ser
    690             695             700
```

-continued

```
Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Ala Ser Ala
930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
            995             1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
```

-continued

```
                1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Ser  Glu Pro
    1250                1255                1260

Val Leu  Lys Gly Val Lys Leu  His Tyr Thr Pro His  Ala Ile Met
    1265                1270                1275

Gly Val  Ala Phe Thr Trp Pro  Met Tyr Ser Phe Val  Ser Glu Glu
    1280                1285                1290

Thr Gly  Thr Leu Ile Val Asn  Ser Val Leu Leu Phe  Leu Ala Phe
    1295                1300                1305

Val Val  Phe Leu Leu Val Thr  Leu Ala Ile Leu Thr  Ala Leu Arg
    1310                1315                1320

Leu Cys  Ala Tyr Cys Cys Asn  Ile Val Asn Val Ser  Leu Val Lys
    1325                1330                1335

Pro Ser  Phe Tyr Val Tyr Ser  Arg Val Lys Asn Leu  Asn Ser Ser
    1340                1345                1350

Arg Val  Pro Asp Leu Leu Val  Pro His Ala Ile Met  Gly Val Ala
    1355                1360                1365

Phe Thr  Trp Val Met Ala Leu  Ala Cys Ala Ala Pro  Pro Leu Val
    1370                1375                1380

Pro Met  Ala Asp Ser Asn Gly  Thr Ile Thr Val Glu  Glu Leu Lys
    1385                1390                1395

Lys Leu  Leu Glu Gln Trp Asn  Leu Val Ile Gly Phe  Leu Phe Leu
    1400                1405                1410

Thr Trp  Ile Cys Leu Leu Gln  Phe Ala Tyr Ala Asn  Arg Asn Arg
    1415                1420                1425

Phe Leu  Tyr Ile Ile Lys Leu  Ile Phe Leu Trp Leu  Leu Trp Pro
    1430                1435                1440

Val Thr  Leu Ala Cys Phe Val  Leu Ala Ala Val Tyr  Arg Ile Asn
    1445                1450                1455

Trp Ile  Thr Gly Gly Ile Ala  Ile Ala Met Ala Cys  Leu Val Gly
    1460                1465                1470

Leu Met  Trp Leu Ser Tyr Phe  Ile Ala Ser Phe Arg  Leu Phe Ala
    1475                1480                1485

Arg Thr  Arg Ser Met Trp Ser  Phe Asn Pro Glu Thr  Asn Ile Leu
    1490                1495                1500

Leu Asn  Val Pro Leu His Gly  Thr Ile Leu Thr Arg  Pro Leu Leu
    1505                1510                1515
```

```
Glu Ser  Glu Leu Val Ile Gly  Ala Val Ile Leu Arg  Gly His Leu
    1520            1525            1530

Arg Ile  Ala Gly His His Leu  Gly Arg Cys Asp Ile  Lys Asp Leu
    1535            1540            1545

Pro Lys  Glu Ile Thr Val Ala  Thr Ser Arg Thr Leu  Ser Tyr Tyr
    1550            1555            1560

Lys Leu  Gly Ala Ser Gln Arg  Val Ala Gly Asp Ser  Gly Phe Ala
    1565            1570            1575

Ala Tyr  Ser Arg Tyr Arg Ile  Gly Asn Tyr Lys Leu  Asn Thr Asp
    1580            1585            1590

His Ser  Ser Ser Ser Asp Asn  Ile Ala Leu Leu Val  Gln
    1595            1600            1605

<210> SEQ ID NO 7
<211> LENGTH: 1594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
```

```
              260              265              270
Arg Thr Phe Leu Leu Lys Tyr Asn Glu Asn Gly Thr Ile Thr Asp Ala
        275              280              285

Val Asp Cys Ala Leu Asp Pro Leu Ser Glu Thr Lys Cys Thr Leu Lys
        290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
                325              330              335

Pro Phe Gly Glu Val Phe Asn Ala Thr Arg Phe Ala Ser Val Tyr Ala
                340              345              350

Trp Asn Arg Lys Arg Ile Ser Asn Cys Val Ala Asp Tyr Ser Val Leu
                355              360              365

Tyr Asn Ser Ala Ser Phe Ser Thr Phe Lys Cys Tyr Gly Val Ser Pro
        370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
                405              410              415

Lys Ile Ala Asp Tyr Asn Tyr Lys Leu Pro Asp Asp Phe Thr Gly Cys
                420              425              430

Val Ile Ala Trp Asn Ser Asn Asn Leu Asp Ser Lys Val Gly Gly Asn
        435              440              445

Tyr Asn Tyr Leu Tyr Arg Leu Phe Arg Lys Ser Asn Leu Lys Pro Phe
        450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
                485              490              495

Phe Gln Pro Thr Asn Gly Val Gly Tyr Gln Pro Tyr Arg Val Val Val
                500              505              510

Leu Ser Phe Glu Leu Leu His Ala Pro Ala Thr Val Cys Gly Pro Lys
                515              520              525

Lys Ser Thr Asn Leu Val Lys Asn Lys Cys Val Asn Phe Asn Phe Asn
        530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
                565              570              575

Arg Asp Pro Gln Thr Leu Glu Ile Leu Asp Ile Thr Pro Cys Ser Phe
                580              585              590

Gly Gly Val Ser Val Ile Thr Pro Gly Thr Asn Thr Ser Asn Gln Val
                595              600              605

Ala Val Leu Tyr Gln Asp Val Asn Cys Thr Glu Val Pro Val Ala Ile
        610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
                645              650              655

Asn Asn Ser Tyr Glu Cys Asp Ile Pro Ile Gly Ala Gly Ile Cys Ala
                660              665              670

Ser Tyr Gln Thr Gln Thr Asn Ser Pro Arg Arg Ala Arg Ser Val Ala
        675              680              685
```

-continued

```
Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095
```

-continued

```
Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Lys Leu His Tyr Thr Pro His Ala Ile Met
    1265                1270                1275

Gly Val Ala Phe Thr Trp Pro Met Tyr Ser Phe Val Ser Glu Glu
    1280                1285                1290

Thr Gly Thr Leu Ile Val Asn Ser Val Leu Leu Phe Leu Ala Phe
    1295                1300                1305

Val Val Phe Leu Leu Val Thr Leu Ala Ile Leu Thr Ala Leu Arg
    1310                1315                1320

Leu Cys Ala Tyr Cys Cys Asn Ile Val Asn Val Ser Leu Val Lys
    1325                1330                1335

Pro Ser Phe Tyr Val Tyr Ser Arg Val Lys Asn Leu Asn Ser Ser
    1340                1345                1350

Arg Val Pro Asp Leu Leu Val Pro His Ala Ile Met Gly Val Ala
    1355                1360                1365

Phe Thr Trp Pro Met Ala Asp Ser Asn Gly Thr Ile Thr Val Glu
    1370                1375                1380

Glu Leu Lys Lys Leu Leu Glu Gln Trp Asn Leu Val Ile Gly Phe
    1385                1390                1395

Leu Phe Leu Thr Trp Ile Cys Leu Leu Gln Phe Ala Tyr Ala Asn
    1400                1405                1410

Arg Asn Arg Phe Leu Tyr Ile Ile Lys Leu Ile Phe Leu Trp Leu
    1415                1420                1425

Leu Trp Pro Val Thr Leu Ala Cys Phe Val Leu Ala Ala Val Tyr
    1430                1435                1440

Arg Ile Asn Trp Ile Thr Gly Gly Ile Ala Ile Ala Met Ala Cys
    1445                1450                1455

Leu Val Gly Leu Met Trp Leu Ser Tyr Phe Ile Ala Ser Phe Arg
    1460                1465                1470

Leu Phe Ala Arg Thr Arg Ser Met Trp Ser Phe Asn Pro Glu Thr
    1475                1480                1485

Asn Ile Leu Leu Asn Val Pro Leu His Gly Thr Ile Leu Thr Arg
```

-continued

```
             1490              1495              1500

Pro Leu  Leu Glu Ser Glu Leu  Val Ile Gly Ala Val  Ile Leu Arg
    1505              1510              1515

Gly His  Leu Arg Ile Ala Gly  His His Leu Gly Arg  Cys Asp Ile
    1520              1525              1530

Lys Asp  Leu Pro Lys Glu Ile  Thr Val Ala Thr Ser  Arg Thr Leu
    1535              1540              1545

Ser Tyr  Tyr Lys Leu Gly Ala  Ser Gln Arg Val Ala  Gly Asp Ser
    1550              1555              1560

Gly Phe  Ala Ala Tyr Ser Arg  Tyr Arg Ile Gly Asn  Tyr Lys Leu
    1565              1570              1575

Asn Thr  Asp His Ser Ser Ser  Ser Asp Asn Ile Ala  Leu Leu Val
    1580              1585              1590

Gln

<210> SEQ ID NO 8
<211> LENGTH: 1606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
```

-continued

```
                245              250              255

Gly Trp Thr Ala Gly Ala Ala Ala Tyr Tyr Val Gly Tyr Leu Gln Pro
            260              265              270

Arg Thr Phe Leu Leu Lys Tyr Asn Glu Asn Gly Thr Ile Thr Asp Ala
            275              280              285

Val Asp Cys Ala Leu Asp Pro Leu Ser Glu Thr Lys Cys Thr Leu Lys
            290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
                325              330              335

Pro Phe Gly Glu Val Phe Asn Ala Thr Arg Phe Ala Ser Val Tyr Ala
            340              345              350

Trp Asn Arg Lys Arg Ile Ser Asn Cys Val Ala Asp Tyr Ser Val Leu
            355              360              365

Tyr Asn Ser Ala Ser Phe Ser Thr Phe Lys Cys Tyr Gly Val Ser Pro
            370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
                405              410              415

Lys Ile Ala Asp Tyr Asn Tyr Lys Leu Pro Asp Asp Phe Thr Gly Cys
            420              425              430

Val Ile Ala Trp Asn Ser Asn Asn Leu Asp Ser Lys Val Gly Gly Asn
            435              440              445

Tyr Asn Tyr Leu Tyr Arg Leu Phe Arg Lys Ser Asn Leu Lys Pro Phe
            450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
                485              490              495

Phe Gln Pro Thr Asn Gly Val Gly Tyr Gln Pro Tyr Arg Val Val Val
            500              505              510

Leu Ser Phe Glu Leu Leu His Ala Pro Ala Thr Val Cys Gly Pro Lys
            515              520              525

Lys Ser Thr Asn Leu Val Lys Asn Lys Cys Val Asn Phe Asn Phe Asn
530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
            565              570              575

Arg Asp Pro Gln Thr Leu Glu Ile Leu Asp Ile Thr Pro Cys Ser Phe
            580              585              590

Gly Gly Val Ser Val Ile Thr Pro Gly Thr Asn Thr Ser Asn Gln Val
            595              600              605

Ala Val Leu Tyr Gln Asp Val Asn Cys Thr Glu Val Pro Val Ala Ile
            610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
                645              650              655

Asn Asn Ser Tyr Glu Cys Asp Ile Pro Ile Gly Ala Gly Ile Cys Ala
            660              665              670
```

-continued

```
Ser Tyr Gln Thr Gln Thr Asn Ser Pro Arg Arg Ala Arg Ser Val Ala
        675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
        850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
        930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080
```

```
Asp Gly Lys Ala His Phe Pro Arg Glu Gly Val Phe Val Ser Asn
    1085             1090             1095

Gly Thr His Trp Phe Val Thr Gln Arg Asn Phe Tyr Glu Pro Gln
    1100             1105             1110

Ile Ile Thr Thr Asp Asn Thr Phe Val Ser Gly Asn Cys Asp Val
    1115             1120             1125

Val Ile Gly Ile Val Asn Asn Thr Val Tyr Asp Pro Leu Gln Pro
    1130             1135             1140

Glu Leu Asp Ser Phe Lys Glu Glu Leu Asp Lys Tyr Phe Lys Asn
    1145             1150             1155

His Thr Ser Pro Asp Val Asp Leu Gly Asp Ile Ser Gly Ile Asn
    1160             1165             1170

Ala Ser Val Val Asn Ile Gln Lys Glu Ile Asp Arg Leu Asn Glu
    1175             1180             1185

Val Ala Lys Asn Leu Asn Glu Ser Leu Ile Asp Leu Gln Glu Leu
    1190             1195             1200

Gly Lys Tyr Glu Gln Tyr Ile Lys Trp Pro Trp Tyr Ile Trp Leu
    1205             1210             1215

Gly Phe Ile Ala Gly Leu Ile Ala Ile Val Met Val Thr Ile Met
    1220             1225             1230

Leu Cys Cys Met Thr Ser Cys Cys Ser Cys Leu Lys Gly Cys Cys
    1235             1240             1245

Ser Cys Gly Ser Cys Cys Lys Phe Asp Glu Asp Asp Ser Glu Pro
    1250             1255             1260

Val Leu Lys Gly Val Lys Leu His Tyr Thr Pro His Ala Ile Met
    1265             1270             1275

Gly Val Ala Phe Thr Trp Val Met Ala Leu Ala Cys Ala Ala Pro
    1280             1285             1290

Pro Leu Val Pro Met Tyr Ser Phe Val Ser Glu Glu Thr Gly Thr
    1295             1300             1305

Leu Ile Val Asn Ser Val Leu Leu Phe Leu Ala Phe Val Val Phe
    1310             1315             1320

Leu Leu Val Thr Leu Ala Ile Leu Thr Ala Leu Arg Leu Cys Ala
    1325             1330             1335

Tyr Cys Cys Asn Ile Val Asn Val Ser Leu Val Lys Pro Ser Phe
    1340             1345             1350

Tyr Val Tyr Ser Arg Val Lys Asn Leu Asn Ser Ser Arg Val Pro
    1355             1360             1365

Asp Leu Leu Val Pro His Ala Ile Met Gly Val Ala Phe Thr Trp
    1370             1375             1380

Pro Met Ala Asp Ser Asn Gly Thr Ile Thr Val Glu Glu Leu Lys
    1385             1390             1395

Lys Leu Leu Glu Gln Trp Asn Leu Val Ile Gly Phe Leu Phe Leu
    1400             1405             1410

Thr Trp Ile Cys Leu Leu Gln Phe Ala Tyr Ala Asn Arg Asn Arg
    1415             1420             1425

Phe Leu Tyr Ile Ile Lys Leu Ile Phe Leu Trp Leu Leu Trp Pro
    1430             1435             1440

Val Thr Leu Ala Cys Phe Val Leu Ala Ala Val Tyr Arg Ile Asn
    1445             1450             1455

Trp Ile Thr Gly Gly Ile Ala Ile Ala Met Ala Cys Leu Val Gly
    1460             1465             1470

Leu Met Trp Leu Ser Tyr Phe Ile Ala Ser Phe Arg Leu Phe Ala
```

```
            1475                1480                1485
Arg Thr  Arg Ser Met Trp Ser  Phe Asn Pro Glu Thr  Asn Ile Leu
    1490                1495                1500
Leu Asn  Val Pro Leu His Gly  Thr Ile Leu Thr Arg  Pro Leu Leu
    1505                1510                1515
Glu Ser  Glu Leu Val Ile Gly  Ala Val Ile Leu Arg  Gly His Leu
    1520                1525                1530
Arg Ile  Ala Gly His His Leu  Gly Arg Cys Asp Ile  Lys Asp Leu
    1535                1540                1545
Pro Lys  Glu Ile Thr Val Ala  Thr Ser Arg Thr Leu  Ser Tyr Tyr
    1550                1555                1560
Lys Leu  Gly Ala Ser Gln Arg  Val Ala Gly Asp Ser  Gly Phe Ala
    1565                1570                1575
Ala Tyr  Ser Arg Tyr Arg Ile  Gly Asn Tyr Lys Leu  Asn Thr Asp
    1580                1585                1590
His Ser  Ser Ser Ser Asp Asn  Ile Ala Leu Leu Val  Gln
    1595                1600                1605
```

<210> SEQ ID NO 9
<211> LENGTH: 1618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Phe Val Phe Leu Val Leu Leu Pro Leu Val Ser Ser Gln Cys Val
1               5                   10                  15
Asn Leu Thr Thr Arg Thr Gln Leu Pro Pro Ala Tyr Thr Asn Ser Phe
            20                  25                  30
Thr Arg Gly Val Tyr Tyr Pro Asp Lys Val Phe Arg Ser Ser Val Leu
        35                  40                  45
His Ser Thr Gln Asp Leu Phe Leu Pro Phe Phe Ser Asn Val Thr Trp
    50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
            85                  90                  95
Lys Ser Asn Ile Ile Arg Gly Trp Ile Phe Gly Thr Thr Leu Asp Ser
            100                 105                 110
Lys Thr Gln Ser Leu Leu Ile Val Asn Asn Ala Thr Asn Val Val Ile
        115                 120                 125
Lys Val Cys Glu Phe Gln Phe Cys Asn Asp Pro Phe Leu Gly Val Tyr
    130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
            165                 170                 175
Met Asp Leu Glu Gly Lys Gln Gly Asn Phe Lys Asn Leu Arg Glu Phe
            180                 185                 190
Val Phe Lys Asn Ile Asp Gly Tyr Phe Lys Ile Tyr Ser Lys His Thr
        195                 200                 205
Pro Ile Asn Leu Val Arg Asp Leu Pro Gln Gly Phe Ser Ala Leu Glu
    210                 215                 220
```

-continued

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
```

-continued

```
                 645            650             655

Asn Asn Ser Tyr Glu Cys Asp Ile Pro Ile Gly Ala Gly Ile Cys Ala
            660            665             670

Ser Tyr Gln Thr Gln Thr Asn Ser Pro Arg Arg Ala Arg Ser Val Ala
            675            680             685

Ser Gln Ser Ile Ile Ala Tyr Thr Met Ser Leu Gly Ala Glu Asn Ser
       690            695             700

Val Ala Tyr Ser Asn Asn Ser Ile Ala Ile Pro Thr Asn Phe Thr Ile
705            710             715            720

Ser Val Thr Thr Glu Ile Leu Pro Val Ser Met Thr Lys Thr Ser Val
            725            730             735

Asp Cys Thr Met Tyr Ile Cys Gly Asp Ser Thr Glu Cys Ser Asn Leu
            740            745             750

Leu Leu Gln Tyr Gly Ser Phe Cys Thr Gln Leu Asn Arg Ala Leu Thr
            755            760             765

Gly Ile Ala Val Glu Gln Asp Lys Asn Thr Gln Glu Val Phe Ala Gln
       770            775             780

Val Lys Gln Ile Tyr Lys Thr Pro Pro Ile Lys Asp Phe Gly Gly Phe
785            790             795            800

Asn Phe Ser Gln Ile Leu Pro Asp Pro Ser Lys Pro Ser Lys Arg Ser
            805            810             815

Phe Ile Glu Asp Leu Leu Phe Asn Lys Val Thr Leu Ala Asp Ala Gly
            820            825             830

Phe Ile Lys Gln Tyr Gly Asp Cys Leu Gly Asp Ile Ala Ala Arg Asp
            835            840             845

Leu Ile Cys Ala Gln Lys Phe Asn Gly Leu Thr Val Leu Pro Pro Leu
       850            855             860

Leu Thr Asp Glu Met Ile Ala Gln Tyr Thr Ser Ala Leu Leu Ala Gly
865            870             875            880

Thr Ile Thr Ser Gly Trp Thr Phe Gly Ala Gly Ala Ala Leu Gln Ile
            885            890             895

Pro Phe Ala Met Gln Met Ala Tyr Arg Phe Asn Gly Ile Gly Val Thr
            900            905             910

Gln Asn Val Leu Tyr Glu Asn Gln Lys Leu Ile Ala Asn Gln Phe Asn
       915            920             925

Ser Ala Ile Gly Lys Ile Gln Asp Ser Leu Ser Ser Thr Ala Ser Ala
       930            935             940

Leu Gly Lys Leu Gln Asp Val Val Asn Gln Asn Ala Gln Ala Leu Asn
945            950             955            960

Thr Leu Val Lys Gln Leu Ser Ser Asn Phe Gly Ala Ile Ser Ser Val
            965            970             975

Leu Asn Asp Ile Leu Ser Arg Leu Asp Lys Val Glu Ala Glu Val Gln
            980            985             990

Ile Asp Arg Leu Ile Thr Gly Arg  Leu Gln Ser Leu Gln  Thr Tyr Val
       995            1000             1005

Thr Gln  Gln Leu Ile Arg Ala  Ala Glu Ile Arg Ala  Ser Ala Asn
   1010            1015             1020

Leu Ala  Ala Thr Lys Met Ser  Glu Cys Val Leu Gly  Gln Ser Lys
   1025            1030             1035

Arg Val  Asp Phe Cys Gly Lys  Gly Tyr His Leu Met  Ser Phe Pro
   1040            1045             1050

Gln Ser  Ala Pro His Gly Val  Val Phe Leu His Val  Thr Tyr Val
   1055            1060             1065
```

```
Pro Ala Gln Glu Lys Asn Phe  Thr Thr Ala Pro Ala  Ile Cys His
    1070              1075              1080

Asp Gly Lys Ala His Phe Pro  Arg Glu Gly Val Phe  Val Ser Asn
    1085              1090              1095

Gly Thr His Trp Phe Val Thr  Gln Arg Asn Phe Tyr  Glu Pro Gln
    1100              1105              1110

Ile Ile Thr Thr Asp Asn Thr  Phe Val Ser Gly Asn  Cys Asp Val
    1115              1120              1125

Val Ile Gly Ile Val Asn Asn  Thr Val Tyr Asp Pro  Leu Gln Pro
    1130              1135              1140

Glu Leu Asp Ser Phe Lys Glu  Glu Leu Asp Lys Tyr  Phe Lys Asn
    1145              1150              1155

His Thr Ser Pro Asp Val Asp  Leu Gly Asp Ile Ser  Gly Ile Asn
    1160              1165              1170

Ala Ser Val Val Asn Ile Gln  Lys Glu Ile Asp Arg  Leu Asn Glu
    1175              1180              1185

Val Ala Lys Asn Leu Asn Glu  Ser Leu Ile Asp Leu  Gln Glu Leu
    1190              1195              1200

Gly Lys Tyr Glu Gln Tyr Ile  Lys Trp Pro Trp Tyr  Ile Trp Leu
    1205              1210              1215

Gly Phe Ile Ala Gly Leu Ile  Ala Ile Val Met Val  Thr Ile Met
    1220              1225              1230

Leu Cys Cys Met Thr Ser Cys  Cys Ser Cys Leu Lys  Gly Cys Cys
    1235              1240              1245

Ser Cys Gly Ser Cys Cys Lys  Phe Asp Glu Asp Asp  Ser Glu Pro
    1250              1255              1260

Val Leu Lys Gly Val Lys Leu  His Tyr Thr Pro His  Ala Ile Met
    1265              1270              1275

Gly Val Ala Phe Thr Trp Val  Met Ala Leu Ala Cys  Ala Ala Pro
    1280              1285              1290

Pro Leu Val Pro Met Tyr Ser  Phe Val Ser Glu Glu  Thr Gly Thr
    1295              1300              1305

Leu Ile Val Asn Ser Val Leu  Leu Phe Leu Ala Phe  Val Val Phe
    1310              1315              1320

Leu Leu Val Thr Leu Ala Ile  Leu Thr Ala Leu Arg  Leu Cys Ala
    1325              1330              1335

Tyr Cys Cys Asn Ile Val Asn  Val Ser Leu Val Lys  Pro Ser Phe
    1340              1345              1350

Tyr Val Tyr Ser Arg Val Lys  Asn Leu Asn Ser Ser  Arg Val Pro
    1355              1360              1365

Asp Leu Leu Val Pro His Ala  Ile Met Gly Val Ala  Phe Thr Trp
    1370              1375              1380

Val Met Ala Leu Ala Cys Ala  Ala Pro Pro Leu Val  Pro Met Ala
    1385              1390              1395

Asp Ser Asn Gly Thr Ile Thr  Val Glu Glu Leu Lys  Lys Leu Leu
    1400              1405              1410

Glu Gln Trp Asn Leu Val Ile  Gly Phe Leu Phe Leu  Thr Trp Ile
    1415              1420              1425

Cys Leu Leu Gln Phe Ala Tyr  Ala Asn Arg Asn Arg  Phe Leu Tyr
    1430              1435              1440

Ile Ile Lys Leu Ile Phe Leu  Trp Leu Leu Trp Pro  Val Thr Leu
    1445              1450              1455
```

-continued

```
Ala Cys Phe Val Leu Ala Ala  Val Tyr Arg Ile Asn  Trp Ile Thr
    1460            1465                1470

Gly Gly Ile Ala Ile Ala Met  Ala Cys Leu Val Gly  Leu Met Trp
    1475            1480                1485

Leu Ser Tyr Phe Ile Ala Ser  Phe Arg Leu Phe Ala  Arg Thr Arg
    1490            1495                1500

Ser Met Trp Ser Phe Asn Pro  Glu Thr Asn Ile Leu  Leu Asn Val
    1505            1510                1515

Pro Leu His Gly Thr Ile Leu  Thr Arg Pro Leu Leu  Glu Ser Glu
    1520            1525                1530

Leu Val Ile Gly Ala Val Ile  Leu Arg Gly His Leu  Arg Ile Ala
    1535            1540                1545

Gly His His Leu Gly Arg Cys  Asp Ile Lys Asp Leu  Pro Lys Glu
    1550            1555                1560

Ile Thr Val Ala Thr Ser Arg  Thr Leu Ser Tyr Tyr  Lys Leu Gly
    1565            1570                1575

Ala Ser Gln Arg Val Ala Gly  Asp Ser Gly Phe Ala  Ala Tyr Ser
    1580            1585                1590

Arg Tyr Arg Ile Gly Asn Tyr  Lys Leu Asn Thr Asp  His Ser Ser
    1595            1600                1605

Ser Ser Asp Asn Ile Ala Leu  Leu Val Gln
    1610            1615

<210> SEQ ID NO 10
<211> LENGTH: 1606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
                180                 185                 190
```

-continued

```
Phe Ala Ala Tyr Ser Arg Tyr Arg Ile Gly Asn Tyr Lys Leu Asn Thr
        195             200             205

Asp His Ser Ser Ser Ser Asp Asn Ile Ala Leu Leu Val Gln Pro His
        210             215             220

Ala Ile Met Gly Val Ala Phe Thr Trp Pro Met Tyr Ser Phe Val Ser
225             230             235             240

Glu Glu Thr Gly Thr Leu Ile Val Asn Ser Val Leu Leu Phe Leu Ala
            245             250             255

Phe Val Val Phe Leu Leu Val Thr Leu Ala Ile Leu Thr Ala Leu Arg
            260             265             270

Leu Cys Ala Tyr Cys Cys Asn Ile Val Asn Val Ser Leu Val Lys Pro
            275             280             285

Ser Phe Tyr Val Tyr Ser Arg Val Lys Asn Leu Asn Ser Ser Arg Val
        290             295             300

Pro Asp Leu Leu Val Pro His Ala Ile Met Gly Val Ala Phe Thr Trp
305             310             315             320

Val Met Ala Leu Ala Cys Ala Ala Pro Pro Leu Val Pro Met Phe Val
            325             330             335

Phe Leu Val Leu Leu Pro Leu Val Ser Ser Gln Cys Val Asn Leu Thr
            340             345             350

Thr Arg Thr Gln Leu Pro Pro Ala Tyr Thr Asn Ser Phe Thr Arg Gly
        355             360             365

Val Tyr Tyr Pro Asp Lys Val Phe Arg Ser Ser Val Leu His Ser Thr
        370             375             380

Gln Asp Leu Phe Leu Pro Phe Phe Ser Asn Val Thr Trp Phe His Ala
385             390             395             400

Ile His Val Ser Gly Thr Asn Gly Thr Lys Arg Phe Asp Asn Pro Val
            405             410             415

Leu Pro Phe Asn Asp Gly Val Tyr Phe Ala Ser Thr Glu Lys Ser Asn
            420             425             430

Ile Ile Arg Gly Trp Ile Phe Gly Thr Thr Leu Asp Ser Lys Thr Gln
            435             440             445

Ser Leu Leu Ile Val Asn Asn Ala Thr Asn Val Val Ile Lys Val Cys
        450             455             460

Glu Phe Gln Phe Cys Asn Asp Pro Phe Leu Gly Val Tyr Tyr His Lys
465             470             475             480

Asn Asn Lys Ser Trp Met Glu Ser Glu Phe Arg Val Tyr Ser Ser Ala
            485             490             495

Asn Asn Cys Thr Phe Glu Tyr Val Ser Gln Pro Phe Leu Met Asp Leu
            500             505             510

Glu Gly Lys Gln Gly Asn Phe Lys Asn Leu Arg Glu Phe Val Phe Lys
            515             520             525

Asn Ile Asp Gly Tyr Phe Lys Ile Tyr Ser Lys His Thr Pro Ile Asn
        530             535             540

Leu Val Arg Asp Leu Pro Gln Gly Phe Ser Ala Leu Glu Pro Leu Val
545             550             555             560

Asp Leu Pro Ile Gly Ile Asn Ile Thr Arg Phe Gln Thr Leu Leu Ala
            565             570             575

Leu His Arg Ser Tyr Leu Thr Pro Gly Asp Ser Ser Ser Gly Trp Thr
            580             585             590

Ala Gly Ala Ala Ala Tyr Tyr Val Gly Tyr Leu Gln Pro Arg Thr Phe
        595             600             605
```

```
Leu Leu Lys Tyr Asn Glu Asn Gly Thr Ile Thr Asp Ala Val Asp Cys
    610             615             620

Ala Leu Asp Pro Leu Ser Glu Thr Lys Cys Thr Leu Lys Ser Phe Thr
625             630             635             640

Val Glu Lys Gly Ile Tyr Gln Thr Ser Asn Phe Arg Val Gln Pro Thr
            645             650             655

Glu Ser Ile Val Arg Phe Pro Asn Ile Thr Asn Leu Cys Pro Phe Gly
            660             665             670

Glu Val Phe Asn Ala Thr Arg Phe Ala Ser Val Tyr Ala Trp Asn Arg
            675             680             685

Lys Arg Ile Ser Asn Cys Val Ala Asp Tyr Ser Val Leu Tyr Asn Ser
    690             695             700

Ala Ser Phe Ser Thr Phe Lys Cys Tyr Gly Val Ser Pro Thr Lys Leu
705             710             715             720

Asn Asp Leu Cys Phe Thr Asn Val Tyr Ala Asp Ser Phe Val Ile Arg
            725             730             735

Gly Asp Glu Val Arg Gln Ile Ala Pro Gly Gln Thr Gly Lys Ile Ala
            740             745             750

Asp Tyr Asn Tyr Lys Leu Pro Asp Asp Phe Thr Gly Cys Val Ile Ala
            755             760             765

Trp Asn Ser Asn Asn Leu Asp Ser Lys Val Gly Gly Asn Tyr Asn Tyr
    770             775             780

Leu Tyr Arg Leu Phe Arg Lys Ser Asn Leu Lys Pro Phe Glu Arg Asp
785             790             795             800

Ile Ser Thr Glu Ile Tyr Gln Ala Gly Ser Thr Pro Cys Asn Gly Val
            805             810             815

Glu Gly Phe Asn Cys Tyr Phe Pro Leu Gln Ser Tyr Gly Phe Gln Pro
            820             825             830

Thr Asn Gly Val Gly Tyr Gln Pro Tyr Arg Val Val Val Leu Ser Phe
            835             840             845

Glu Leu Leu His Ala Pro Ala Thr Val Cys Gly Pro Lys Lys Ser Thr
    850             855             860

Asn Leu Val Lys Asn Lys Cys Val Asn Phe Asn Phe Asn Gly Leu Thr
865             870             875             880

Gly Thr Gly Val Leu Thr Glu Ser Asn Lys Lys Phe Leu Pro Phe Gln
            885             890             895

Gln Phe Gly Arg Asp Ile Ala Asp Thr Thr Asp Ala Val Arg Asp Pro
            900             905             910

Gln Thr Leu Glu Ile Leu Asp Ile Thr Pro Cys Ser Phe Gly Gly Val
    915             920             925

Ser Val Ile Thr Pro Gly Thr Asn Thr Ser Asn Gln Val Ala Val Leu
    930             935             940

Tyr Gln Asp Val Asn Cys Thr Glu Val Pro Val Ala Ile His Ala Asp
945             950             955             960

Gln Leu Thr Pro Thr Trp Arg Val Tyr Ser Thr Gly Ser Asn Val Phe
            965             970             975

Gln Thr Arg Ala Gly Cys Leu Ile Gly Ala Glu His Val Asn Asn Ser
            980             985             990

Tyr Glu Cys Asp Ile Pro Ile Gly  Ala Gly Ile Cys Ala  Ser Tyr Gln
            995             1000             1005

Thr Gln  Thr Asn Ser Pro Arg  Arg Ala Arg Ser Val  Ala Ser Gln
    1010             1015             1020

Ser Ile  Ile Ala Tyr Thr Met  Ser Leu Gly Ala Glu  Asn Ser Val
```

-continued

```
      1025                1030                1035

Ala Tyr  Ser Asn Asn Ser Ile  Ala Ile Pro Thr Asn  Phe Thr Ile
      1040                1045                1050

Ser Val  Thr Thr Glu Ile Leu  Pro Val Ser Met Thr  Lys Thr Ser
      1055                1060                1065

Val Asp  Cys Thr Met Tyr Ile  Cys Gly Asp Ser Thr  Glu Cys Ser
      1070                1075                1080

Asn Leu  Leu Leu Gln Tyr Gly  Ser Phe Cys Thr Gln  Leu Asn Arg
      1085                1090                1095

Ala Leu  Thr Gly Ile Ala Val  Glu Gln Asp Lys Asn  Thr Gln Glu
      1100                1105                1110

Val Phe  Ala Gln Val Lys Gln  Ile Tyr Lys Thr Pro  Pro Ile Lys
      1115                1120                1125

Asp Phe  Gly Gly Phe Asn Phe  Ser Gln Ile Leu Pro  Asp Pro Ser
      1130                1135                1140

Lys Pro  Ser Lys Arg Ser Phe  Ile Glu Asp Leu Leu  Phe Asn Lys
      1145                1150                1155

Val Thr  Leu Ala Asp Ala Gly  Phe Ile Lys Gln Tyr  Gly Asp Cys
      1160                1165                1170

Leu Gly  Asp Ile Ala Ala Arg  Asp Leu Ile Cys Ala  Gln Lys Phe
      1175                1180                1185

Asn Gly  Leu Thr Val Leu Pro  Pro Leu Leu Thr Asp  Glu Met Ile
      1190                1195                1200

Ala Gln  Tyr Thr Ser Ala Leu  Leu Ala Gly Thr Ile  Thr Ser Gly
      1205                1210                1215

Trp Thr  Phe Gly Ala Gly Ala  Ala Leu Gln Ile Pro  Phe Ala Met
      1220                1225                1230

Gln Met  Ala Tyr Arg Phe Asn  Gly Ile Gly Val Thr  Gln Asn Val
      1235                1240                1245

Leu Tyr  Glu Asn Gln Lys Leu  Ile Ala Asn Gln Phe  Asn Ser Ala
      1250                1255                1260

Ile Gly  Lys Ile Gln Asp Ser  Leu Ser Ser Thr Ala  Ser Ala Leu
      1265                1270                1275

Gly Lys  Leu Gln Asp Val Val  Asn Gln Asn Ala Gln  Ala Leu Asn
      1280                1285                1290

Thr Leu  Val Lys Gln Leu Ser  Ser Asn Phe Gly Ala  Ile Ser Ser
      1295                1300                1305

Val Leu  Asn Asp Ile Leu Ser  Arg Leu Asp Lys Val  Glu Ala Glu
      1310                1315                1320

Val Gln  Ile Asp Arg Leu Ile  Thr Gly Arg Leu Gln  Ser Leu Gln
      1325                1330                1335

Thr Tyr  Val Thr Gln Gln Leu  Ile Arg Ala Ala Glu  Ile Arg Ala
      1340                1345                1350

Ser Ala  Asn Leu Ala Ala Thr  Lys Met Ser Glu Cys  Val Leu Gly
      1355                1360                1365

Gln Ser  Lys Arg Val Asp Phe  Cys Gly Lys Gly Tyr  His Leu Met
      1370                1375                1380

Ser Phe  Pro Gln Ser Ala Pro  His Gly Val Val Phe  Leu His Val
      1385                1390                1395

Thr Tyr  Val Pro Ala Gln Glu  Lys Asn Phe Thr Thr  Ala Pro Ala
      1400                1405                1410

Ile Cys  His Asp Gly Lys Ala  His Phe Pro Arg Glu  Gly Val Phe
      1415                1420                1425
```

-continued

```
Val Ser Asn Gly Thr His Trp  Phe Val Thr Gln Arg  Asn Phe Tyr
    1430                 1435                 1440

Glu Pro Gln Ile Ile Thr Thr  Asp Asn Thr Phe Val  Ser Gly Asn
    1445                 1450                 1455

Cys Asp Val Val Ile Gly Ile  Val Asn Asn Thr Val  Tyr Asp Pro
    1460                 1465                 1470

Leu Gln Pro Glu Leu Asp Ser  Phe Lys Glu Glu Leu  Asp Lys Tyr
    1475                 1480                 1485

Phe Lys Asn His Thr Ser Pro  Asp Val Asp Leu Gly  Asp Ile Ser
    1490                 1495                 1500

Gly Ile Asn Ala Ser Val Val  Asn Ile Gln Lys Glu  Ile Asp Arg
    1505                 1510                 1515

Leu Asn Glu Val Ala Lys Asn  Leu Asn Glu Ser Leu  Ile Asp Leu
    1520                 1525                 1530

Gln Glu Leu Gly Lys Tyr Glu  Gln Tyr Ile Lys Trp  Pro Trp Tyr
    1535                 1540                 1545

Ile Trp Leu Gly Phe Ile Ala  Gly Leu Ile Ala Ile  Val Met Val
    1550                 1555                 1560

Thr Ile Met Leu Cys Cys Met  Thr Ser Cys Cys Ser  Cys Leu Lys
    1565                 1570                 1575

Gly Cys Cys Ser Cys Gly Ser  Cys Cys Lys Phe Asp  Glu Asp Asp
    1580                 1585                 1590

Ser Glu Pro Val Leu Lys Gly  Val Lys Leu His Tyr  Thr
    1595                 1600                 1605

<210> SEQ ID NO 11
<211> LENGTH: 1594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
```

-continued

```
                 165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
            195                 200                 205

Asp His Ser Ser Ser Ser Asp Asn Ile Ala Leu Leu Val Gln Pro His
        210                 215                 220

Ala Ile Met Gly Val Ala Phe Thr Trp Pro Met Tyr Ser Phe Val Ser
    225                 230                 235                 240

Glu Glu Thr Gly Thr Leu Ile Val Asn Ser Val Leu Leu Phe Leu Ala
                245                 250                 255

Phe Val Val Phe Leu Leu Val Thr Leu Ala Ile Leu Thr Ala Leu Arg
            260                 265                 270

Leu Cys Ala Tyr Cys Cys Asn Ile Val Asn Val Ser Leu Val Lys Pro
            275                 280                 285

Ser Phe Tyr Val Tyr Ser Arg Val Lys Asn Leu Asn Ser Ser Arg Val
        290                 295                 300

Pro Asp Leu Leu Val Pro His Ala Ile Met Gly Val Ala Phe Thr Trp
    305                 310                 315                 320

Pro Met Phe Val Phe Leu Val Leu Leu Pro Leu Val Ser Ser Gln Cys
                325                 330                 335

Val Asn Leu Thr Thr Arg Thr Gln Leu Pro Pro Ala Tyr Thr Asn Ser
            340                 345                 350

Phe Thr Arg Gly Val Tyr Tyr Pro Asp Lys Val Phe Arg Ser Ser Val
            355                 360                 365

Leu His Ser Thr Gln Asp Leu Phe Leu Pro Phe Phe Ser Asn Val Thr
        370                 375                 380

Trp Phe His Ala Ile His Val Ser Gly Thr Asn Gly Thr Lys Arg Phe
    385                 390                 395                 400

Asp Asn Pro Val Leu Pro Phe Asn Asp Gly Val Tyr Phe Ala Ser Thr
            405                 410                 415

Glu Lys Ser Asn Ile Ile Arg Gly Trp Ile Phe Gly Thr Thr Leu Asp
            420                 425                 430

Ser Lys Thr Gln Ser Leu Leu Ile Val Asn Asn Ala Thr Asn Val Val
        435                 440                 445

Ile Lys Val Cys Glu Phe Gln Phe Cys Asn Asp Pro Phe Leu Gly Val
        450                 455                 460

Tyr Tyr His Lys Asn Asn Lys Ser Trp Met Glu Ser Glu Phe Arg Val
    465                 470                 475                 480

Tyr Ser Ser Ala Asn Asn Cys Thr Phe Glu Tyr Val Ser Gln Pro Phe
            485                 490                 495

Leu Met Asp Leu Glu Gly Lys Gln Gly Asn Phe Lys Asn Leu Arg Glu
            500                 505                 510

Phe Val Phe Lys Asn Ile Asp Gly Tyr Phe Lys Ile Tyr Ser Lys His
            515                 520                 525

Thr Pro Ile Asn Leu Val Arg Asp Leu Pro Gln Gly Phe Ser Ala Leu
        530                 535                 540

Glu Pro Leu Val Asp Leu Pro Ile Gly Ile Asn Ile Thr Arg Phe Gln
    545                 550                 555                 560

Thr Leu Leu Ala Leu His Arg Ser Tyr Leu Thr Pro Gly Asp Ser Ser
            565                 570                 575

Ser Gly Trp Thr Ala Gly Ala Ala Ala Tyr Tyr Val Gly Tyr Leu Gln
            580                 585                 590
```

```
Pro Arg Thr Phe Leu Leu Lys Tyr Asn Glu Asn Gly Thr Ile Thr Asp
    595                 600             605

Ala Val Asp Cys Ala Leu Asp Pro Leu Ser Glu Thr Lys Cys Thr Leu
    610                 615             620

Lys Ser Phe Thr Val Glu Lys Gly Ile Tyr Gln Thr Ser Asn Phe Arg
625                 630             635                 640

Val Gln Pro Thr Glu Ser Ile Val Arg Phe Pro Asn Ile Thr Asn Leu
            645             650             655

Cys Pro Phe Gly Glu Val Phe Asn Ala Thr Arg Phe Ala Ser Val Tyr
            660             665             670

Ala Trp Asn Arg Lys Arg Ile Ser Asn Cys Val Ala Asp Tyr Ser Val
    675                 680             685

Leu Tyr Asn Ser Ala Ser Phe Ser Thr Phe Lys Cys Tyr Gly Val Ser
    690                 695             700

Pro Thr Lys Leu Asn Asp Leu Cys Phe Thr Asn Val Tyr Ala Asp Ser
705                 710             715                 720

Phe Val Ile Arg Gly Asp Glu Val Arg Gln Ile Ala Pro Gly Gln Thr
            725             730             735

Gly Lys Ile Ala Asp Tyr Asn Tyr Lys Leu Pro Asp Asp Phe Thr Gly
            740             745             750

Cys Val Ile Ala Trp Asn Ser Asn Asn Leu Asp Ser Lys Val Gly Gly
            755             760             765

Asn Tyr Asn Tyr Leu Tyr Arg Leu Phe Arg Lys Ser Asn Leu Lys Pro
    770             775             780

Phe Glu Arg Asp Ile Ser Thr Glu Ile Tyr Gln Ala Gly Ser Thr Pro
785                 790             795                 800

Cys Asn Gly Val Glu Gly Phe Asn Cys Tyr Phe Pro Leu Gln Ser Tyr
            805             810             815

Gly Phe Gln Pro Thr Asn Gly Val Gly Tyr Gln Pro Tyr Arg Val Val
            820             825             830

Val Leu Ser Phe Glu Leu Leu His Ala Pro Ala Thr Val Cys Gly Pro
    835             840             845

Lys Lys Ser Thr Asn Leu Val Lys Asn Lys Cys Val Asn Phe Asn Phe
    850                 855             860

Asn Gly Leu Thr Gly Thr Gly Val Leu Thr Glu Ser Asn Lys Lys Phe
865                 870             875                 880

Leu Pro Phe Gln Gln Phe Gly Arg Asp Ile Ala Asp Thr Thr Asp Ala
            885             890             895

Val Arg Asp Pro Gln Thr Leu Glu Ile Leu Asp Ile Thr Pro Cys Ser
            900             905             910

Phe Gly Gly Val Ser Val Ile Thr Pro Gly Thr Asn Thr Ser Asn Gln
            915             920             925

Val Ala Val Leu Tyr Gln Asp Val Asn Cys Thr Glu Val Pro Val Ala
    930             935             940

Ile His Ala Asp Gln Leu Thr Pro Thr Trp Arg Val Tyr Ser Thr Gly
945                 950             955                 960

Ser Asn Val Phe Gln Thr Arg Ala Gly Cys Leu Ile Gly Ala Glu His
            965             970             975

Val Asn Asn Ser Tyr Glu Cys Asp Ile Pro Ile Gly Ala Gly Ile Cys
            980             985             990

Ala Ser Tyr Gln Thr Gln Thr Asn  Ser Pro Arg Arg Ala  Arg Ser Val
    995             1000                 1005
```

-continued

Ala Ser  Gln Ser Ile Ile Ala  Tyr Thr Met Ser Leu  Gly Ala Glu
    1010              1015              1020

Asn Ser  Val Ala Tyr Ser Asn  Asn Ser Ile Ala Ile  Pro Thr Asn
    1025              1030              1035

Phe Thr  Ile Ser Val Thr Thr  Glu Ile Leu Pro Val  Ser Met Thr
    1040              1045              1050

Lys Thr  Ser Val Asp Cys Thr  Met Tyr Ile Cys Gly  Asp Ser Thr
    1055              1060              1065

Glu Cys  Ser Asn Leu Leu Leu  Gln Tyr Gly Ser Phe  Cys Thr Gln
    1070              1075              1080

Leu Asn  Arg Ala Leu Thr Gly  Ile Ala Val Glu Gln  Asp Lys Asn
    1085              1090              1095

Thr Gln  Glu Val Phe Ala Gln  Val Lys Gln Ile Tyr  Lys Thr Pro
    1100              1105              1110

Pro Ile  Lys Asp Phe Gly Gly  Phe Asn Phe Ser Gln  Ile Leu Pro
    1115              1120              1125

Asp Pro  Ser Lys Pro Ser Lys  Arg Ser Phe Ile Glu  Asp Leu Leu
    1130              1135              1140

Phe Asn  Lys Val Thr Leu Ala  Asp Ala Gly Phe Ile  Lys Gln Tyr
    1145              1150              1155

Gly Asp  Cys Leu Gly Asp Ile  Ala Ala Arg Asp Leu  Ile Cys Ala
    1160              1165              1170

Gln Lys  Phe Asn Gly Leu Thr  Val Leu Pro Pro Leu  Leu Thr Asp
    1175              1180              1185

Glu Met  Ile Ala Gln Tyr Thr  Ser Ala Leu Leu Ala  Gly Thr Ile
    1190              1195              1200

Thr Ser  Gly Trp Thr Phe Gly  Ala Gly Ala Ala Leu  Gln Ile Pro
    1205              1210              1215

Phe Ala  Met Gln Met Ala Tyr  Arg Phe Asn Gly Ile  Gly Val Thr
    1220              1225              1230

Gln Asn  Val Leu Tyr Glu Asn  Gln Lys Leu Ile Ala  Asn Gln Phe
    1235              1240              1245

Asn Ser  Ala Ile Gly Lys Ile  Gln Asp Ser Leu Ser  Ser Thr Ala
    1250              1255              1260

Ser Ala  Leu Gly Lys Leu Gln  Asp Val Val Asn Gln  Asn Ala Gln
    1265              1270              1275

Ala Leu  Asn Thr Leu Val Lys  Gln Leu Ser Ser Asn  Phe Gly Ala
    1280              1285              1290

Ile Ser  Ser Val Leu Asn Asp  Ile Leu Ser Arg Leu  Asp Lys Val
    1295              1300              1305

Glu Ala  Glu Val Gln Ile Asp  Arg Leu Ile Thr Gly  Arg Leu Gln
    1310              1315              1320

Ser Leu  Gln Thr Tyr Val Thr  Gln Gln Leu Ile Arg  Ala Ala Glu
    1325              1330              1335

Ile Arg  Ala Ser Ala Asn Leu  Ala Ala Thr Lys Met  Ser Glu Cys
    1340              1345              1350

Val Leu  Gly Gln Ser Lys Arg  Val Asp Phe Cys Gly  Lys Gly Tyr
    1355              1360              1365

His Leu  Met Ser Phe Pro Gln  Ser Ala Pro His Gly  Val Val Phe
    1370              1375              1380

Leu His  Val Thr Tyr Val Pro  Ala Gln Glu Lys Asn  Phe Thr Thr
    1385              1390              1395

Ala Pro  Ala Ile Cys His Asp  Gly Lys Ala His Phe  Pro Arg Glu

-continued

```
             1400                1405                1410

Gly Val  Phe Val Ser Asn Gly  Thr His Trp Phe Val  Thr Gln Arg
    1415                1420                1425

Asn Phe  Tyr Glu Pro Gln Ile  Ile Thr Thr Asp Asn  Thr Phe Val
    1430                1435                1440

Ser Gly  Asn Cys Asp Val Val  Ile Gly Ile Val Asn  Asn Thr Val
    1445                1450                1455

Tyr Asp  Pro Leu Gln Pro Glu  Leu Asp Ser Phe Lys  Glu Glu Leu
    1460                1465                1470

Asp Lys  Tyr Phe Lys Asn His  Thr Ser Pro Asp Val  Asp Leu Gly
    1475                1480                1485

Asp Ile  Ser Gly Ile Asn Ala  Ser Val Val Asn Ile  Gln Lys Glu
    1490                1495                1500

Ile Asp  Arg Leu Asn Glu Val  Ala Lys Asn Leu Asn  Glu Ser Leu
    1505                1510                1515

Ile Asp  Leu Gln Glu Leu Gly  Lys Tyr Glu Gln Tyr  Ile Lys Trp
    1520                1525                1530

Pro Trp  Tyr Ile Trp Leu Gly  Phe Ile Ala Gly Leu  Ile Ala Ile
    1535                1540                1545

Val Met  Val Thr Ile Met Leu  Cys Cys Met Thr Ser  Cys Cys Ser
    1550                1555                1560

Cys Leu  Lys Gly Cys Cys Ser  Cys Gly Ser Cys Cys  Lys Phe Asp
    1565                1570                1575

Glu Asp  Asp Ser Glu Pro Val  Leu Lys Gly Val Lys  Leu His Tyr
    1580                1585                1590

Thr

<210> SEQ ID NO 12
<211> LENGTH: 1606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
            115                 120                 125

Leu Thr Arg Pro Leu Leu Glu Ser Glu Leu Val Ile Gly Ala Val Ile
        130                 135                 140

Leu Arg Gly His Leu Arg Ile Ala Gly His His Leu Gly Arg Cys Asp
```

```
145              150              155              160

Ile Lys Asp Leu Pro Lys Glu Ile Thr Val Ala Thr Ser Arg Thr Leu
             165              170              175

Ser Tyr Tyr Lys Leu Gly Ala Ser Gln Arg Val Ala Gly Asp Ser Gly
             180              185              190

Phe Ala Ala Tyr Ser Arg Tyr Arg Ile Gly Asn Tyr Lys Leu Asn Thr
             195              200              205

Asp His Ser Ser Ser Ser Asp Asn Ile Ala Leu Leu Val Gln Pro His
             210              215              220

Ala Ile Met Gly Val Ala Phe Thr Trp Val Met Ala Leu Ala Cys Ala
225              230              235              240

Ala Pro Pro Leu Val Pro Met Tyr Ser Phe Val Ser Glu Glu Thr Gly
             245              250              255

Thr Leu Ile Val Asn Ser Val Leu Leu Phe Leu Ala Phe Val Val Phe
             260              265              270

Leu Leu Val Thr Leu Ala Ile Leu Thr Ala Leu Arg Leu Cys Ala Tyr
             275              280              285

Cys Cys Asn Ile Val Asn Val Ser Leu Val Lys Pro Ser Phe Tyr Val
290              295              300

Tyr Ser Arg Val Lys Asn Leu Asn Ser Ser Arg Val Pro Asp Leu Leu
305              310              315              320

Val Pro His Ala Ile Met Gly Val Ala Phe Thr Trp Pro Met Phe Val
             325              330              335

Phe Leu Val Leu Leu Pro Leu Val Ser Ser Gln Cys Val Asn Leu Thr
             340              345              350

Thr Arg Thr Gln Leu Pro Pro Ala Tyr Thr Asn Ser Phe Thr Arg Gly
             355              360              365

Val Tyr Tyr Pro Asp Lys Val Phe Arg Ser Ser Val Leu His Ser Thr
             370              375              380

Gln Asp Leu Phe Leu Pro Phe Phe Ser Asn Val Thr Trp Phe His Ala
385              390              395              400

Ile His Val Ser Gly Thr Asn Gly Thr Lys Arg Phe Asp Asn Pro Val
             405              410              415

Leu Pro Phe Asn Asp Gly Val Tyr Phe Ala Ser Thr Glu Lys Ser Asn
             420              425              430

Ile Ile Arg Gly Trp Ile Phe Gly Thr Thr Leu Asp Ser Lys Thr Gln
             435              440              445

Ser Leu Leu Ile Val Asn Asn Ala Thr Asn Val Val Ile Lys Val Cys
             450              455              460

Glu Phe Gln Phe Cys Asn Asp Pro Phe Leu Gly Val Tyr Tyr His Lys
465              470              475              480

Asn Asn Lys Ser Trp Met Glu Ser Glu Phe Arg Val Tyr Ser Ser Ala
             485              490              495

Asn Asn Cys Thr Phe Glu Tyr Val Ser Gln Pro Phe Leu Met Asp Leu
             500              505              510

Glu Gly Lys Gln Gly Asn Phe Lys Asn Leu Arg Glu Phe Val Phe Lys
             515              520              525

Asn Ile Asp Gly Tyr Phe Lys Ile Tyr Ser Lys His Thr Pro Ile Asn
             530              535              540

Leu Val Arg Asp Leu Pro Gln Gly Phe Ser Ala Leu Glu Pro Leu Val
545              550              555              560

Asp Leu Pro Ile Gly Ile Asn Ile Thr Arg Phe Gln Thr Leu Leu Ala
             565              570              575
```

-continued

```
Leu His Arg Ser Tyr Leu Thr Pro Gly Asp Ser Ser Ser Gly Trp Thr
            580                 585             590

Ala Gly Ala Ala Ala Tyr Tyr Val Gly Tyr Leu Gln Pro Arg Thr Phe
            595                 600             605

Leu Leu Lys Tyr Asn Glu Asn Gly Thr Ile Thr Asp Ala Val Asp Cys
            610                 615             620

Ala Leu Asp Pro Leu Ser Glu Thr Lys Cys Thr Leu Lys Ser Phe Thr
625                 630                 635                 640

Val Glu Lys Gly Ile Tyr Gln Thr Ser Asn Phe Arg Val Gln Pro Thr
                645                 650             655

Glu Ser Ile Val Arg Phe Pro Asn Ile Thr Asn Leu Cys Pro Phe Gly
                660                 665             670

Glu Val Phe Asn Ala Thr Arg Phe Ala Ser Val Tyr Ala Trp Asn Arg
            675                 680             685

Lys Arg Ile Ser Asn Cys Val Ala Asp Tyr Ser Val Leu Tyr Asn Ser
            690                 695             700

Ala Ser Phe Ser Thr Phe Lys Cys Tyr Gly Val Ser Pro Thr Lys Leu
705                 710                 715                 720

Asn Asp Leu Cys Phe Thr Asn Val Tyr Ala Asp Ser Phe Val Ile Arg
                725                 730                 735

Gly Asp Glu Val Arg Gln Ile Ala Pro Gly Gln Thr Gly Lys Ile Ala
                740                 745                 750

Asp Tyr Asn Tyr Lys Leu Pro Asp Asp Phe Thr Gly Cys Val Ile Ala
            755                 760                 765

Trp Asn Ser Asn Asn Leu Asp Ser Lys Val Gly Gly Asn Tyr Asn Tyr
770                 775                 780

Leu Tyr Arg Leu Phe Arg Lys Ser Asn Leu Lys Pro Phe Glu Arg Asp
785                 790                 795                 800

Ile Ser Thr Glu Ile Tyr Gln Ala Gly Ser Thr Pro Cys Asn Gly Val
                805                 810                 815

Glu Gly Phe Asn Cys Tyr Phe Pro Leu Gln Ser Tyr Gly Phe Gln Pro
            820                 825                 830

Thr Asn Gly Val Gly Tyr Gln Pro Tyr Arg Val Val Val Leu Ser Phe
            835                 840                 845

Glu Leu Leu His Ala Pro Ala Thr Val Cys Gly Pro Lys Lys Ser Thr
850                 855                 860

Asn Leu Val Lys Asn Lys Cys Val Asn Phe Asn Phe Asn Gly Leu Thr
865                 870                 875                 880

Gly Thr Gly Val Leu Thr Glu Ser Asn Lys Lys Phe Leu Pro Phe Gln
                885                 890                 895

Gln Phe Gly Arg Asp Ile Ala Asp Thr Thr Asp Ala Val Arg Asp Pro
            900                 905                 910

Gln Thr Leu Glu Ile Leu Asp Ile Thr Pro Cys Ser Phe Gly Gly Val
            915                 920                 925

Ser Val Ile Thr Pro Gly Thr Asn Thr Ser Asn Gln Val Ala Val Leu
            930                 935                 940

Tyr Gln Asp Val Asn Cys Thr Glu Val Pro Val Ala Ile His Ala Asp
945                 950                 955                 960

Gln Leu Thr Pro Thr Trp Arg Val Tyr Ser Thr Gly Ser Asn Val Phe
                965                 970                 975

Gln Thr Arg Ala Gly Cys Leu Ile Gly Ala Glu His Val Asn Asn Ser
            980                 985                 990
```

-continued

```
Tyr Glu Cys Asp Ile Pro Ile Gly  Ala Gly Ile Cys Ala  Ser Tyr Gln
        995              1000              1005

Thr Gln  Thr Asn Ser Pro Arg  Arg Ala Arg Ser Val  Ala Ser Gln
    1010              1015              1020

Ser Ile  Ile Ala Tyr Thr Met  Ser Leu Gly Ala Glu  Asn Ser Val
    1025              1030              1035

Ala Tyr  Ser Asn Asn Ser Ile  Ala Ile Pro Thr Asn  Phe Thr Ile
    1040              1045              1050

Ser Val  Thr Thr Glu Ile Leu  Pro Val Ser Met Thr  Lys Thr Ser
    1055              1060              1065

Val Asp  Cys Thr Met Tyr Ile  Cys Gly Asp Ser Thr  Glu Cys Ser
    1070              1075              1080

Asn Leu  Leu Leu Gln Tyr Gly  Ser Phe Cys Thr Gln  Leu Asn Arg
    1085              1090              1095

Ala Leu  Thr Gly Ile Ala Val  Glu Gln Asp Lys Asn  Thr Gln Glu
    1100              1105              1110

Val Phe  Ala Gln Val Lys Gln  Ile Tyr Lys Thr Pro  Pro Ile Lys
    1115              1120              1125

Asp Phe  Gly Gly Phe Asn Phe  Ser Gln Ile Leu Pro  Asp Pro Ser
    1130              1135              1140

Lys Pro  Ser Lys Arg Ser Phe  Ile Glu Asp Leu Leu  Phe Asn Lys
    1145              1150              1155

Val Thr  Leu Ala Asp Ala Gly  Phe Ile Lys Gln Tyr  Gly Asp Cys
    1160              1165              1170

Leu Gly  Asp Ile Ala Ala Arg  Asp Leu Ile Cys Ala  Gln Lys Phe
    1175              1180              1185

Asn Gly  Leu Thr Val Leu Pro  Pro Leu Leu Thr Asp  Glu Met Ile
    1190              1195              1200

Ala Gln  Tyr Thr Ser Ala Leu  Leu Ala Gly Thr Ile  Thr Ser Gly
    1205              1210              1215

Trp Thr  Phe Gly Ala Gly Ala  Ala Leu Gln Ile Pro  Phe Ala Met
    1220              1225              1230

Gln Met  Ala Tyr Arg Phe Asn  Gly Ile Gly Val Thr  Gln Asn Val
    1235              1240              1245

Leu Tyr  Glu Asn Gln Lys Leu  Ile Ala Asn Gln Phe  Asn Ser Ala
    1250              1255              1260

Ile Gly  Lys Ile Gln Asp Ser  Leu Ser Ser Thr Ala  Ser Ala Leu
    1265              1270              1275

Gly Lys  Leu Gln Asp Val Val  Asn Gln Asn Ala Gln  Ala Leu Asn
    1280              1285              1290

Thr Leu  Val Lys Gln Leu Ser  Ser Asn Phe Gly Ala  Ile Ser Ser
    1295              1300              1305

Val Leu  Asn Asp Ile Leu Ser  Arg Leu Asp Lys Val  Glu Ala Glu
    1310              1315              1320

Val Gln  Ile Asp Arg Leu Ile  Thr Gly Arg Leu Gln  Ser Leu Gln
    1325              1330              1335

Thr Tyr  Val Thr Gln Gln Leu  Ile Arg Ala Ala Glu  Ile Arg Ala
    1340              1345              1350

Ser Ala  Asn Leu Ala Ala Thr  Lys Met Ser Glu Cys  Val Leu Gly
    1355              1360              1365

Gln Ser  Lys Arg Val Asp Phe  Cys Gly Lys Gly Tyr  His Leu Met
    1370              1375              1380

Ser Phe  Pro Gln Ser Ala Pro  His Gly Val Val Phe  Leu His Val
```

-continued

```
        1385                1390                1395

Thr Tyr  Val Pro Ala Gln Glu  Lys Asn Phe Thr Thr  Ala Pro Ala
    1400                1405                1410

Ile Cys  His Asp Gly Lys Ala  His Phe Pro Arg Glu  Gly Val Phe
    1415                1420                1425

Val Ser  Asn Gly Thr His Trp  Phe Val Thr Gln Arg  Asn Phe Tyr
    1430                1435                1440

Glu Pro  Gln Ile Ile Thr Thr  Asp Asn Thr Phe Val  Ser Gly Asn
    1445                1450                1455

Cys Asp  Val Val Ile Gly Ile  Val Asn Asn Thr Val  Tyr Asp Pro
    1460                1465                1470

Leu Gln  Pro Glu Leu Asp Ser  Phe Lys Glu Glu Leu  Asp Lys Tyr
    1475                1480                1485

Phe Lys  Asn His Thr Ser Pro  Asp Val Asp Leu Gly  Asp Ile Ser
    1490                1495                1500

Gly Ile  Asn Ala Ser Val Val  Asn Ile Gln Lys Glu  Ile Asp Arg
    1505                1510                1515

Leu Asn  Glu Val Ala Lys Asn  Leu Asn Glu Ser Leu  Ile Asp Leu
    1520                1525                1530

Gln Glu  Leu Gly Lys Tyr Glu  Gln Tyr Ile Lys Trp  Pro Trp Tyr
    1535                1540                1545

Ile Trp  Leu Gly Phe Ile Ala  Gly Leu Ile Ala Ile  Val Met Val
    1550                1555                1560

Thr Ile  Met Leu Cys Cys Met  Thr Ser Cys Cys Ser  Cys Leu Lys
    1565                1570                1575

Gly Cys  Cys Ser Cys Gly Ser  Cys Cys Lys Phe Asp  Glu Asp Asp
    1580                1585                1590

Ser Glu  Pro Val Leu Lys Gly  Val Lys Leu His Tyr  Thr
    1595                1600                1605
```

<210> SEQ ID NO 13
<211> LENGTH: 1618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125
```

-continued

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
                180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala Leu Leu Val Gln Pro His
    210                 215                 220

Ala Ile Met Gly Val Ala Phe Thr Trp Val Met Ala Leu Ala Cys Ala
225                 230                 235                 240

Ala Pro Pro Leu Val Pro Met Tyr Ser Phe Val Ser Glu Glu Thr Gly
                245                 250                 255

Thr Leu Ile Val Asn Ser Val Leu Leu Phe Leu Ala Phe Val Val Phe
        260                 265                 270

Leu Leu Val Thr Leu Ala Ile Leu Thr Ala Leu Arg Leu Cys Ala Tyr
        275                 280                 285

Cys Cys Asn Ile Val Asn Val Ser Leu Val Lys Pro Ser Phe Tyr Val
    290                 295                 300

Tyr Ser Arg Val Lys Asn Leu Asn Ser Ser Arg Val Pro Asp Leu Leu
305                 310                 315                 320

Val Pro His Ala Ile Met Gly Val Ala Phe Thr Trp Val Met Ala Leu
                325                 330                 335

Ala Cys Ala Ala Pro Pro Leu Val Pro Met Phe Val Phe Leu Val Leu
        340                 345                 350

Leu Pro Leu Val Ser Ser Gln Cys Val Asn Leu Thr Thr Arg Thr Gln
        355                 360                 365

Leu Pro Pro Ala Tyr Thr Asn Ser Phe Thr Arg Gly Val Tyr Tyr Pro
    370                 375                 380

Asp Lys Val Phe Arg Ser Ser Val Leu His Ser Thr Gln Asp Leu Phe
385                 390                 395                 400

Leu Pro Phe Phe Ser Asn Val Thr Trp Phe His Ala Ile His Val Ser
                405                 410                 415

Gly Thr Asn Gly Thr Lys Arg Phe Asp Asn Pro Val Leu Pro Phe Asn
                420                 425                 430

Asp Gly Val Tyr Phe Ala Ser Thr Glu Lys Ser Asn Ile Ile Arg Gly
        435                 440                 445

Trp Ile Phe Gly Thr Thr Leu Asp Ser Lys Thr Gln Ser Leu Leu Ile
    450                 455                 460

Val Asn Asn Ala Thr Asn Val Val Ile Lys Val Cys Glu Phe Gln Phe
465                 470                 475                 480

Cys Asn Asp Pro Phe Leu Gly Val Tyr Tyr His Lys Asn Asn Lys Ser
                485                 490                 495

Trp Met Glu Ser Glu Phe Arg Val Tyr Ser Ser Ala Asn Asn Cys Thr
                500                 505                 510

Phe Glu Tyr Val Ser Gln Pro Phe Leu Met Asp Leu Glu Gly Lys Gln
                515                 520                 525

Gly Asn Phe Lys Asn Leu Arg Glu Phe Val Phe Lys Asn Ile Asp Gly
        530                 535                 540

Tyr Phe Lys Ile Tyr Ser Lys His Thr Pro Ile Asn Leu Val Arg Asp

```
545                 550                 555                 560

Leu Pro Gln Gly Phe Ser Ala Leu Glu Pro Leu Val Asp Leu Pro Ile
                565                 570                 575

Gly Ile Asn Ile Thr Arg Phe Gln Thr Leu Leu Ala Leu His Arg Ser
                580                 585                 590

Tyr Leu Thr Pro Gly Asp Ser Ser Gly Trp Thr Ala Gly Ala Ala
                595                 600                 605

Ala Tyr Tyr Val Gly Tyr Leu Gln Pro Arg Thr Phe Leu Leu Lys Tyr
                610                 615                 620

Asn Glu Asn Gly Thr Ile Thr Asp Ala Val Asp Cys Ala Leu Asp Pro
625                 630                 635                 640

Leu Ser Glu Thr Lys Cys Thr Leu Lys Ser Phe Thr Val Glu Lys Gly
                645                 650                 655

Ile Tyr Gln Thr Ser Asn Phe Arg Val Gln Pro Thr Glu Ser Ile Val
                660                 665                 670

Arg Phe Pro Asn Ile Thr Asn Leu Cys Pro Phe Gly Glu Val Phe Asn
                675                 680                 685

Ala Thr Arg Phe Ala Ser Val Tyr Ala Trp Asn Arg Lys Arg Ile Ser
                690                 695                 700

Asn Cys Val Ala Asp Tyr Ser Val Leu Tyr Asn Ser Ala Ser Phe Ser
705                 710                 715                 720

Thr Phe Lys Cys Tyr Gly Val Ser Pro Thr Lys Leu Asn Asp Leu Cys
                725                 730                 735

Phe Thr Asn Val Tyr Ala Asp Ser Phe Val Ile Arg Gly Asp Glu Val
                740                 745                 750

Arg Gln Ile Ala Pro Gly Gln Thr Gly Lys Ile Ala Asp Tyr Asn Tyr
                755                 760                 765

Lys Leu Pro Asp Asp Phe Thr Gly Cys Val Ile Ala Trp Asn Ser Asn
                770                 775                 780

Asn Leu Asp Ser Lys Val Gly Gly Asn Tyr Asn Tyr Leu Tyr Arg Leu
785                 790                 795                 800

Phe Arg Lys Ser Asn Leu Lys Pro Phe Glu Arg Asp Ile Ser Thr Glu
                805                 810                 815

Ile Tyr Gln Ala Gly Ser Thr Pro Cys Asn Gly Val Glu Gly Phe Asn
                820                 825                 830

Cys Tyr Phe Pro Leu Gln Ser Tyr Gly Phe Gln Pro Thr Asn Gly Val
                835                 840                 845

Gly Tyr Gln Pro Tyr Arg Val Val Val Leu Ser Phe Glu Leu Leu His
                850                 855                 860

Ala Pro Ala Thr Val Cys Gly Pro Lys Lys Ser Thr Asn Leu Val Lys
865                 870                 875                 880

Asn Lys Cys Val Asn Phe Asn Phe Asn Gly Leu Thr Gly Thr Gly Val
                885                 890                 895

Leu Thr Glu Ser Asn Lys Lys Phe Leu Pro Phe Gln Gln Phe Gly Arg
                900                 905                 910

Asp Ile Ala Asp Thr Thr Asp Ala Val Arg Asp Pro Gln Thr Leu Glu
                915                 920                 925

Ile Leu Asp Ile Thr Pro Cys Ser Phe Gly Gly Val Ser Val Ile Thr
                930                 935                 940

Pro Gly Thr Asn Thr Ser Asn Gln Val Ala Val Leu Tyr Gln Asp Val
945                 950                 955                 960

Asn Cys Thr Glu Val Pro Val Ala Ile His Ala Asp Gln Leu Thr Pro
                965                 970                 975
```

```
Thr Trp Arg Val Tyr Ser Thr Gly Ser Asn Val Phe Gln Thr Arg Ala
            980                 985                 990

Gly Cys Leu Ile Gly Ala Glu His  Val Asn Asn Ser Tyr  Glu Cys Asp
        995             1000                1005

Ile Pro  Ile Gly Ala Gly Ile  Cys Ala Ser Tyr Gln  Thr Gln Thr
1010                1015                1020

Asn Ser  Pro Arg Arg Ala Arg  Ser Val Ala Ser Gln  Ser Ile Ile
1025                1030                1035

Ala Tyr  Thr Met Ser Leu Gly  Ala Glu Asn Ser Val  Ala Tyr Ser
1040                1045                1050

Asn Asn  Ser Ile Ala Ile Pro  Thr Asn Phe Thr Ile  Ser Val Thr
1055                1060                1065

Thr Glu  Ile Leu Pro Val Ser  Met Thr Lys Thr Ser  Val Asp Cys
1070                1075                1080

Thr Met  Tyr Ile Cys Gly Asp  Ser Thr Glu Cys Ser  Asn Leu Leu
1085                1090                1095

Leu Gln  Tyr Gly Ser Phe Cys  Thr Gln Leu Asn Arg  Ala Leu Thr
1100                1105                1110

Gly Ile  Ala Val Glu Gln Asp  Lys Asn Thr Gln Glu  Val Phe Ala
1115                1120                1125

Gln Val  Lys Gln Ile Tyr Lys  Thr Pro Pro Ile Lys  Asp Phe Gly
1130                1135                1140

Gly Phe  Asn Phe Ser Gln Ile  Leu Pro Asp Pro Ser  Lys Pro Ser
1145                1150                1155

Lys Arg  Ser Phe Ile Glu Asp  Leu Leu Phe Asn Lys  Val Thr Leu
1160                1165                1170

Ala Asp  Ala Gly Phe Ile Lys  Gln Tyr Gly Asp Cys  Leu Gly Asp
1175                1180                1185

Ile Ala  Ala Arg Asp Leu Ile  Cys Ala Gln Lys Phe  Asn Gly Leu
1190                1195                1200

Thr Val  Leu Pro Pro Leu Leu  Thr Asp Glu Met Ile  Ala Gln Tyr
1205                1210                1215

Thr Ser  Ala Leu Leu Ala Gly  Thr Ile Thr Ser Gly  Trp Thr Phe
1220                1225                1230

Gly Ala  Gly Ala Ala Leu Gln  Ile Pro Phe Ala Met  Gln Met Ala
1235                1240                1245

Tyr Arg  Phe Asn Gly Ile Gly  Val Thr Gln Asn Val  Leu Tyr Glu
1250                1255                1260

Asn Gln  Lys Leu Ile Ala Asn  Gln Phe Asn Ser Ala  Ile Gly Lys
1265                1270                1275

Ile Gln  Asp Ser Leu Ser Ser  Thr Ala Ser Ala Leu  Gly Lys Leu
1280                1285                1290

Gln Asp  Val Val Asn Gln Asn  Ala Gln Ala Leu Asn  Thr Leu Val
1295                1300                1305

Lys Gln  Leu Ser Ser Asn Phe  Gly Ala Ile Ser Ser  Val Leu Asn
1310                1315                1320

Asp Ile  Leu Ser Arg Leu Asp  Lys Val Glu Ala Glu  Val Gln Ile
1325                1330                1335

Asp Arg  Leu Ile Thr Gly Arg  Leu Gln Ser Leu Gln  Thr Tyr Val
1340                1345                1350

Thr Gln  Gln Leu Ile Arg Ala  Ala Glu Ile Arg Ala  Ser Ala Asn
1355                1360                1365
```

-continued

```
Leu Ala  Ala Thr Lys Met Ser  Glu Cys Val Leu Gly  Gln Ser Lys
    1370             1375             1380

Arg Val  Asp Phe Cys Gly Lys  Gly Tyr His Leu Met  Ser Phe Pro
    1385             1390             1395

Gln Ser  Ala Pro His Gly Val  Val Phe Leu His Val  Thr Tyr Val
    1400             1405             1410

Pro Ala  Gln Glu Lys Asn Phe  Thr Thr Ala Pro Ala  Ile Cys His
    1415             1420             1425

Asp Gly  Lys Ala His Phe Pro  Arg Glu Gly Val Phe  Val Ser Asn
    1430             1435             1440

Gly Thr  His Trp Phe Val Thr  Gln Arg Asn Phe Tyr  Glu Pro Gln
    1445             1450             1455

Ile Ile  Thr Thr Asp Asn Thr  Phe Val Ser Gly Asn  Cys Asp Val
    1460             1465             1470

Val Ile  Gly Ile Val Asn Asn  Thr Val Tyr Asp Pro  Leu Gln Pro
    1475             1480             1485

Glu Leu  Asp Ser Phe Lys Glu  Glu Leu Asp Lys Tyr  Phe Lys Asn
    1490             1495             1500

His Thr  Ser Pro Asp Val Asp  Leu Gly Asp Ile Ser  Gly Ile Asn
    1505             1510             1515

Ala Ser  Val Val Asn Ile Gln  Lys Glu Ile Asp Arg  Leu Asn Glu
    1520             1525             1530

Val Ala  Lys Asn Leu Asn Glu  Ser Leu Ile Asp Leu  Gln Glu Leu
    1535             1540             1545

Gly Lys  Tyr Glu Gln Tyr Ile  Lys Trp Pro Trp Tyr  Ile Trp Leu
    1550             1555             1560

Gly Phe  Ile Ala Gly Leu Ile  Ala Ile Val Met Val  Thr Ile Met
    1565             1570             1575

Leu Cys  Cys Met Thr Ser Cys  Cys Ser Cys Leu Lys  Gly Cys Cys
    1580             1585             1590

Ser Cys  Gly Ser Cys Cys Lys  Phe Asp Glu Asp Asp  Ser Glu Pro
    1595             1600             1605

Val Leu  Lys Gly Val Lys Leu  His Tyr Thr
    1610             1615
```

```
<210> SEQ ID NO 14
<211> LENGTH: 822
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95
```

Phe Thr Gly Cys Val Ile Ala Trp Asn Ser Asn Asn Leu Asp Ser Lys
            100                 105                 110

Val Gly Gly Asn Tyr Asn Tyr Leu Tyr Arg Leu Phe Arg Lys Ser Asn
            115                 120                 125

Leu Lys Pro Phe Glu Arg Asp Ile Ser Thr Glu Ile Tyr Gln Ala Gly
        130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
                180                 185                 190

Cys Gly Pro Pro Thr Ile Lys Pro Ser Pro Pro Ser Lys Ser Pro Ala
            195                 200                 205

Pro Thr Asn Leu Cys Pro Phe Gly Glu Val Phe Asn Ala Thr Arg Phe
        210                 215                 220

Ala Ser Val Tyr Ala Trp Asn Arg Lys Arg Ile Ser Asn Cys Val Ala
225                 230                 235                 240

Asp Tyr Ser Val Leu Tyr Asn Ser Ala Ser Phe Ser Thr Phe Lys Cys
                245                 250                 255

Tyr Gly Val Ser Pro Thr Lys Leu Asn Asp Leu Cys Phe Thr Asn Val
                260                 265                 270

Tyr Ala Asp Ser Phe Val Ile Arg Gly Asp Glu Val Arg Gln Ile Ala
            275                 280                 285

Pro Gly Gln Thr Gly Lys Ile Ala Asp Tyr Asn Tyr Lys Leu Pro Asp
        290                 295                 300

Asp Phe Thr Gly Cys Val Ile Ala Trp Asn Ser Asn Asn Leu Asp Ser
305                 310                 315                 320

Lys Val Gly Gly Asn Tyr Asn Tyr Leu Tyr Arg Leu Phe Arg Lys Ser
                325                 330                 335

Asn Leu Lys Pro Phe Glu Arg Asp Ile Ser Thr Glu Ile Tyr Gln Ala
            340                 345                 350

Gly Ser Thr Pro Cys Asn Gly Val Glu Gly Phe Asn Cys Tyr Phe Pro
            355                 360                 365

Leu Gln Ser Tyr Gly Phe Gln Pro Thr Tyr Gly Val Gly Tyr Gln Pro
        370                 375                 380

Tyr Arg Val Val Val Leu Ser Phe Glu Leu Leu His Ala Pro Ala Thr
385                 390                 395                 400

Val Cys Gly Pro Pro Thr Ile Lys Pro Ser Pro Pro Ser Lys Ser Pro
                405                 410                 415

Ala Pro Thr Asn Leu Cys Pro Phe Gly Glu Val Phe Asn Ala Thr Arg
            420                 425                 430

Phe Ala Ser Val Tyr Ala Trp Asn Arg Lys Arg Ile Ser Asn Cys Val
            435                 440                 445

Ala Asp Tyr Ser Val Leu Tyr Asn Ser Ala Ser Phe Ser Thr Phe Lys
        450                 455                 460

Cys Tyr Gly Val Ser Pro Thr Lys Leu Asn Asp Leu Cys Phe Thr Asn
465                 470                 475                 480

Val Tyr Ala Asp Ser Phe Val Ile Arg Gly Asp Glu Val Arg Gln Ile
                485                 490                 495

Ala Pro Gly Gln Thr Gly Asn Ile Ala Asp Tyr Asn Tyr Lys Leu Pro
            500                 505                 510

-continued

```
Asp Asp Phe Thr Gly Cys Val Ile Ala Trp Asn Ser Asn Asn Leu Asp
        515             520             525

Ser Lys Val Gly Gly Asn Tyr Asn Tyr Leu Tyr Arg Leu Phe Arg Lys
    530             535             540

Ser Asn Leu Lys Pro Phe Glu Arg Asp Ile Ser Thr Glu Ile Tyr Gln
545             550             555             560

Ala Gly Ser Thr Pro Cys Asn Gly Val Lys Gly Phe Asn Cys Tyr Phe
            565             570             575

Pro Leu Gln Ser Tyr Gly Phe Gln Pro Thr Tyr Gly Val Gly Tyr Gln
        580             585             590

Pro Tyr Arg Val Val Val Leu Ser Phe Glu Leu Leu His Ala Pro Ala
        595             600             605

Thr Val Cys Gly Pro Pro Thr Ile Lys Pro Ser Pro Pro Ser Lys Ser
    610             615             620

Pro Ala Pro Thr Asn Leu Cys Pro Phe Gly Glu Val Phe Asn Ala Thr
625             630             635             640

Arg Phe Ala Ser Val Tyr Ala Trp Asn Arg Lys Arg Ile Ser Asn Cys
            645             650             655

Val Ala Asp Tyr Ser Val Leu Tyr Asn Ser Ala Ser Phe Ser Thr Phe
            660             665             670

Lys Cys Tyr Gly Val Ser Pro Thr Lys Leu Asn Asp Leu Cys Phe Thr
        675             680             685

Asn Val Tyr Ala Asp Ser Phe Val Ile Arg Gly Asp Glu Val Arg Gln
    690             695             700

Ile Ala Pro Gly Gln Thr Gly Thr Ile Ala Asp Tyr Asn Tyr Lys Leu
705             710             715             720

Pro Asp Asp Phe Thr Gly Cys Val Ile Ala Trp Asn Ser Asn Asn Leu
            725             730             735

Asp Ser Lys Val Gly Gly Asn Tyr Asn Tyr Leu Tyr Arg Leu Phe Arg
            740             745             750

Lys Ser Asn Leu Lys Pro Phe Glu Arg Asp Ile Ser Thr Glu Ile Tyr
        755             760             765

Gln Ala Gly Asn Thr Pro Cys Asn Gly Val Lys Gly Phe Asn Cys Tyr
    770             775             780

Phe Pro Leu Gln Ser Tyr Gly Phe Gln Pro Thr Tyr Gly Val Gly Tyr
785             790             795             800

Gln Pro Tyr Arg Val Val Val Leu Ser Phe Glu Leu Leu His Ala Pro
            805             810             815

Ala Thr Val Cys Gly Pro
            820
```

```
<210> SEQ ID NO 15
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Asn Leu Cys Pro Phe Gly Glu Val Phe Asn Ala Thr Arg Phe Ala
1               5               10              15

Ser Val Tyr Ala Trp Asn Arg Lys Arg Ile Ser Asn Cys Val Ala Asp
            20              25              30

Tyr Ser Val Leu Tyr Asn Ser Ala Ser Phe Ser Thr Phe Lys Cys Tyr
        35              40              45
```

-continued

```
Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
                100                 105                 110

Val Gly Gly Asn Tyr Asn Tyr Leu Tyr Arg Leu Phe Arg Lys Ser Asn
                115                 120                 125

Leu Lys Pro Phe Glu Arg Asp Ile Ser Thr Glu Ile Tyr Gln Ala Gly
    130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
                180                 185                 190

Cys Gly Pro Pro Thr Ile Lys Pro Ser Pro Ser Lys Ser Pro Ala
                195                 200                 205

Pro Thr Asn Leu Cys Pro Phe Gly Glu Val Phe Asn Ala Thr Arg Phe
    210                 215                 220

Ala Ser Val Tyr Ala Trp Asn Arg Lys Arg Ile Ser Asn Cys Val Ala
225                 230                 235                 240

Asp Tyr Ser Val Leu Tyr Asn Ser Ala Ser Phe Ser Thr Phe Lys Cys
                245                 250                 255

Tyr Gly Val Ser Pro Thr Lys Leu Asn Asp Leu Cys Phe Thr Asn Val
                260                 265                 270

Tyr Ala Asp Ser Phe Val Ile Arg Gly Asp Glu Val Arg Gln Ile Ala
                275                 280                 285

Pro Gly Gln Thr Gly Thr Ile Ala Asp Tyr Asn Tyr Lys Leu Pro Asp
    290                 295                 300

Asp Phe Thr Gly Cys Val Ile Ala Trp Asn Ser Asn Asn Leu Asp Ser
305                 310                 315                 320

Lys Val Gly Gly Asn Tyr Asn Tyr Leu Tyr Arg Leu Phe Arg Lys Ser
                325                 330                 335

Asn Leu Lys Pro Phe Glu Arg Asp Ile Ser Thr Glu Ile Tyr Gln Ala
                340                 345                 350

Gly Asn Thr Pro Cys Asn Gly Val Lys Gly Phe Asn Cys Tyr Phe Pro
                355                 360                 365

Leu Gln Ser Tyr Gly Phe Gln Pro Thr Tyr Gly Val Gly Tyr Gln Pro
    370                 375                 380

Tyr Arg Val Val Val Leu Ser Phe Glu Leu Leu His Ala Pro Ala Thr
385                 390                 395                 400

Val Cys Gly Pro Pro Thr Ile Lys Pro Ser Pro Ser Lys Ser Pro
                405                 410                 415

Ala Pro Thr Asn Leu Cys Pro Phe Gly Glu Val Phe Asn Ala Thr Arg
                420                 425                 430

Phe Ala Ser Val Tyr Ala Trp Asn Arg Lys Arg Ile Ser Asn Cys Val
                435                 440                 445

Ala Asp Tyr Ser Val Leu Tyr Asn Ser Ala Ser Phe Ser Thr Phe Lys
    450                 455                 460
```

```
Cys Tyr Gly Val Ser Pro Thr Lys Leu Asn Asp Leu Cys Phe Thr Asn
465             470             475             480

Val Tyr Ala Asp Ser Phe Val Ile Arg Gly Asp Glu Val Arg Gln Ile
                485             490             495

Ala Pro Gly Gln Thr Gly Lys Ile Ala Asp Tyr Asn Tyr Lys Leu Pro
            500             505             510

Asp Asp Phe Thr Gly Cys Val Ile Ala Trp Asn Ser Asn Asn Leu Asp
            515             520             525

Ser Lys Val Gly Gly Asn Tyr Asn Tyr Arg Tyr Arg Leu Phe Arg Lys
            530             535             540

Ser Asn Leu Lys Pro Phe Glu Arg Asp Ile Ser Thr Glu Ile Tyr Gln
545             550             555             560

Ala Gly Ser Lys Pro Cys Asn Gly Val Glu Gly Phe Asn Cys Tyr Phe
                565             570             575

Pro Leu Gln Ser Tyr Gly Phe Gln Pro Thr Asn Gly Val Gly Tyr Gln
            580             585             590

Pro Tyr Arg Val Val Val Leu Ser Phe Glu Leu Leu His Ala Pro Ala
            595             600             605

Thr Val Cys Gly Pro
    610
```

```
<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Thr Ile Lys Pro Ser Pro Pro Ser Lys Ser Pro Ala Pro
1               5               10
```

```
<210> SEQ ID NO 17
<211> LENGTH: 1618
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1275)..(1296)
<223> OTHER INFORMATION: This region may encompass one of the following
      sequences: "HAIMGVAFTW" or "HAIMGVAFTWVMALACAAPPLV"
<220> FEATURE:
<221> NAME/KEY: MOD_RES
<222> LOCATION: (1374)..(1395)
<223> OTHER INFORMATION: This region may encompass one of the following
      sequences: "HAIMGVAFTW" or "HAIMGVAFTWVMALACAAPPLV"
<220> FEATURE:
<223> OTHER INFORMATION: See specification as filed for detailed
      description of substitutions and preferred embodiments

<400> SEQUENCE: 17

Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60
```

```
Phe His Ala Ile His Val Ser Gly Thr Asn Gly Thr Lys Arg Phe Asp
65              70              75                      80

Asn Pro Val Leu Pro Phe Asn Asp Gly Val Tyr Phe Ala Ser Thr Glu
                85              90                      95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
        130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
            275             280             285

Val Asp Cys Ala Leu Asp Pro Leu Ser Glu Thr Lys Cys Thr Leu Lys
        290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480
```

-continued

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
```

-continued

```
              900              905              910
Gln Asn Val Leu Tyr Glu Asn Gln Lys Leu Ile Ala Asn Gln Phe Asn
              915              920              925

Ser Ala Ile Gly Lys Ile Gln Asp Ser Leu Ser Ser Thr Ala Ser Ala
    930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
              965              970              975

Leu Asn Asp Ile Leu Ser Arg Leu Asp Lys Val Glu Ala Glu Val Gln
              980              985              990

Ile Asp Arg Leu Ile Thr Gly Arg  Leu Gln Ser Leu Gln  Thr Tyr Val
              995              1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
    1115             1120             1125

Val Ile  Gly Ile Val Asn Asn  Thr Val Tyr Asp Pro  Leu Gln Pro
    1130             1135             1140

Glu Leu  Asp Ser Phe Lys Glu  Glu Leu Asp Lys Tyr  Phe Lys Asn
    1145             1150             1155

His Thr  Ser Pro Asp Val Asp  Leu Gly Asp Ile Ser  Gly Ile Asn
    1160             1165             1170

Ala Ser  Val Val Asn Ile Gln  Lys Glu Ile Asp Arg  Leu Asn Glu
    1175             1180             1185

Val Ala  Lys Asn Leu Asn Glu  Ser Leu Ile Asp Leu  Gln Glu Leu
    1190             1195             1200

Gly Lys  Tyr Glu Gln Tyr Ile  Lys Trp Pro Trp Tyr  Ile Trp Leu
    1205             1210             1215

Gly Phe  Ile Ala Gly Leu Ile  Ala Ile Val Met Val  Thr Ile Met
    1220             1225             1230

Leu Cys  Cys Met Thr Ser Cys  Cys Ser Cys Leu Lys  Gly Cys Cys
    1235             1240             1245

Ser Cys  Gly Ser Cys Cys Lys  Phe Asp Glu Asp Asp  Ser Glu Pro
    1250             1255             1260

Val Leu  Lys Gly Val Lys Leu  His Tyr Thr Pro Xaa  Xaa Xaa Xaa
    1265             1270             1275

Xaa Xaa  Xaa Xaa Xaa Xaa Xaa  Xaa Xaa Xaa Xaa Xaa  Xaa Xaa Xaa
    1280             1285             1290

Xaa Xaa  Xaa Pro Met Tyr Ser  Phe Val Ser Glu Glu  Thr Gly Thr
    1295             1300             1305
```

-continued

```
Leu Ile  Val Asn Ser Val Leu  Leu Phe Leu Ala Phe  Val Val Phe
    1310             1315              1320

Leu Leu  Val Thr Leu Ala Ile  Leu Thr Ala Leu Arg  Leu Cys Ala
    1325             1330              1335

Tyr Cys  Cys Asn Ile Val Asn  Val Ser Leu Val Lys  Pro Ser Phe
    1340             1345              1350

Tyr Val  Tyr Ser Arg Val Lys  Asn Leu Asn Ser Ser  Arg Val Pro
    1355             1360              1365

Asp Leu  Leu Val Pro Xaa Xaa  Xaa Xaa Xaa Xaa Xaa  Xaa Xaa Xaa
    1370             1375              1380

Xaa Xaa  Xaa Xaa Xaa Xaa Xaa  Xaa Xaa Xaa Xaa Xaa  Pro Met Ala
    1385             1390              1395

Asp Ser  Asn Gly Thr Ile Thr  Val Glu Glu Leu Lys  Lys Leu Leu
    1400             1405              1410

Glu Gln  Trp Asn Leu Val Ile  Gly Phe Leu Phe Leu  Thr Trp Ile
    1415             1420              1425

Cys Leu  Leu Gln Phe Ala Tyr  Ala Asn Arg Asn Arg  Phe Leu Tyr
    1430             1435              1440

Ile Ile  Lys Leu Ile Phe Leu  Trp Leu Leu Trp Pro  Val Thr Leu
    1445             1450              1455

Ala Cys  Phe Val Leu Ala Ala  Val Tyr Arg Ile Asn  Trp Ile Thr
    1460             1465              1470

Gly Gly  Ile Ala Ile Ala Met  Ala Cys Leu Val Gly  Leu Met Trp
    1475             1480              1485

Leu Ser  Tyr Phe Ile Ala Ser  Phe Arg Leu Phe Ala  Arg Thr Arg
    1490             1495              1500

Ser Met  Trp Ser Phe Asn Pro  Glu Thr Asn Ile Leu  Leu Asn Val
    1505             1510              1515

Pro Leu  His Gly Thr Ile Leu  Thr Arg Pro Leu Leu  Glu Ser Glu
    1520             1525              1530

Leu Val  Ile Gly Ala Val Ile  Leu Arg Gly His Leu  Arg Ile Ala
    1535             1540              1545

Gly His  His Leu Gly Arg Cys  Asp Ile Lys Asp Leu  Pro Lys Glu
    1550             1555              1560

Ile Thr  Val Ala Thr Ser Arg  Thr Leu Ser Tyr Tyr  Lys Leu Gly
    1565             1570              1575

Ala Ser  Gln Arg Val Ala Gly  Asp Ser Gly Phe Ala  Ala Tyr Ser
    1580             1585              1590

Arg Tyr  Arg Ile Gly Asn Tyr  Lys Leu Asn Thr Asp  His Ser Ser
    1595             1600              1605
```

-continued

```
Ser Ser  Asp Asn Ile Ala Leu  Leu Val Gln
    1610                1615
```

```
<210> SEQ ID NO 18
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
agctggctag cgtttaaact taagcttggt accgagctcg gatccactag tccagtgtgg        60
tggaattctg cagatatcca gcacagtggc ggccgctcga gtctagaggg cccgtttaaa       120
c                                                                       121
```

SINGLE-CHAIN CORONAVIRUS VIRAL MEMBRANE PROTEIN COMPLEXES

CROSS-REFERENCE TO RELATED APPLICATIONS

This application claims benefit and priority to International Application No. PCT/US21/47982 filed on Aug. 27, 2021 and U.S. Provisional Application No. 63/071,681, filed Aug. 28, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 21, 2021, is named 2329-52_PCT_SL.txt and is 155,139 bytes in size.

TECHNICAL FIELD

The present disclosure relates generally to novel recombinant protein coronavirus antigens and vaccine compositions using the same, in which the novel recombinant protein is a single-chain (SC) viral membrane protein complex derived from the spike (S), envelop (E) and membrane (M) protein of a coronaviruses such as SARS-CoV-2, the causal agent for COVID-19. The present disclosure provides methods for immunization of a subject using the vaccine compositions for treating or preventing clinical signs caused by coronaviruses infection.

BACKGROUND

Since the COVID-19 outbreak in December 2019, a worldwide pandemic has developed. So far, over millions have been infected and hundreds of thousands of deaths have been reported. Accordingly, as the numbers continue to escalate daily, vaccine development has become a top priority worldwide.

Current coronavirus vaccine candidates exist within three categories: inactivated virus, cDNA or mRNA of S protein, and recombinant S protein. Use of inactivated SARS-CoV-2 virus as a vaccine is highly risky. Thus, S-protein is the primary target for the majority of vaccine designs. However, a single S-protein-based vaccine may not prove to be as immunogenic as the whole viral membrane which contains other viral membrane proteins. For example, antibodies produced by immunized S-protein would neither block the viral-membrane E-protein's ion channel nor the M-protein's membrane-assemble functions. Further, a single protein vaccine may lose potency through mutation of S-protein on the virus. Accordingly, the development of new and powerful vaccines with longer-antibody production duration and stronger-resistance to a single protein mutation are needed for an effective protection against the COVID-19 pandemic.

SUMMARY

The present disclosure relates to a recombinant coronavirus single-chain (SC) viral membrane protein complex that includes spike (S)-, envelope (E)-, and membrane (M)-proteins (herein referred to as SC-membrane protein), nucleic acids encoding such protein complexes, and their use in vaccines for production of an effective immunogenicity against the coronavirus. In a specific embodiment, the coronavirus is SARS-CoV-2. Such membrane protein complexes are designed to mimic total antigenic sites of the viral membrane protein as an effective and immunogenic vaccine. While the disclosure below is directed to COVID-19 single-chain (SC) viral membrane protein complexes, it is understood that said disclosure can be applied equally as well to other coronaviruses having corresponding spike (S)-, envelope (E)- and membrane (M)-proteins.

In an embodiment, a COVID-19 single-chain (SC) membrane protein is provided that includes one or more of the viral spike (S)-, envelope (E)-, and membrane (M)-protein or fragments thereof. In a specific embodiment, the viral (S) amino acid sequence includes SEQ ID NO: 1, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof; the viral (E) protein includes the amino acid sequence of SEQ ID NO. 2, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof; and the viral (M) protein includes the amino acid sequence of SEQ ID NO. 3, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof.

In an embodiment, the SC membrane proteins may also be engineered utilizing viral spike (S)-, envelope (E)-, and membrane (M)-proteins, or fragments thereof, derived from identified SARS-CoV-2 variants. Such variants (Alpha, Beta, Gamma and Delta variants) include for examples (see, FIGS. 9A-B and FIGS. 10A-B)

The coronavirus SC-membrane protein may further include one or more linker sequences. The linker sequence may be a polypeptide of 1-80 amino acids. The linker sequence may be a polypeptide of 10-50 amino acids. The linker may have a length of 10, 11, 12, 13, 14, 15, 16, 17, 18, 19, 20, 21 or 22 amino acids. The linker may have a length of 10 amino acid sequence of HAIMGVAFTW (SEQ ID NO: 4) and/or a 22 amino acid sequence of HAIMGVAFTWVMALACAAPPLV (SEQ ID NO: 5).

Another aspect of the present disclosure pertains to nucleic acids encoding the SC-membrane proteins disclosed herein. Such nucleic acids may be introduced into a variety of different expression vectors, including for example, bacterial and viral expression vectors for expression of the SC-membrane protein in a host cell of interest. In a specific embodiment, the nucleic acid is a cDNA or mRNA molecule capable of encoding the SC-membrane proteins. A nucleic acid molecule encoding a SC-membrane protein may be chemically synthesized based on the SC-membrane protein sequence encoded by the nucleic acid.

Recombinant expression vectors having nucleic acid molecules encoding SC-membrane proteins are also provided. Such recombinant expression vectors include, for example, bacterial expression vectors and eukaryotic expression vectors. Expression vectors include viral vectors such as adenovirus recombinant expression vectors. The provided nucleic acid molecules encoding SC-membrane proteins can be used for in vitro or in vivo gene expression of the protein for use in prevention and/or treatment of coronavirus infection.

In still another aspect, a method is provided of preparing a SC-membrane protein using nucleic acids encoding the SC-membrane protein. The preparation method according to the present disclosure may be performed through recombinant DNA or mRNA technology known in the art using a nucleic acid encoding the SC-membrane protein. This method includes, for example, (i) preparing an expression vector including a nucleic acid encoding the SC-membrane protein, (ii) transforming the expression vector into host cells of interest, and (iii) culturing the transformed host cells. In a further step, the SC-membrane protein may be purified from the resultant culture broth.

Also disclosed is a nanoparticle having the disclosed SC-membrane protein. The nanoparticles can be created from biological molecules or from non-biological molecules. In some cases, the SC-membrane protein is cross-linked to a polymer or lipids on the nanoparticle surface. In embodiments, the SC-membrane protein is adsorbed onto the nanoparticle surface. In some embodiments, the SC-membrane protein is adsorbed onto the nanoparticle surface and then crosslinked to the nanoparticle surface. In some embodiments, the SC-membrane protein is encapsulated into the nanoparticle.

In an embodiment, the nanoparticle is a nanoliposome and may be composed of naturally occurring (e.g. soybean- or egg yolk-derived) or semi-synthetic phospholipids such as 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1,2-dimyristoyl-sn-glycero-3-phospho-(1'-rac-glycerol) (DMPG), 1,2-dioleoyl-sn-glycero-3-phospho-(1'-rac-glycerol) (DOPG), dipalmitoyl phosphatidylserine (DPPS), distearoyl phosphatidylserine (DSPS), dipalmitoyl phosphatidylinositol (DPPI), distearoyl phos phatidylinositol (DSPI), dipalmitoyl phosphatidic acid (DPPA), distearoyl phosphatidic acid (OSPA), 1,2-diacyl-3-trimethyl-ammonium-propanes, (including but not limited to, dioleoyl (DOTAP), 1,2-dipalmitoyl-sn-glycero-3-phosphoetha-nolamine-N [methoxy(polyethylene glycol)-2000] (DPPE-PEG2000), 1,2-distearoyl-sn-glycero-3-phosphoetha-nolamine-N-[methoxy(polyethylene glycol)-1000] (DSPE-PEG2000), and cholesterol.

Such nanoparticles, or nanoliposomes may be incorporated into vaccine compositions as disclosed below.

The present disclosure provides a vaccine composition containing a SC-membrane protein, or a SC-membrane protein encoding nucleic acid, i.e., cDNA or RNA, as an active ingredient. As used herein, the term "vaccine" refers to a composition able to prevent the infection or re-infection with COVID-19, reducing the severity of symptoms or eliminating symptoms by COVID-19, or substantially or completely removing COVID-19 or the disease by COVID-19, by inducing an immune response to COVID-19 in a human host. Thus, the vaccine composition disclosed herein may be administered prophylactically to a subject, e.g., a human, before infection with COVID-19, or may be thera-peutically administered to subjects after infection with COVID-19. Here, the term "immune response" includes either or both of a humoral immune response and a cellular immune response.

The vaccine composition provided herein may be prepared in any suitable and pharmaceutically acceptable formulation. It may be provided in the form of an immediately administrable solution or suspension, or a concentrated crude solution suitable for dilution before administration or may be provided in a form capable of being reconstituted, such as a lyophilized, freeze-dried, or frozen formulation.

The vaccine composition may contain a pharmaceutically acceptable carrier in order to be formulated. The carrier typically includes a diluent, an excipient, a stabilizer, a preservative, and the like. The vaccine composition of the present disclosure may further contain an adjuvant. The adjuvant may be composed of one or more substances that enhance the immune response to an antigen, e.g., the SC-membrane protein. The adjuvant may function as a tissue reservoir that slowly releases an antigen and/or as a lym-phoid system activator that nonspecifically enhances an immune response (Hood et al., Immunology, Second Ed., 1984, Benjamin/Cummings: Menlo Park, Calif., p. 384).

A method of vaccinating a subject for COVID-19 is provided that includes administering a disclosed COVID-19 vaccine composition to a subject in need thereof. The disclosed vaccine composition may be administered in a number of ways. For example, the disclosed vaccine composition can be administered intramuscularly, intranasally, orally, intravenously, subcutaneously, transdermally (e.g., by microneedle), intraperitoneally, ophthalmically, sublin-gually, or by inhalation.

The disclosed SC-membrane proteins may be used in immunoassays, immune-detection, immune-diffusion, immune-kits, immunostaining (such as for COVID-19). The SC-membrane proteins may be for use in the treatment or prevention of COVID-19 infection as components of vaccine compositions.

In still yet another aspect, a diagnostic composition that employs the use of the SC-membrane composition and methods for detecting a COVID-19 specific antibody are provided. The detection composition serves to detect a COVID-19-specific antibody, especially a Spike (S), envelop (E) or membrane (M) antigen-specific antibody, in a subject sample, and the use of the composition is able to distinguish coronavirus-infected and uninfected subjects from each other by bringing the same into contact with a sample and measuring the extent of reaction therebetween. In particular, this composition may be useful to distinguish whether or not a patient with symptoms identical or similar to those of coronavirus disease is infected with coronavirus during the period of risk of onset of coronavirus disease. In a specific embodiment the coronavirus is COVID-19.

BRIEF DESCRIPTION OF THE FIGURES

FIG. 1A. Configuration model of the three S, E and M proteins on the SARS-CoV-2 viral membrane. FIG. 1B. Genome map of SARS-CoV-2. FIG. 1C. Depiction showing the linking of three proteins together by membrane linkers or 10-(10aa) or 22-(22aa) amino acid residues.

FIG. 3. Amino acid sequence of SC-SEM-1 (SEQ ID NO: 17). The available translated amino acid residues for the S-protein 1273 amino acids (aa) (bold), E-protein 75 amino acids (aa) (italics color), and M protein 222 amino acids (aa) (underlined) from GenBank MN908947 are linked together by two 10aa or 22aa likers. The 10aa linker is HAIMGVAFTW (SEQ ID NO: 4) (single-letter amino acid code), and the 22aa is HAIMGVAFTWVMALACAAPPLV (SEQ ID NO: 5) (single-letter amino acid code) (Ruan K H et al., 2006, Biochemistry 45::14003-11). The four Proline residues that were added to make the smooth turns at the connection sites are showed with bold "P".

FIG. 4A-B. Comparison of the expression levels of COX-2-10aa-PGIS using Ad-virus (lane 2 and 4) and pcDNA3.1 (lanes 1 and 3) in HEK293 (1, 2) and COS-7 (3,4) cells. FIG. 4A. Quantitative activity data; FIG. 4B. Western blot analysis.

FIG. 6 discloses SEQ ID NO: 18.

FIG. 9A-B. FIG. 9A. Construction of 3D-structural model of single-chain four RBD variants (SC-V0-V3) as a comprehensive COVID-19 variant vaccine. The four RBD domains including wild type (V0), Alpha variant (UK variant (V1)), Beta variant (South Africa variant (V2)), and the combination of the variants (V3) of Gamma (Brazil P.1/ 501Y.V3) and New York, B.1.526 were linked together by three of the highly flexible linkers (14 amino acid residues). The constructed four RBD variants become a SC-polypeptide. The 3D-structure of RBD binding to ACE2 adopted from PBD 7E3J were used as templates. FIG. 9B. Amino acid residues of SC-V0-V3. The full amino acid residues for the RBDs of the SC-V0-V3 are shown. The 14 amino acid residues used as the flexible linkers are in italic with bold and underlines. The point-mutated amino acid residues within the variant RBDs are shown in bold with underlines.

FIG. 10A-B. FIG. 10A. Construction of 3D-structural model of SC-three RBDs (SC-V0/V3/V4) with three mutants as a comprehensive COVID-19 variant vaccine. The two RBD domains including wild type (V0), the combination of the variants (V3) of Gamma variant (Brazil P.1/501Y.V3) and New York, B.1.526, and Delta variant (Indiant variant, B.1.617.2 (V4)) were linked together by one of the highly flexible linkers (14 amino acid residues). The constructed three RBD variants become a SC-polypeptide. The 3D-structure of RBD binding to ACE2 adopted from PBD 7E3J were used as templates. FIG. 10B. Amino acid residues of SC-V0/V3/V4. The full amino acid residues for the RBDs of the SC-V)/V3/V4 are shown. The 14 amino acid residues used as the flexible linkers are in italic with bold and underlines. The point-mutated amino acid residues within the variant RBDs are shown in bold with underlines.

FIGS. 11A and 11B each disclose SEQ ID NO: 18.

DETAILED DESCRIPTION

Figure 1:
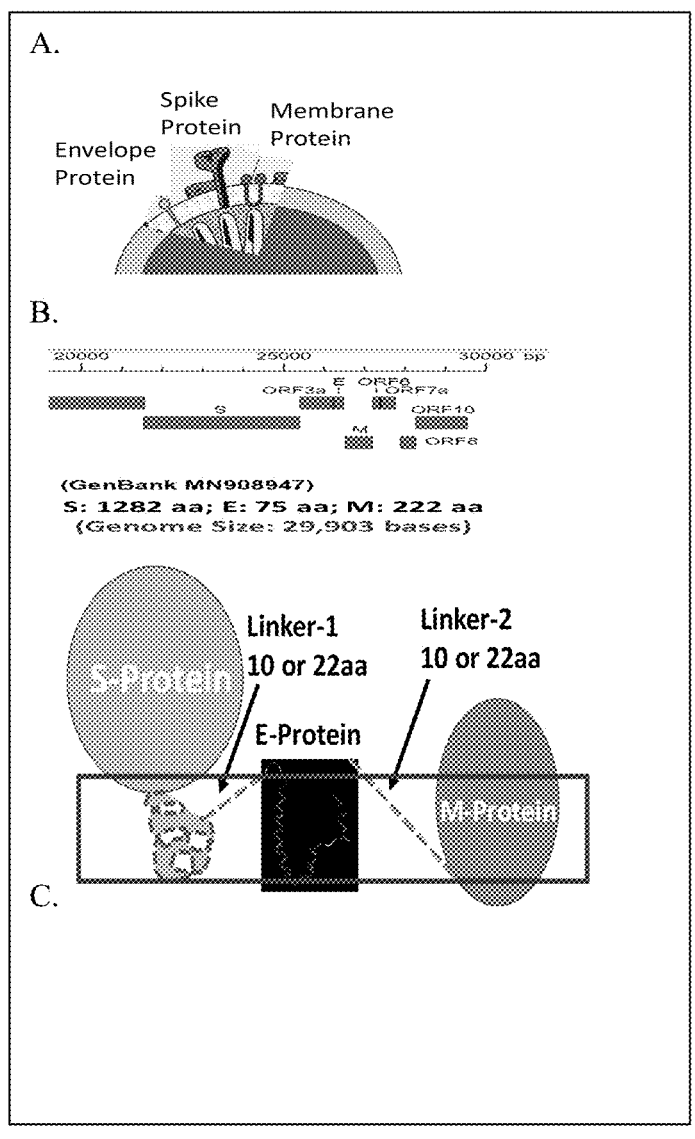
FIG. 1A-C.

The present disclosure relates to novel recombinant coronavirus single-chain (SC) viral membrane protein complexes that include spike (S)-, envelope (E)-, and membrane (M)-protein domains (herein referred to as "SC-membrane protein"). The different domains of the SC-membrane protein, i.e., the S-, E-, and M-domains may be linked by one or more linker sequences. The terms "spike", "envelop" and "membrane" refers to specific proteins of the coronavirus that are well known by the person skilled in the art. In a specific embodiment, the coronavirus is a COVID-19 virus (see, FIG. 1A). Such SC-membrane proteins are designed to mimic total antigenic sites of the viral membrane protein as an effective and immunogenic vaccine.

As used herein, the term "coronavirus" is meant to include all microorganisms classified and identified as coronavirus. There are hundreds of coronaviruses, most of which circulate among such animals as pigs, camels, bats and cats. Coronaviruses are a large family of viruses that usually cause mild to moderate upper-respiratory tract illnesses, such as the common cold. However, coronaviruses have emerged from animal reservoirs over the past two decades to cause serious and widespread illness and death. Such coronaviruses include, for example, SARS coronavirus (SARS-CoV) causing severe acute respiratory syndrome (SARS), MERS coronavirus (MERS-CoV) causing Middle East respiratory syndrome (MERS) and SARS-CoV-2 causing coronavirus disease 2019 (COVID-19). While the disclosure below is directed to COVID-19 single-chain (SC) viral membrane protein complexes, it is understood that said disclosure can be applied equally as well to other coronaviruses and their corresponding spike (S)-, envelope (E) and membrane (M) proteins.

As used herein, the term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard textbooks of biochemistry. Within the amino acid sequence, the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations and other proteins in addition. Further, the term also relates to protein fragments. Moreover, it includes chemically modified proteins. Such modifications may be artificial modifications or naturally occurring modifications such as phosphorylation, glycosylation, myristylation and the like.

As disclosed in detail below, the provided SC-membrane proteins disclosed herein utilize different combinations and orientations of coronavirus S-, E- and M-proteins as well as, optionally, linker sequences linking the S-, E- and M-proteins or fragments thereof.

In a specific aspect, the SC-membrane protein includes a spike (S) protein having the amino acid sequence of SEQ ID NO: 1, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof.

In a specific aspect, the SC-membrane protein includes an envelope protein (E) having the amino acid sequence of SEQ ID NO. 2, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof.

In a specific aspect, the SC-membrane protein includes a membrane protein (M) having the amino acid sequence of SEQ ID NO. 3, a sequence having at least 95%, 96%, 97%, 98%, 99%, 99.2%, 99.5%, 99.6%, 99.7%, 99.8%, 99.9%, 99.95%, 99.98% or 99.99% sequence identity thereto, or fragments thereof.

Included are SC-membrane proteins that include (S), (E) and (M) viral proteins as disclosed above but which contain amino acid substitutions or deletions and which are nevertheless able to elicit a protective immune response when included in a vaccine composition.

Included are SC-membrane proteins that include (S), (E), and (M) viral proteins derived from identified SARS-CoV-2 variants. Such variants include, but are not limited to the South African, Brazilian and New York variants.

Each of the protein domains of the SC-membrane protein may be linked by amino acid linker sequences. The term "linker" refers to a short, non-native peptide sequence that links two proteins or fragments of a protein. Such linker sequences include any linker sequence that permits the folding of the different protein domains to mimic as closely as possibly the naturally occurring viral membrane complex. In an aspect, the linker sequence is a polypeptide having 1-70 amino acids. In a specific aspect, the linker sequence is a polypeptide having 10-50 amino acids. In a more specific embodiment, the linker has a length of 10, 11, 12, 13, 14, 15, 16, 17, 18, 19, 20, 21 or 22 amino acids. In a specific embodiment the linker sequence is the 10 amino acid sequence: HAIMGVAFTW (SEQ ID NO: 4). In another embodiment, the linker sequence is the 22 amino acid sequence: HAIMGVAFTWVMALACAAPPLV (SEQ ID NO:5). The SC-membrane proteins disclosed herein can utilize different combinations and orientations of the S-, E-, M-proteins as well as linkers such as the 10aa and 22aa linkers.

In a specific embodiment, the SC-membrane proteins may be referred to as "single-chain (SC)-SEM" or, when in reverse orientation, "single chain (SC)-MES" membrane protein complexes. Specific examples include, for example, SC-SEM 1 (SEQ ID NO. 6), SC-SEM-2 (SEQ ID NO: 7), SC-MES-1(R) (SEQ ID NO: 8) or SC-MES-2 (R) (SEQ ID NO:9). In another aspect, the SC-membrane protein is an amino acid sequence having at least 95%, 96%, 97%, 98%, 99%, 99.2%, 99.5%, 99.6%, 99.7%, 99.8%, 99.9%, 99.95%, 99.98% or 99.99% sequence identity thereto to SC-SEM 1 (SEQ ID NO: 6), SC-SEM-2 (SEQ ID NO: 7), SC-MES-1 (R) (SEQ ID NO: 8) or SC-MES-2 (R) (SEQ ID NO: 9), or portion thereof.

Specific examples also include, for example, the SC-membrane proteins of SEQ ID NO. 10, 11, 12, 13, 14 and 15 and SC-membrane proteins having at least 95%, 96%, 97%, 98%, 99%, 99.2%, 99.5%, 99.6%, 99.7%, 99.8%, 99.9%, 99.95%, 99.98% or 99.99% sequence identity thereto, or portion thereof. The present disclosure also relates to nucleic acid molecules encoding for the SC-membrane proteins disclosed above. "Nucleic acid" or "nucleic acid sequence" or "nucleotide sequence" refers to polynucleotides including DNA molecules, RNA molecules, cDNA molecules or derivatives. The term encompasses single as well as double stranded polynucleotides. In a specific embodiment, the nucleic acid includes a cDNA or mRNA molecule capable of encoding the SC-membrane proteins disclosed herein.

The nucleic acids of the present disclosure encompass isolated polynucleotides (i.e., isolated from its natural context) and genetically modified forms. Moreover, included are chemically modified polynucleotides including naturally occurring modified polynucleotides such as glycosylated or methylated polynucleotides or artificially modified ones such as biotinylated polynucleotides. The terms "nucleic acid" and "polynucleotide" also specifically include nucleic acids composed of bases other than the five biologically occurring bases (adenine, guanine, thymine, cytosine and uracil).

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference).

The protein sequences or nucleic acid sequences disclosed herein can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the disclosure. To obtain gapped alignments for comparison purposes, Gapped BLAST can be utilized as described in Altschul et al. (1997) Nucleic Acids Res. 25 (17): 3389-3402. When utilizing BLAST and Gapped BLAST programs, the default parameters of the respective programs (e.g., BLASTP and BLASTN) can be used. See the homepage of the National Center for Biotechnology Information.

Methods of preparing a recombinant SC-membrane protein are provided. The preparation method may be performed through recombinant DNA technology known in the art using a nucleic acid encoding the SC-membrane protein. This method includes (i) preparing an expression vector having a nucleic acid encoding the SC-membrane protein, (ii) transforming the expression vector into host cells, (iii) culturing the transformed host cells, and optionally (iv) isolating and purifying the SC-membrane protein from the resultant culture broth.

The SC-membrane protein may also be chemically synthesized based on the SC-membrane protein amino acid sequence. Such chemical synthesis methods are well known in the art, and, for example, solid-phase synthesis technology, solution-phase synthesis technology and the like may be used, and commercially available automated DNA synthesizers and the like using these technologies may be used. (see, Nucl. Acid Res. 14:5399-5467, 1986; Tet. Lett. 27:5575-5578, 1986; Nucl. Acid Res. 4:2557, 1977; and Lett., 28:2449, 1978) and the like.

When the preparation method is through recombinant DNA technology, the expression vector may be a nucleic acid in the form of a plasmid, a cosmid, a phagemid, a phage, a viral vector or the like. Depending on the host microorganism, an appropriate vector may be purchased among commercially available vectors or may be used after being purchased and modified. For example, when *Escherichia coli* is used as the host microorganism, pUC19, pSTV28, pBBR1MCS, pBluscriptII, pBAD, pTrc99A, pET, pACYC184, pBR322, pJE101, pJE102, pJE103, etc. may be used.

For expression vector construction including recombinant DNA technology, reference may be made to Sambrook et al., Molecular Cloning, A Laboratory Manual, Cold Spring Harbor Laboratory Press, (2001), F M Ausubel et al, Current Protocols in Molecular Biology, John Wiley amp; Sons, Inc. (1994), and Marston, F (1987) DNA Cloning Techniques) and the like. All of the documents cited in the present specification are incorporated by reference in their entirety.

The expression vector may include a regulatory sequence that affects transcription and translation of the target gene by being operably linked to the target gene, in addition to the target gene encoding the recombinant protein antigen. Such a regulatory sequence usually includes a promoter sequence, a transcription termination signal sequence (polyadenylation signal), and the like. As used herein, the term "being operably linked" means a linkage such that the transcription and/or translation of a gene are affected. For example, if a promoter affects the transcription of a gene linked thereto, the promoter and the gene are regarded as operably linked. Regulatory sequences also include enhancer sequences that function to regulate the transcription of a gene.

As used herein, the term "promoter" refers to a nucleic acid sequence having a function of controlling transcription of one or more genes, which is located upstream (5' side) of the transcription initiation point of a gene and includes a binding site for a DNA-dependent RNA polymerase, a transcription initiation point, a transcription factor binding site, and the like. So long as the promoter is capable of expressing the target gene linked thereto, any of a constitutive promoter (a promoter that induces expression constantly in a certain organism) and an inducible promoter (a promoter that induces expression of a target gene in response to a certain external stimulus) may be used. In an embodiment, a promoter suitable for a certain host microorganism is used. Enhancer sequences may also be employed to control the expression of SC-membrane protein.

The expression vector is configured to include a terminator sequence which is a transcription termination sequence, in addition to the promoter. The terminator sequence is a sequence that acts as a poly(A) addition signal (polyadenylation signal) to increase the completeness and efficiency of transcription. Suitable terminator sequences, depending on the host microorganism, are known in the art.

The expression vector may further include a selectable marker gene. The selectable marker gene is a gene encoding a trait that enables selection of a host microorganism containing such a marker gene and is generally an antibiotic resistance gene.

The expression vector may also include a restriction enzyme recognition site for easy cloning of the SC-membrane protein encoding nucleic acid. The expression vector may then be transformed into a host microorganism for expression of the SC membrane protein.

In a specific embodiment, SC-membrane protein encoding nucleic acid may be introduced into recombinant delivery vectors such as genetically engineered viral or bacterial vectors. Viral vectors include bacteriophages, herpesvirus, adenovirus, poliovirus, vaccinia virus, defective retroviruses, adeno-associated virus (AAV), lentiviruses, plant viruses, and hybrid vectors. Methods of transforming viral vectors with a recombinant DNA construct are also well described in the art. In a specific embodiment, adenovirus viral vectors may be used for expression of SC-membrane proteins within a subject. Such adeno-associated virus vectors include, for example, commercial AAV vector available from vendors such as Vectorbiolabs, Vectorbuilder, Vigene, Creative-Biogene or customer made Ad5 vectors without E1, E2b, E3-sequences. Adenovirus vectors include, for example, the chimeric Ad5/F35 hybrid virus.

The present disclosure provides recombinant cells into which expression vectors designed for expression of SC-membrane proteins have been introduced. Such cells include bacterial as well as eukaryotic cells. Transformation refers to the modification of a genotype of a cell due to the introduction of a nucleic acid, and the introduced nucleic acid may be present independently of the genome of the host cell or in the state of being incorporated into the genome of the host cell.

Methods of transforming the expression vector into the host cell are also known in the art, and any of the known methods may be selected and used. For example, when the host cell is prokaryotic cells such as *Escherichia coli*, the transformation may be carried out through a $CaCl_2$) method, a Hanahan method, an electroporation method, a calcium phosphate precipitation method, or the like, and when the host cell is eukaryotic cells such as yeast or mammalian cells, a microinjection method, a calcium phosphate precipitation method, an electroporation method, a liposome-mediated transfection method, a DEAE-dextran treatment method, a gene bombardment method, or the like may be used. Regarding details of the transformation method, reference may be made to (Cohen, S. N. et al., Proc. Natl. Acad. Sci. USA, 9:2110-2114 (1973); Hanahan, D., J. Mol. Biol., 166:557-580 (1983); Dower, W. J. et al., Nucleic. Acids Res., 16:6127-6145 (1988); Capecchi, M. R., Cell, 22:479 (19800; Graham, F. L. et al., Virology, 52:456 (1973);

Neumann, E. et al., EMBO J., 1:841 (1982); Wong, T. K. et al., Gene, 10:87 (1980); Gopal, Mol. Cell Biol., 5:1188-1190 (1985); Yang et al., Proc. Natl. Acad. Sci., 87:9568-9572 (1990); Maniatis et al., Molecular Cloning: A Laboratory Manual, Cold Spring Harbor Laboratory (1982); Hitzeman et al., J. Biol. Chem., 255, 12073-12080 (1980); and Luchansky et al Mol. Microbiol. 2, 637-646 (1988), etc.)

The host cell that may be used for transformation in the method of the present disclosure may be prokaryotic or eukaryotic cells. As the prokaryotic cells, any of gram-positive bacteria and gram-negative bacteria may be used. In a specific embodiment, *Escherichia coli* is used. In order to optimize expression and maintain the functions of the SC-membrane protein in *Escherichia coli*, the cell may have impaired protease activity. Also, the nucleic acid sequence of the SC membrane protein may be optimized with a codon usage preferred in *Escherichia coli* (see, Wada et al., Nucleic Acids Res. 20:2111-2118 (1992)).

The host cell transformed above is cultured, thus producing the recombinant SC-membrane protein. The culture of the transformed host cell may be performed through any method known in the art. As the medium used for cell culture, any of a natural medium and a synthetic medium may be used, so long as it contains a carbon source, a nitrogen source, a trace element, etc. which may be efficiently used by the transformed host cell. When animal cells are used as host cells, Eagle's MEM (Eagle's minimum essential medium, Eagle, H. Science 130:432 (1959)0, α-MEM (Stanner, C. P. et al., Nat. New Biol. 230:52 (1971)), Iscove's MEM (Iscove, N. et al., J. Exp. Med. 147:923 (1978)), DMEM (Dulbecco's modification of Eagle's medium, Dulbecco, R. et al., Virology 8:396 (1959)) or the like may be used. Regarding details of the medium, see, for example, R. Ian Freshney, Culture of Animal Cells, A Manual of Basic Technique, Alan R. Liss, Inc., New York.

Methods of isolating and purifying the SC-membrane protein are also well known in the art, and any known method may be used. Examples thereof may include ultrafiltration, gel filtration, ion exchange chromatography, affinity chromatography (when labeled peptides are bound), HPLC, hydrophobic chromatography, isoelectric point chromatography, and combinations thereof.

Also disclosed is a nanoparticle having a SC-membrane protein. Such nanoparticles can be natural or synthetic and may be incorporated into a vaccine composition. They can be created from biological molecules or from non-biological molecules. In some cases, the protein complex is crosslinked to a polymer or lipid on nanoparticle surface. In embodiments, the protein complex is adsorbed onto the nanoparticle surface. In some embodiments, the protein complex is adsorbed onto the nanoparticle surface and then crosslinked to the nanoparticle surface. In some embodiments, the protein complex is encapsulated into the nanoparticle.

In particular embodiments, the nanoparticle is formed from a biocompatible polymer. Examples of biocompatible polymers include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In some cases, the nanoparticle is formed from a polyethylene glycol (PEG), poly(lactide-co-glycolide) (PLGA), polyglycolic acid, poly-beta-hydroxybutyrate, polyacrylic acid ester, or a combination thereof.

In a specific embodiment the nanoparticle is a nanoliposome. Such nanoliposomes may be composed of phospholipids such as 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1,2-dioleoyl-sn-glycero-3-phosphocholine (DOPC), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1,2-dimyristoyl-sn-glycero-3-phospho-(1'-rac-glycerol) (DMPG), 1,2-dioleoyl-sn-glycero-3-phospho-(1'-rac-glycerol) (DOPG), dipalmitoyl phosphatidylserine (DPPS), distearoyl phosphatidylserine (DSPS), dipalmitoyl phosphatidylinositol (DPPI), distearoyl phos phatidylinositol (DSPI), dipalmitoyl phosphatidic acid (DPPA), distearoyl phosphatidic acid (OSPA), 1,2-diacyl-3-trimethylammonium-propanes, (including but not limited to, dioleoyl (DOTAP), 1,2-dipalmitoyl-sn-glycero-3-phospho-ethanolamine-N [methoxy(polyethylene glycol)-2000] (DPPE-PEG2000), 1,2-distearoyl-sn-glycero-3-phospho-ethanolamine-N-[methoxy(polyethylene glycol)-1000] (DSPE-PEG2000), and cholesterol.

In some embodiments, the SC-membrane protein is coated on the nanoparticle using a crosslinking agent. In some embodiments, the SC-membrane protein is adsorbed onto the nanoparticle surface. In some embodiments, the SC-membrane protein is adsorbed onto the nanoparticle surface followed by covalent crosslinking of the SC-membrane protein to the nanoparticle surface using a crosslinking agent.

Crosslinking agents suitable for crosslinking the SC-membrane protein to produce the nanoparticle, or to coat SC-membrane protein on the nanoparticle are known in the art, and include those selected from the group consisting of formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfydryl addition or disulfide reduction, carbohydrate reactive crosslinkers, carboxyl reactive crosslinkers, photoreactive crosslinkers, cleavable crosslinkers, AEDP, APG, BASED, BM(PEO)3, BM(PEO)4, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, and Sulfo-EGS.

The present disclosure provides a vaccine composition containing a SC-membrane protein, or a SC-membrane protein encoding nucleic acid, as an active ingredient. As used herein, the term "vaccine" refers to a composition able to prevent the infection or re-infection with COVID-19, reducing the severity of symptoms or eliminating symptoms by COVID-19, or substantially or completely removing COVID-19 or the disease by COVID-19, by inducing an immune response to COVID-19 in a human host. Thus, the vaccine composition disclosed herein may be administered prophylactically to a subject, i.e., a human, before infection with COVID-19, or may be therapeutically administered to subjects after infection with COVID-19. Here, the term "immune response" includes either or both of a humoral immune response and a cellular immune response.

Also provided is the in vivo administration of a nucleic acid encoding the SC-membrane protein so that the protein is expressed in the mammal (e.g., nucleic acid vaccine, DNA or RNA vaccine). In an embodiment, the nucleic acid includes a nucleotide sequence that encodes the SC-membrane protein operably linked to regulatory elements needed for gene expression, such as a promoter, an initiation codon, a stop codon, enhancer, and a polyadenylation signal. Regulatory elements are typically selected that are operable in the species to which they are to be administered.

The nucleic acid of the vaccine composition can be "naked" DNA, cDNA or mRNA or can be operably incorporated in a vector. Nucleic acids may be delivered to cells in vivo using methods well known in the art such as direct infection of DNA, receptor-mediated DNA uptake, viral-mediated transfection or non-viral transfection and lipid-based transfection, all of which may involve the use of vectors. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G and Wu, C. H. (1988) J. Biol. Chem. 263: 14621; Wilson et al. (1992) J. Biol. Chem. 267: 963-967, and U.S. Pat. No. 5,166,320). Binding of the DNA ligand complex to the receptor may facilitate uptake of the DNA by receptor-mediated endocytosis. A DNA ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88: 8850; Cristriano et al. (1993) Proc. Natl. Acad. Sci. USA 90: 2122-2126).

Useful delivery vectors for inclusion in the vaccine compositions include biodegradable microcapsules immuno-stimulating complexes (ISCOMs) or liposomes, and genetically engineered attenuated live vectors such as viruses or bacteria. Viral vectors include Bacteriophages, Herpes virus, Adenovirus, Polio virus, Vaccinia virus, defective retroviruses and adeno-associated virus (AAV). Methods of transforming viral vector with an exogenous DNA construct are also well described in the art.

Liposome vectors are unilamellar or multilamellar vesicles, having a membrane portion formed of lipophilic material and an interior aqueous portion. The aqueous portion is used to contain the polynucleotide material to be delivered to the target cell. In general, the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., Biochemistry 27:3917 3925 (1988); and H. Eibl, et al., Biophysical Chemistry 10:261 271 (1979). Alternatively, a microsphere such as a polylactide-co-glycolide biodegradable microsphere can be utilized. A nucleic acid construct is encapsulated or otherwise complexed with the liposome or microsphere for delivery of the nucleic acid to a tissue, as is known in the art.

Alternatively, the nucleic acid (e.g., DNA or mRNA) may be incorporated in a cell in vitro or ex vivo by transfection or transformation and the transfected or transformed cell (e.g., an immune cell such as a dendritic cell), which expresses the SC-membrane protein (or a fragment thereof), may be administered to the host. Following administration, the cell will express the SC-membrane protein (or a fragment thereof) in the host which will in turn lead to the induction of an immune response directed against the SC-membrane protein, polypeptide or fragment thereof.

The vaccine composition provided herein may be prepared in any suitable and pharmaceutically acceptable formulation. It may be provided in the form of an immediately administrable solution or suspension, or a concentrated crude solution suitable for dilution before administration or may be provided in a form capable of being reconstituted, such as a lyophilized, freeze-dried, or frozen formulation.

The vaccine composition may contain a pharmaceutically acceptable carrier in order to be formulated. The carrier typically includes a diluent, an excipient, a stabilizer, a preservative, and the like. Suitable examples of the diluent may include non-aqueous solvents such as propylene glycol, polyethylene glycol, vegetable oil such as olive oil and peanut oil, or aqueous solvents such as saline (for example, 0.8% saline), water (for example, 0.05 M phosphate buffer) containing a buffer medium, and the like, suitable examples of the excipient may include starch, glucose, lactose, sucrose, gelatin, malt, rice, flour, chalk, silica gel, sodium stearate, glycerol monostearate, talc, sodium chloride, anhydrous skimmed milk, glycerol, propylene, glycol, water, ethanol and the like, and suitable examples of the stabilizer may include carbohydrates such as sorbitol, mannitol, starch, sucrose, dextran, glutamate, and glucose, or proteins such as animal, vegetable or microbial proteins such as milk powder, serum albumin and casein. Suitable examples of the preservative may include thimerosal, merthiolate, gentamicin, neomycin, nystatin, amphotericin B, tetracycline, penicillin, streptomycin, polymyxin B and the like.

The vaccine composition of the present disclosure may further contain an adjuvant. The adjuvant may be composed of one or more substances that enhance the immune response to an antigen, e.g., the SC-membrane protein. The adjuvant may function as a tissue reservoir that slowly releases an antigen and/or as a lymphoid system activator that nonspecifically enhances an immune response (Hood et al., Immunology, Second Ed., 1984, Benjamin/Cummings: Menlo Park, Calif., p. 384). Examples of the antigen adjuvant may include complete Freund, incomplete Freund, saponin, gel-type aluminum adjuvants, surface active substances (e.g. lysolecithin, pluronic polyols, polyanions, peptides, oils or hydrocarbon emulsions), vegetable oil (cotton-seed oil, peanut oil, corn oil, sunflower oil, etc.), vitamin E acetate and the like. The adjuvant may consist of mono-phosphoryl lipid A (MPL) from *Salmonella Minnesota* or QS-21, a purified active fraction of the bark of Chilean tree *Quillaja saponaria*.

Among adjuvants applicable to the human body, an aluminum adjuvant is most widely used, and examples of the aluminum adjuvant may include gel-type aluminum salts such as aluminum phosphate, potassium aluminum sulfate, aluminum hydroxide and the like. The aluminum adjuvant is generally known to elicit a Th2-type immune response and enhance vaccine efficacy (Sokolovska A et al., Vaccine. 2007 Jun. 6; 25(23):4575-85; O'Hagan D T and Rappuoli R., Pharm Res. 2004 September; 21(9):1519-30.). Methods of preparing the aluminum adjuvant are known in the art (R. Bomford. Immunological Adjuvants and Vaccines. NATO ASI Series 1989; 179: 35-41; Vogel F R AND Powell M F. Pharm. Biotechnol. 1995; 6: 141-228; Derek T. O'Hagan, Methods in Molecular Medicine. 2000; Apr. 15; 42: 65-90), and the aluminum adjuvant may be used through direct preparation or by purchasing a commercially available product. Examples of commercially available product thereof may include Aluminum hydroxide Gel products (Sigma) and Alhydrogel products (BRENNTAG), in addition to the 2% Alhydrogel (InvivoGen).

The provided vaccine composition may be produced in an arbitrary unit dose. A unit dose refers to the amount of the active ingredient and the pharmaceutically acceptable carrier contained in each product packaged for use in one or more administrations to a subject, such as a human, and an appropriate amount of such active ingredient and carrier is an amount that may function as a vaccine when inoculation with the vaccine composition of the present disclosure is performed one or more times, and such an amount may be determined non-clinically or clinically within the ordinary skill of those skilled in the art.

A method of vaccinating a subject for COVID-19 is provided that includes administering the disclosed COVID-19 vaccine composition to a subject in need thereof. The disclosed vaccine composition may be administered in a number of ways. For example, the disclosed vaccine composition can be administered intramuscularly, intranasally, or by microneedle in the skin. The vaccine compositions may be administered orally, intravenously, subcutaneously, transdermally (e.g., by microneedle), intraperitoneally, ophthalmically, vaginally, rectally, sublingually, or by inhalation. The vaccine composition of the present disclosure may be administered in a controlled release system including, for example, a liposome, a transplantation osmotic pump, a transdermal patch, and the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The dose of the vaccine composition may be determined by a medical practitioner in consideration of patient characteristics such as age, weight, gender, symptoms, complications, and the incidence of other diseases. Further, the temporal interval of administration and the number of administrations may be determined in consideration of the dosage form that is used, the half-life of the active ingredient in the blood, and the like.

The exact amount of the vaccine composition required will vary from subject to subject, depending on the species, age, weight and general condition of the subject and its mode of administration and the like. Thus, it is not possible to specify an exact amount for every composition. However, an appropriate amount can be determined by one of ordinary skill in the art using only routine experimentation given the teachings herein. For example, effective dosages and schedules for administering the vaccine compositions may be determined empirically, and making such determinations is within the skill in the art. The dosage ranges for the administration of the vaccine compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above. In addition to dosing by the ratio of mass-of-vaccine to mass-of-patient, standardized vaccine doses for demarcated demographics can also be used.

Also encompassed by the methods, uses, pharmaceutical compositions and kits of the present disclosure is passive immunization, which is the injection of antibodies or antiserum, previously generated against COVID-19 SC-membrane protein, in order to protect or cure a recipient host of an infection or future infection. Protection fades over the course of a few weeks during which time the active immunization with protein and/or DNA (as described above) will have time to generate a lasting protective response. Serum for passive immunization can be generated by immunization of donor animals using the SC-viral membrane protein, as described above. This serum, which contains antibodies against the antigens, can be used immediately or stored under appropriate conditions. It can be used to combat COVID-19 infections or as a prophylactic (Tuchscherr et al., 2008).

The terms "treat/treating/treatment" and "prevent/preventing/prevention" as used herein, refers to eliciting the desired biological response, i.e., a therapeutic and prophylactic effect, respectively. In accordance with the present disclosure, the therapeutic effect includes one or more of a decrease/reduction in the severity of the disease (e.g., a reduction or inhibition of infection), a decrease/reduction in symptoms and disease related effects, an amelioration of symptoms and disease-related effects, and an increased survival time of the affected host, following administration of the vaccine composition. A prophylactic effect may include a complete or partial avoidance/inhibition or a delay of infection, and an increased survival time of the affected host, following administration of the vaccine composition.

Toxicity or efficacy of vaccine components to elicit an immune response can be determined by standard procedures in cell cultures or experimental animals. Data obtained from cell culture assays and laboratory animal studies can be used in formulating a range of dosage for use in humans. The dosage of such components lies, for example, within a range of administered concentrations that include efficacy with little or no toxicity. The dosage may vary within this range depending upon the dosage form employed and the route of administration utilized.

The vaccine compositions may, if desired, be presented in a pack or dispenser device which may contain one or more-unit dosage forms containing the SC-membrane protein. The pack may for example include metal or plastic foil, such as a blister pack. The pack or dispenser device may be accompanied by instructions for administration to subjects, especially humans. Associated with such container(s) can be a notice in the form prescribed by a governmental agency regulating the manufacture, use or sale of pharmaceuticals or biological products, which notice reflects approval by the agency of manufacture, use or sale for human administration. Thus, a kit is provided that includes the SC-membrane protein as described herein. In one specific aspect the kit further includes instructions for the treatment and/or prophylaxis of COVID-19.

In still yet another aspect of the present disclosure, a composition and method for detecting a coronavirus-specific antibody, that includes the SC-membrane protein is provided. The detection composition of the present disclosure serves to detect a coronavirus-specific antibody, especially a Spike (S), envelop (E) or membrane (M) antigen-specific antibody, in a subject sample, and the composition of the present disclosure is able to distinguish coronavirus-infected and uninfected subjects from each other by bringing the same into contact with a sample and measuring the extent of reaction therebetween. In particular, this composition may be useful to distinguish whether a patient with symptoms identical or similar to those of coronavirus disease is infected with coronavirus during the period of risk of onset of coronavirus disease. In a specific embodiment the coronavirus is COVID-19.

As used herein, the term "specific binding" means that the SC-membrane protein, specifically binding to a coronavirus-specific antibody, especially a COVID-19 antigen-specific antibody, binds only to the antibody and does not substantially bind to other proteins. Here, the term "substantially" means that nonspecific binding, the extent of which is low, may occur, and such nonspecific binding may be removed by washing using a washing solution before detection of specific binding as described below.

As used herein, the term "sample" refers to a sample in which a coronavirus-specific antibody, especially a SC-membrane binding protein antigen-specific antibody, may exist, and includes the blood, serum, plasma, saliva, tears, mucus, nasal mucus and the like.

In one aspect, the SC-membrane protein is in the form of being dissolved in a soluble solution, for example, a carbonate buffer solution or a bicarbonate buffer solution, or in a lyophilized form. In another aspect, the SC-membrane protein is fixed to a support, and examples of the solid support that may be used may include, but are not limited to, particles (resin beads, magnetic beads, metal microparticles, gold colloids, etc.), substrates (microtiter plates, glass substrates, silicon substrates, resin substrates, electrode substrates, membranes, etc.), and the like. Methods of fixing the SC-membrane protein of the present disclosure to the support may include direct fixation through adsorption (e.g. coating) or indirect fixation using a linker that binds both to the protein and the support.

When the support is treated with a sample, the SC-membrane containing support can form a complex with a coronavirus-specific antibody, especially a SC-membrane protein specific antibody, contained in the sample. After induction of the complex formation, in order to remove nonspecifically bound antibodies or contaminants, washing may be performed using a washing buffer such as Tween 20 or a washing agent such as distilled water.

The SC-membrane protein/antibody complex may be detected through any of various methods, whereby the presence or absence and/or the concentration of a coronavirus-specific antibody, especially a SC-membrane protein specific antibody, in the sample may be qualitatively and quantitatively determined. This will provide useful information as to whether the subject is infected with coronavirus.

The SC-membrane protein/antibody complex may be detected using a detection agent, and the detection agent may be, for example, a secondary antibody binding to a coronavirus-specific antibody, especially a SC-membrane protein specific antibody. Examples of the secondary antibody may include those that recognize the Fc portion of the antibody (primary antibody).

The secondary antibody may be conjugated with a label or an enzyme that provides a detection signal, thus facilitating detection. Label conjugation serves to bind any label capable of providing a detection signal to the antibody. Examples of the label may include radioisotopes such as tritium, iodine ($^{131}$I, $^{125}$I, $^{123}$I, $^{121}$I), phosphorus ($^{32}$P), sulfur ($^{35}$S), metals (e.g. $^{68}$Ga, $^{67}$Ga, $^{68}$Ge, $^{54}$Mn, $^{99}$Mo, $^{99}$Tc, $^{133}$Xe) and the like, fluorescence substances or fluorophores such as fluorescein isothiocyanate, tetramethyl rhodamine isothiocyanate, substituted rhodamine isothiocyanate, dichlorotriazine isothiocyanate, Alexa or AlexaFluoro, and the like.

Enzyme conjugation serves to bind an enzyme such as peroxidase (POD), alkaline phosphatase, β-galactosidase, urease, catalase, glucose oxidase, lactate dehydrogenase, amylase or a biotin-avidin complex to the antibody, and these enzymes provide a certain detection signal when reacting with a certain substrate. For example, peroxidase shows a purple color when reacting with aminosalicylic acid and hydrogen peroxide or p-phenylenediamine and hydrogen peroxide, alkaline phosphatase shows a yellow color when reacting with dinitrophenylphosphate, and β-galactosidase shows a purple color when reacting with β-nitrophenyl-β-D-galactopyranoside. The label or enzyme may be covalently bonded to the antibody.

Upon detection using the detection agent such as the secondary antibody or the like, the extent of reaction of the secondary antibody with the complex may be measured through a variety of immunoassay methods well known or publicly known in the art, such as enzyme immunoassay, fluorescence immunoassay, radioimmunoassay, luminescence immunoassay, and the like. In a specific embodiment, an enzyme immunoassay, for example an ELISA (enzyme-linked immunosorbent assay), is used.

A further aspect pertains to a diagnostic kit for detecting a coronavirus-specific antibody, especially a SC-membrane protein antigen-specific antibody. The detection kit of the present disclosure includes the SC-membrane protein. The SC-membrane protein contained in the kit may be provided in the form of being attached to or detached from a support or may be provided in a dissolved form in a soluble solution or in a lyophilized form.

The diagnostic kit may further include a detection agent for detecting a complex of the coronavirus-specific antibody, especially the SC-membrane protein antigen-specific antibody, in the sample and the SC-membrane protein specifically binding to the specific antibody. The detection agent may be a secondary antibody conjugated with the label or enzyme described above.

Furthermore, the diagnostic kit may further include a carrier, a washing buffer, a diluted sample solution, an enzyme substrate, and a reaction stop solution, and may also include instructions to teach the method of use, including a method of analysis of the results, etc.

Still a further aspect pertains to a diagnostic method of detecting a coronavirus-specific antibody, especially a SC-membrane protein antigen-specific antibody, in a biosample. The method includes (a) contacting a sample with the SC-membrane protein composition for detecting a coronavirus-specific antibody, and (b) detecting the complex. In an embodiment, the biosample in step (a) is serum.

Also, in the diagnostic method, the detecting the complex in step (b) includes reacting a secondary antibody conjugated with a label or an enzyme capable of providing a detection signal with the complex and measuring the extent of reaction with the complex. The extent of reaction of the secondary antibody with the complex may be measured through enzyme immunoassay, fluorescence immunoassay, radioimmunoassay, luminescence immunoassay, etc., as described above. In a specific embodiment, an ELISA (enzyme-linked immunosorbent assay) is used.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Example

The designed SC-SEM-membrane protein complex links three membrane proteins of SARS-CoV-2 in the single polypeptide chain, which will be used to advance vaccine designs through inclusion of one or more antigenic sites, increasing immunogenicity, and producing comprehensive antibodies (not just inhibiting S-protein binding to ACE2, but also blocking the E-protein ion channel and M-protein membrane assemble functions) (Table 1). Thus, provided is an innovative vaccine design with stronger immune protection for COVID-19, compared to that of single S-protein-based gene and recombinant vaccines.

In the past, novel single-chain membrane enzyme complexes have been constructed using unique membrane-bound helix peptides 10aa or 22aa (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740). The sequences of the 10aa and 22aa are not antigenic because they are adopted from the transmembrane domains of the human rhodopsin, but they are compatible with membrane proteins spanning through membrane. Previous SC enzyme complex linked by the 10aa or 22aa adopted native protein conformation and displayed superior biological activities which have been confirmed by the studies from cell expression to transgenic mice (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653; Deng Y et al., 2016, Nat Commun. 15:11276). Based on these experiences, SC-SEM proteins of COVID-19 are constructed using such linkers. Genome map and size (29903 bases) of SARS-CoV-2 have been solved (FIG. 1B). This information has provided data for establishing a method linking the encoded S-, E- and M-proteins together using the 10aa or 22aa linkers as shown in a carton (FIG. 1C).

Figure 2:
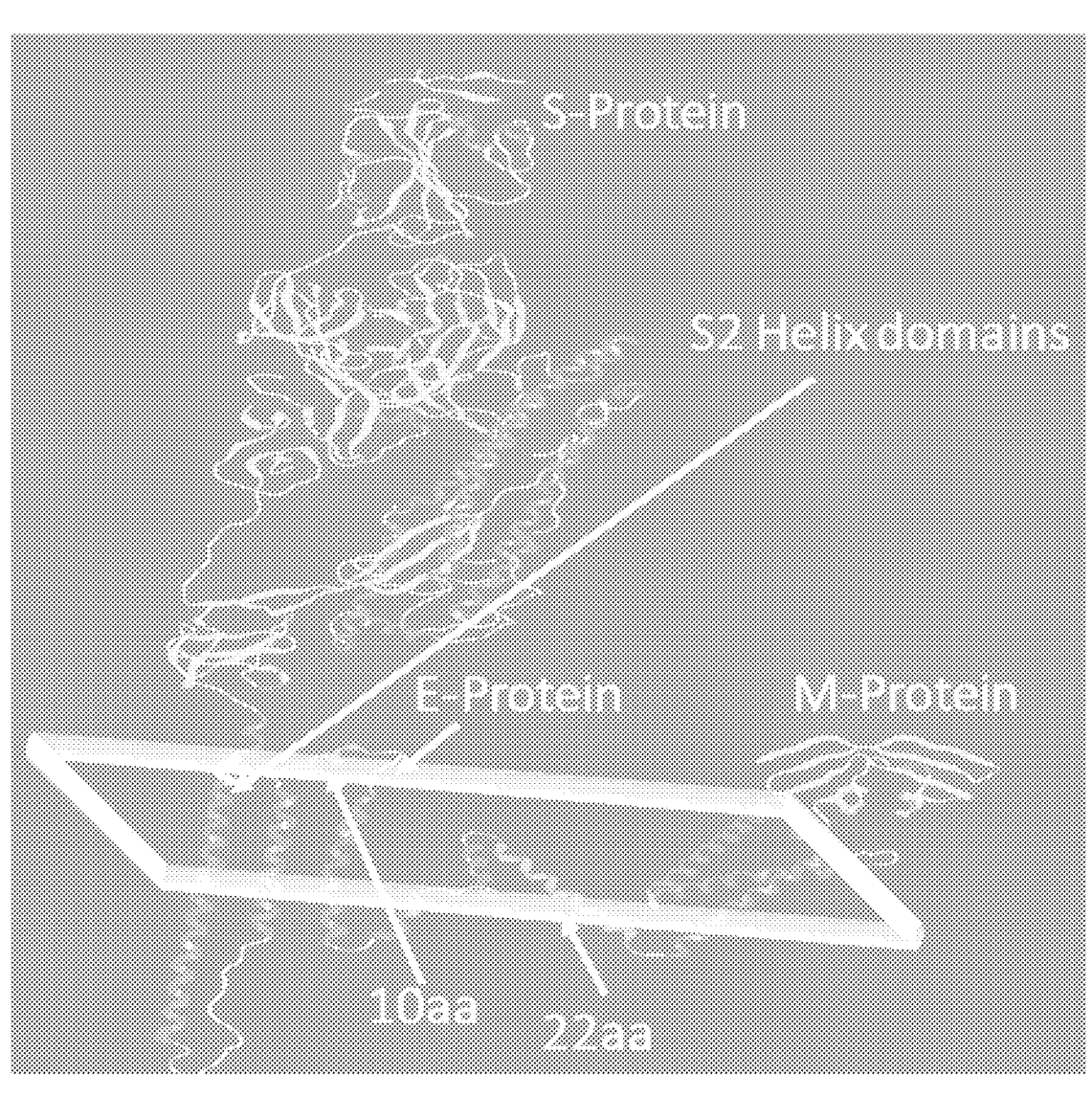
FIG. 2. COVID-19 SC-SEM-1 model. S-protein 3D structure was obtained from Cryo-EM structure (Markus Hoff-mann M et al., 2020, Mol Cell. 78: 779-784). Structures of S2 helix domains and E-protein were constructed using coronavirus NL63 structure (PDB: 2IEQ), and NMR structure for SARS (Kamimura K et al., 2011, Advances in Gene Delivery Systems". Pharmaceutical Medicine. 25: 293-306) through homology modeling, respectively. M-protein structure was obtained from published data (Berk A J. Adeno-viridae. In: Knipe D M, Howley P M, editors. Fields Virology. Philadelphia, PA: Lippincott Williams & Wilkins; 2013. pp. 1704-1731). The helical 10aa and 22aa structures (from human rhodopsin) were used to link the three proteins together. The 3D rectangle box represents the viral membrane.

In order to produce the SC-SEM protein without altering protein folding configuration and membrane-bound stabilities, the reported 3D structures of the S-, E- and M-proteins (FIG. 2) were used to create a structural model. From the known transcription order of the genome map (FIG. 1B) and topological arrangement (FIG. 1C) of the three proteins on viral membrane, a linkage from S to E and then to M proteins was established. In this configuration, the first linker (such as 10aa or 22aa) could span through the membrane linking the C-terminus of S-protein to the N-terminus of E-protein. And then another 10aa or 22aa could span through the membrane linking the C-terminus of the S-E complex to the N-terminus of the M-protein (FIG. 2). To test the SC-SEM configuration and membrane spanning using computational simulation, it has been determined that additions of Prolines at the termini of the 10aa or 22aa an provide smooth turns for the linkage. The transmembrane (TM) linker, 22aa may stabilize all of the three membrane proteins spanning the lipid bilayer to mimic their native protein folding and topology (FIG. 2). It should be noted that E-protein has ion channel activity that is involved in maintaining the viral survival and promoting viral pathogenesis (Regla-Nava, J et al., 2014, PLos Pathog. 10: e1004077), and the M-protein is involved in the viral membrane assembly for viral proliferation and survival. The first SC-SEM protein could be cloned and expressed in human cells using the similar viral and nonviral vectors as for previous SC enzyme complexes (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653; Deng Y et al., 2016, Nat Commun. 15:11276).

1615 amino acid residues, which include wild type S, E, M and 10aa and 22aa linkers (FIG. 2) are shown in FIG. 3. Although, S-wild type protein may be initially used, some S-protein designs may use mutated S1/S2 in the multi-basic residue cleavage site (Hoffman, M, 2020, Mol Cell 78:779-784). The antigenicity can be tested after the wild type protein is successfully expressed.

The constructed SC-SEM-1 complex vaccine for COVID-19 will be used as an example to build additional models by different sequence configuration and linkers. The S-, E- and M-proteins of the COVID-19 may be linked together through two possible directions (SC-SEM and SC-MES) by two defined and tested transmembrane linkers to form SC membrane protein complexes to mimic the whole antigenic sites of the membrane proteins of the wild-type virus.

Currently, most vaccine designs for COVID-19 are focused on the S-protein, which is responsible for binding and invading host cells (Wold W S M et al. editors, 2013, Fields Virology. Philadelphia, PA; Lippincott Williams & Wilkins, pp. 1732-1767). The advantage of presently disclosed vaccine is that it is easy and fast to develop using recombinant protein or gene delivery of cDNA or mRNA. This is in contrast to vaccines developed from a single S-protein which include: (i) limited antigenic sites and low antigenicity as a single protein antigen compared to that of the entire viral membrane protein complex; (ii) possibility the virus is not killed because the anti-S-protein antibody does not block E-protein ion-channel activity nor M-protein viral membrane assembly, which are necessary for viral survival and proliferation; and (iii) possibility of not working once the S-protein has mutated. Based on this information, provided herein is an expectedly more effective vaccine for comprehensive protection from COVID-19 infection based on the design and use of a single-chain (SC) entire viral membrane protein complex. The SC-membrane protein will make the vaccine design suitable for single molecule-based recombinant protein production and single cDNA or mRNA gene delivery.

The SC molecular weight (including S-, E- and M-proteins and two linkers, FIG. 2) is approximately 180 kDa (1606-1618aa). Based on currently available molecular biology techniques, known to those of skill in the art and as described above, the cDNA, mRNA and recombinant protein of the 180 kDa protein can be produced easily for use in vaccine compositions. See, for example, engineering SC membrane protein complex for enzymes and receptors (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653; Deng Y et al., 2016, Nat Commun. 15:11276). Specifically, the membrane-spanning helical 10aa or 22aa linker that stably links the membrane proteins together has been characterized in previous studies (using in vitro and in vivo approaches) (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653; Deng Y et al., 2016, Nat Commun. 15:11276). These methods may be applied to the designed SC-viral membrane protein complex. Such 10-amino acid and 22-amino acid linker sequences may further be used as general linker sequences in fusion/chimeric proteins including those unrelated to coronavirus proteins.

In order to find a suitable SC-membrane protein for vaccination, four designs may initially be created and tested. 10aa and 22aa linkers at two different N- to C-terminal directions linking S-, E-, and M-protein together have been established (Table 2). SC-SEM-1 and -2 represent the one direction of viral membrane protein genome arrangement (FIG. 1). SC-MES-1(R) and SC-MES-2(R) represent the reverse direction of genome arrangement (FIG. 1). The established model of the SC-SEM-1 (FIGS. 2 and 3) which will be used as a model to establish the additional three models proposed in Table 2.

The 3D structural conformation of the four different SC-membrane protein complexes can be constructed by modeling as described in FIG. 2. The steps used for creating 3D model of SC-SEM-1 shown in FIG. 2 will be adopted for construction of the SC-SEM-2, SC-MES-1(R) and SC-MES-2(R) models. A fully equipped computational workstation with a commercial software package (Ling Q L et al., 2018, Sci Rep 26:1653; Deng Y et al., 2016, Nat Commun. 15:11276) has been used previously.

With regard to comparison of the exposures of the protease cleavage site and stability of the SC-complex, optimized designs may be reasonably predicted by having minimal protease-cleavage site exposure on the surface. Thus, the four versions of the SC-viral membrane protein complexes can be compared after energy minimization and dynamic studies for protease cleavage site exposure and be ranked for stability accordingly.

The general protein folding and membrane spanning of the constructed SC-SEMs and SC-MESs can be predicted by hydrophobicity calculation and the 3D modeling. The 10aa and 22aa linkers have previously been identified as transmembrane helix linkers. Thus, the membrane span prediction should be easily obtained. The scores with the most similar membrane span compared to the wild type S-, E-, and M-proteins will be established. The 3D structural models and the scores for stability and membrane span topologies will be established and ranked.

Molecular cloning and expression of recombinant SC-SEMs and SC-MESs can be established using HEK293 cell lines. The correct protein folding, topological arrangement, stability and expression efficiency of the different SC-viral membrane-protein complexes will be ranked by multiple methods including immunocytochemistry staining, MALDI-TOF mass spectrometry, immunodiffusion, Western blot and size-exclusion chromatography.

In the past, methods have been established to successfully engineer, clone, and express the SC-membrane protein complexes using different vectors and cell lines such as, human cell lines, yeast and E. Coli cells, (see, for example, Ruan K H et al., 2006, Biochemistry 45::14003-11; Ruan K H et al. 2008, Arch Biochem Biophys, 480:41-50; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653) and may be used to express the COVID-19 proteins disclosed herein. For example, the vector, pcDNA3.1, suitable for HEK293 cell expression may be used for expression of the newly created SC-SEMs and SC-MESs. Thus, the SC-viral membrane-protein complexes may be cloned into the pcDNA3.1 vector and expressed in human HEK293 cell line using established approaches (Ruan K H et al., 2008, FEBS J. 275: 5820-5829; Ruan K H et al., 2009, Protein Eng Des Sel. 22:733-740).

Sub-cloning the cDNAs of the created SC-SEM and SC-MES membrane protein complexes may be achieved using the pcDNA3.1 vector with His tag. The cDNAs of the individual SC-SEM protein complexes (Table 2) can be obtained by synthetic cDNA and PCR approaches, and then sub-cloned into the vector of pcDNA3.1 for HEK293 cell expression. All successful cloning can be confirmed by cDNA sequencing (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740).

Expression of recombinant SC-SEM and SC-MES membrane protein complexes may be accomplished using HEK293 cells. HEK293 cells have been widely used to express recombinant proteins for characterization of their biological activities. The experimental procedures used for previous hybrid enzymes and receptors (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740) may be used.

The yield and stabilities of HEK293 cell-expressed SC-SEMs and SC-MESs can be compared by Western blot. Their immunogenicity will be further ranked by titer assays of immunodiffusion, and sandwich immune assay using commercially available polyclonal anti-S-protein antibodies. Companies providing polyclonal anti-SARS-CoV-2 antibodies for the such tests include, for example, RayBiotech Life, MyBioSource, Thermofisher, and Creative Biogen.

The highest expression yield and antigenicity titer of four SC-SEMs and SC-MESs produced in human HEK293 cell line can be identified. The best SC-viral membrane-protein design suitable for human cell line expression may be identified for further vaccine development.

The recently developed system of the high yield expression of SC COX-2-10aa-PGIS using adenovirus vector transfected HKE293 cells can be applied to the SC-SEM and SC-IVIES complexes expression and characterization. The most commonly (more than 65%) used gene delivery systems for human cells are based on adenovirus (Ad), retrovirus, poxvirus, adeno-associated virus (AAV), and herpes simplex virus (HSV) (Brunetti-Pierri et al., 2011, Hum Mol Genet. 20:7-13; Wold, W S M et al., 2013, Curr Gene Ther. 13:421-433). Currently, the majority of COVID-19 vaccine development and clinical trials use viral vector-based technology. The most used viral vector is an Ad virus-based design. Recently, large SC-enzyme complexes, such as COX2-10aa-PGIS has been done using Ad-vector expression system on HEK293, and COS-7 cells. The results have showed that the Ad-virus system gave more than ten-folds higher expression efficiency than that of the pcDNA3.1 (FIG. 4). It should be noted that the data shown in FIG. 4 were obtained using the genetically modified versions of replication-defective (RD) Ad5 with the essential E1A and E1B genes deleted and replaced by an expression cassette with a high activity promoter such as CMV promoter. The genetically modified Ad genome and the vectors are grown on complementing cell lines such as HEK293 (Wold, W S M et al., 2013, Curr Gene Ther. 13:421-433). This system may be directly applied to the gene delivery of Ad5-cDNA-based COVID-19 vaccination once gene expression is successfully established in the HEK293 cells.

The cDNAs of the individual SC-membrane protein complex (Table 2) will be obtained by synthetic cDNA and PCR approaches and then sub-cloned into Ad5-vectors for HEK293 cell expression. All successful cloning will be confirmed by cDNA sequencing (Ruan K H et al., 2006, Biochemistry 45::14003-11; Ruan K H et al. 2008, Arch Biochem Biophys, 480:41-50; Ruan K H et al., 2008, FEBS J. 275: 5820-5829; Ruan K H et al., 2009, Protein Eng Des Sel. 22:733-740; Ling Qing-Lan et al. 2018, Sci Rep 8:1653; Vollert Craig et al., 2004, Behav Brain Res 258: 10; Liu Qu et al., 2013, J Cell Physiol. 227:2907-2916; Li Y et al., 2019, J Cell Mol Ned. 23:8343-8354; Ling Q L et al., 2018, Sci Rep 26:1653; Deng Y et al., 2016, Nat Commun. 15:11276). His-tag will be added to the sequences for affinity purification.

The yields and antigenicity of the Ad5 vector-driven gene expression of the SC-SEM and SC-IVIES membrane protein complexes on HEK293 may be compared by immunocytochemistry staining, Western blot, immunodiffusion, and ELISA using commercial polyclone anti COVID-19 antibodies as described above. In addition, the dose-responses for viral expression will be further established for the highest yield and titer for the best SC-membrane protein complex design. The Ad5-mediated transfection and expression is expected to advantageously increase the yield of the SC-membrane protein complex in the human cells. The results will provide strong support for the SC-membrane protein complex of COVID-19 as an Ad5-vector-based cDNA vaccine candidate.

The SC-protein complex with the highest expression yield and binding to the different polyclonal anti-COVID-19 antibodies may be selected for engineering the first lipid nanoparticle-based SC-viral membrane protein complex vaccine immunized on mouse model.

Figure 5:
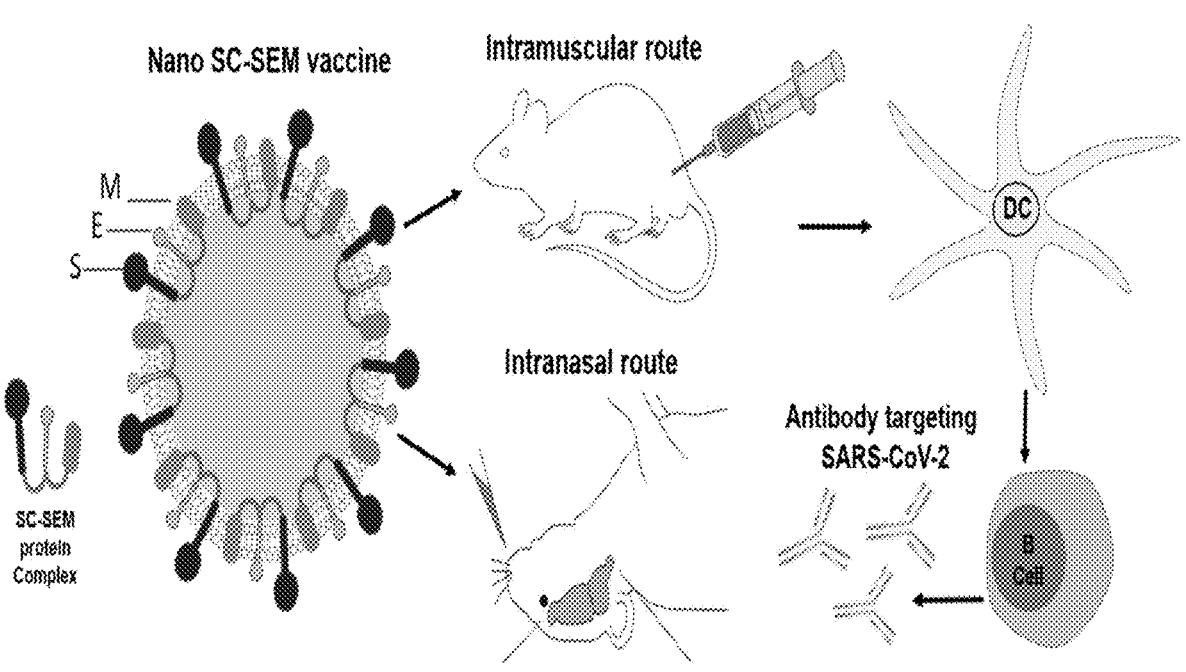
FIG. 5. Schematic of nano SC-SEM vaccination.
Figure 6:
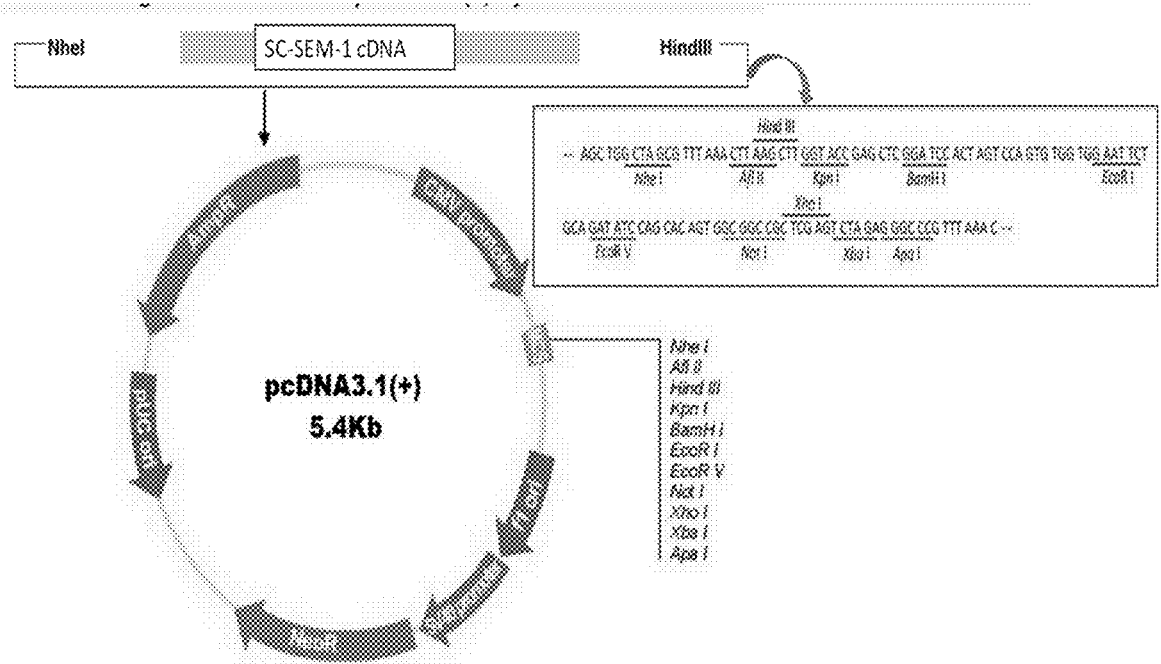
FIG. 6. Use of SC-SEM-1 cDNA for construction of a SC-SEM-1 protein expression vector, pcDNA-3.1-SC-SEM-1. The cDNA of the designed SC-SEM-1 was successfully obtained using DNA synthesis and PCR approaches and cloned into pcDNA3.1(+) vector.
Figure 7:
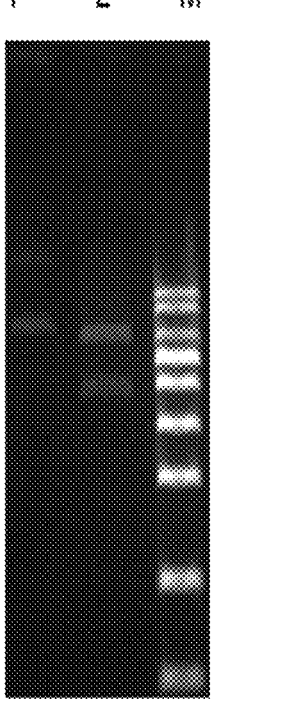
FIG. 7. Verification of the Cloned Plasmid (pcDNA3.1-SC-SEM-1) by restriction enzyme digestion.
Figure 8:
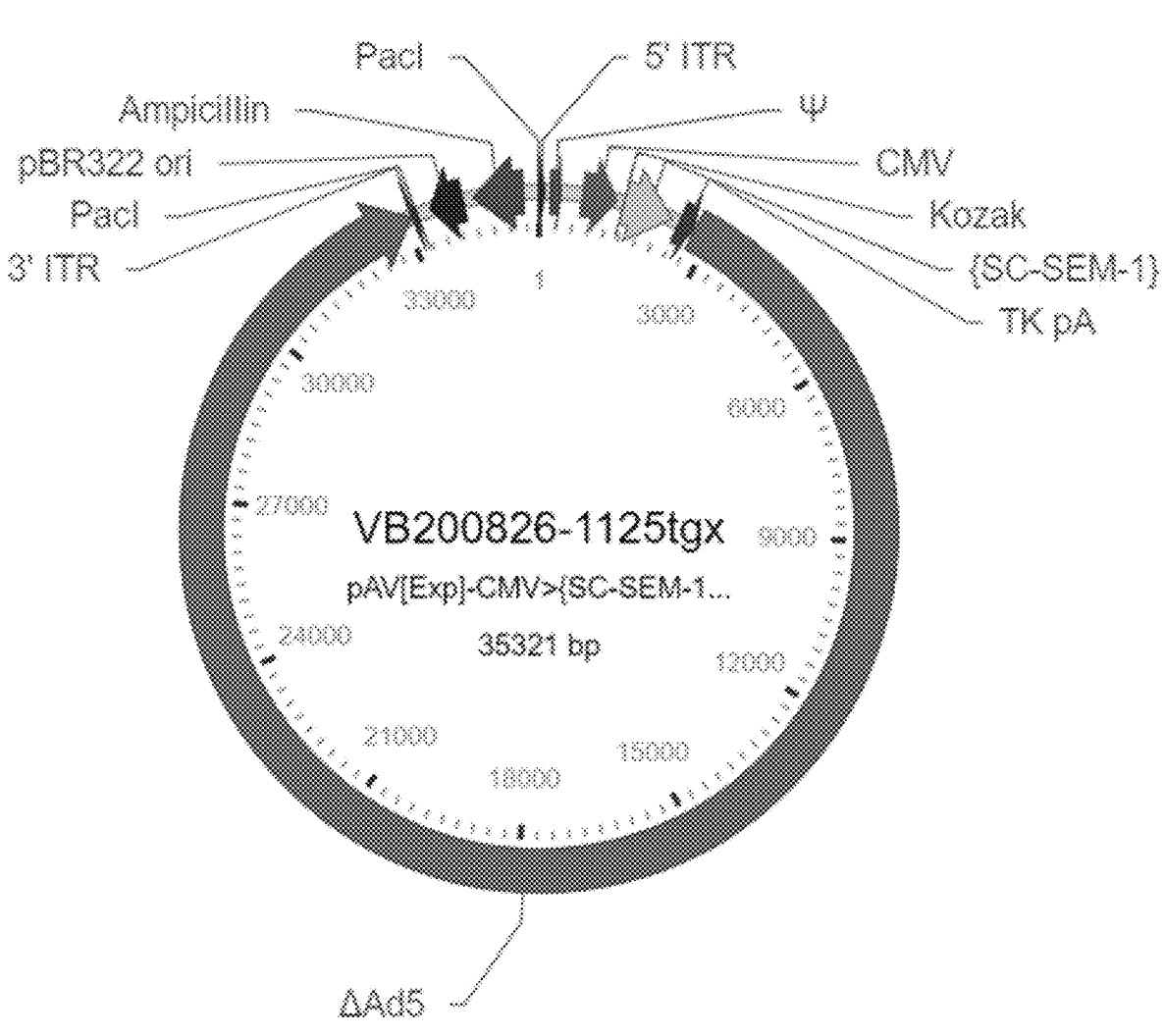
FIG. 8. Constructed viral (adenovirus) expression vector for SC-SEM-1 suitable for in vivo expression. The constructed expression vector contains following main components: 5' ITR: Adenovirus 5' inverted terminal repeat; Ψ: HIV-1 packaging signal; CMV Promoter Human cytomegalovirus immediate early enhancer/promoter; Kozak: Kozak translation initiation sequence; SC-SEM-1: our new cDNA of SC-SEM-1; TK pA, PolyA_signal Herpes Simplex Virus thymidine kinase polyadenylation signal; AAd5: Deleted adenovirus serotype 5 genome sequence; 3' ITR: Adenovirus 3' inverted terminal repeat Pact Pad restriction site; pBR322: pBR322 origin of replication Ampicillin: Ampicillin resistance gene and Pact Pad restriction site.

In general, immunogenicity could be increased by the number of antigenic sites on the protein, which increases as the protein size increases. It has been suggested that S-protein-induced immunization may not last as long as that of the native SARS-CoV-2 virus (Amanat F et al. 2020, Immunity 52:583-589; Ravichandran S et al., 2020, Sci Trans Med. 12:550). This is highly possible because a single S-protein vaccine is weaker than that of an inactivated total virus, which contains three membrane proteins S-, E-, and M-proteins. Accordingly, the disclosed SC-SEM and SC-MES which contain all three membrane proteins, may mimic all of the antigenic sites of the native SARS-CoV-2. Non-viral nanoparticles have emerged as powerful tools to initiate and modulate immune responses due to the inherent ability of nanoparticles to target antigen-presenting cells and facilitate the antigen retention and presentation (Kishimoto T K et al., 2018, Front Immunol 9:230; Johnson L et al., 2020 Vaccines 8:E237; Kratzer B et al., 2020, Eur J Immunol 50: 17-32). The disclosed SC-viral membrane protein complexes contain multiple transmembrane domains that can insert in the lipid bilayers and attach on the surface of nanoliposomes in a repetitive array manner, thus displaying the viral antigens in a way the immune system may strongly respond to (FIG. 5). Thus, it is believed that the SC-viral membrane protein complexes-coated nanoparticles may induce stronger and longer immune responses than that of the single S-protein-based vaccine in vivo.

Purified SC-SEM and SC-MES protein complex from the Ad5-vector expression system may be used for immunization. The SC-protein may be easily purified via ion-exchange and size exclusion column and affinity-purification using the His-tag. See for example, previous large-scale SC-enzyme purification method (Ruan K H et al. 2008, Arch Biochem Biophys, 480:41-50).

A biomimetic nanoliposomal nanoparticles (NP) carrying monophosphoryl lipid A (MPL) from *Salmonella Minnesota* may be used as a vaccine adjuvant. The nanoliposomes are composed of DPPC/DPPG/DPPE-PEG/Cholesterol at 10:1: 1:1 molar ratio. MPL (50 μg), a FDA approved vaccine adjuvant used in SHINGRIX vaccine (50), will be added to lipids mixture to form lipid film under vacuum and nanoliposomes (~100 nm) will be prepared as done previously (Qhattal H S et al., 2014, ACS Nano. 8:5423-40; Qhattal H S et al., 2011, Mol Pharm. 8:1233-46). Briefly, purified SC-SEM or SC-IVIES protein complex will be solubilized in 10 mM HEPES buffer (pH 7.2, with 2% SDS) to a final concentration of 0.2 mg protein/ml. This protein solution will be used to solubilize the lipid film. The detergent-protein solution will be extensively dialyzed against PBS, pH7.4 for 72 h at 4° C. and then subjected to sonication to induce vesicle formation. Insoluble material will be removed by centrifugation. The zeta potential will be monitored of SC-protein-NPs as the surface charge will be different from that of blank NP. The presence of small unilamellar nanoparticles will be confirmed by electron microscopy as previously described (Fofaria N M, 2016, Int J Pharm 498:12-22; Qhattal H S et al., 2011, J Agric Food Chem 59:12396-404).

The best designs with the highest yield of the SC-protein produced from HEK293 cells in each group will be selected for animal immunization after incorporated into the nanoparticles with adjuvants. Normal BALB/c mice; Ages: 5-7 weeks; and males and female will be tested. The BALB/c mice is immunocompetent and has been extensively used for the pre-clinical evaluation of vaccines. The untreated mice and commercial S-protein will be used as controls. BALB/c mice will be injected intramuscularly (IM, quadriceps, n=10) with a 50 μL of nanovaccine containing protein dose of 1, 5, 10 ug/mouse. Two immunization will be scheduled for two injections at day 1 and day 60. For the lead vaccine mucosal immunity will also be tested via intranasal immunization (FIG. 5).

For characterization of the antibody titers after vaccination, 100 μl of blood from each group will be collected and the titers of the antibody produced by the vaccination on mice will be quantified by IgG, IgG1, IgG2 titer detection of ELISA using individual and mixed S-, E-, and M-proteins as antigens (Creative Biogen, Inc.). The nasal lavage and lung lavage fluids will also be collected for IgA detection by ELISA. The titer will be compared with that of the single S-protein immunized animal. Immunogenicity will be ranked through the comparison. The mouse sera samples will also be used for cytokine response assays (ProcartaPlex Immunoassay).

To compare the duration of antibody production, the immunized animal blood will be collected after one month of the last immunization, and then recollected every month up to 8-10 months. The quantitated antibody titers will be compared.

Twenty mice (10 each sex)/group of the individual SC-SEM and SC-MES membrane protein immunizations will provide the initial statistical data for the recommendation of the best candidates for further vaccine development. The antibody produced from the best SC-SEM and SC-MES to effectively neutralize three of S-, E-, and M-proteins will be established. The in vivo results will provide strong support for developing a COVID-19 vaccine using the new constructed SC-viral complex.

Alternative expression systems include, for example, the yeast pYES2 expression system. As an alternative to coated nanoliposomes the SC-protein may be adsorbed to the FDA approved aluminum hydroxide gel. Efficacy may also be increased by adding a booster shot and/or fine tuning the nanovaccine formulation.

Example 2

The single-chain multiple protein vaccine techniques disclosed above may also be used to construct SC-variants comprising the same protein subunits but derived from SARS Cov-2 variants. A number of SARS Cov-2 variants have been identified and some of the variants have been shown to have increased viral spreading capability and toxicity. For example, the variants of alpha variant (UK, B1.1.7/501Y), Beta variant (South Africa B.1.351/502Y), Gamma Brazil. P.1/501Y and New York, B.1.526, and Delta variant (Indian variant), B.1.617.2, T478K, L452R) are likely more toxic and with different degrees of resistance to current wild-type vaccine. The disclosure herein could be used to link >2 (up to 10) multiple variants for the S proteins, RBDs or RBMs of the S-proteins, or other related viral proteins and domains.

Figure 9A:
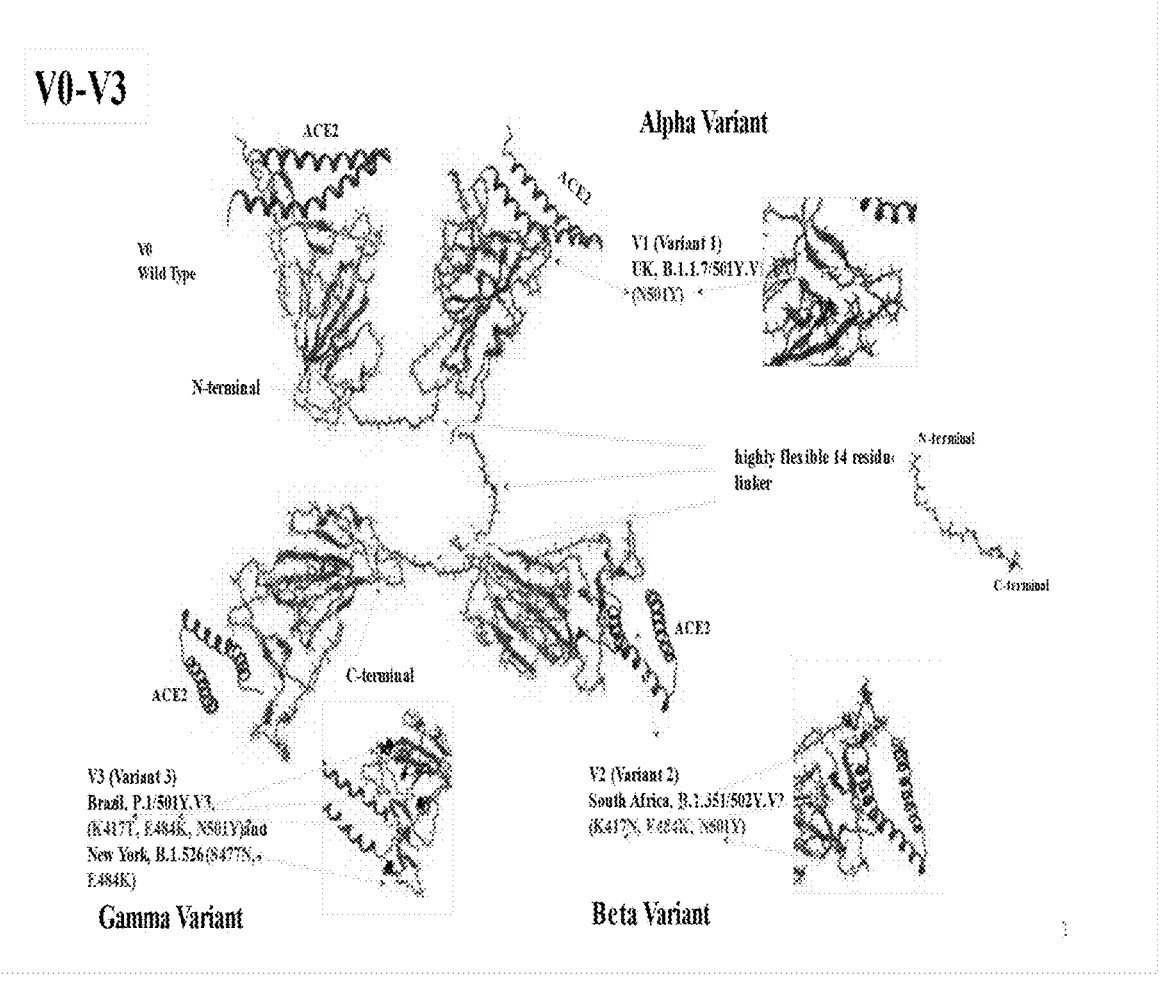

FIG. 9A-B. depicts the construction of a 3D-structural model (A) and amino acid residues (B) of single-chain four RBD variants (V0-V3) as a comprehensive COVID-19 variant vaccine. The four RBD domains including wild type (V0), Alpha variant (UK variant (V1)), Beta variant (South Africa variant (V2)), the combination of Gamma variants (Brazil P.1/501Y) and New York, B.1.526 (V3) were linked together by three of the highly flexible linkers (14 amino acid residues:

*PTIKPSPPSKSPAP*: SEQ ID NO 16).

The constructed four RBD variants become a SC-polypeptide. The 3D-structure of RBD binding to ACE2 adopted from PBD 7E3J were used as templates.

Figure 10A:
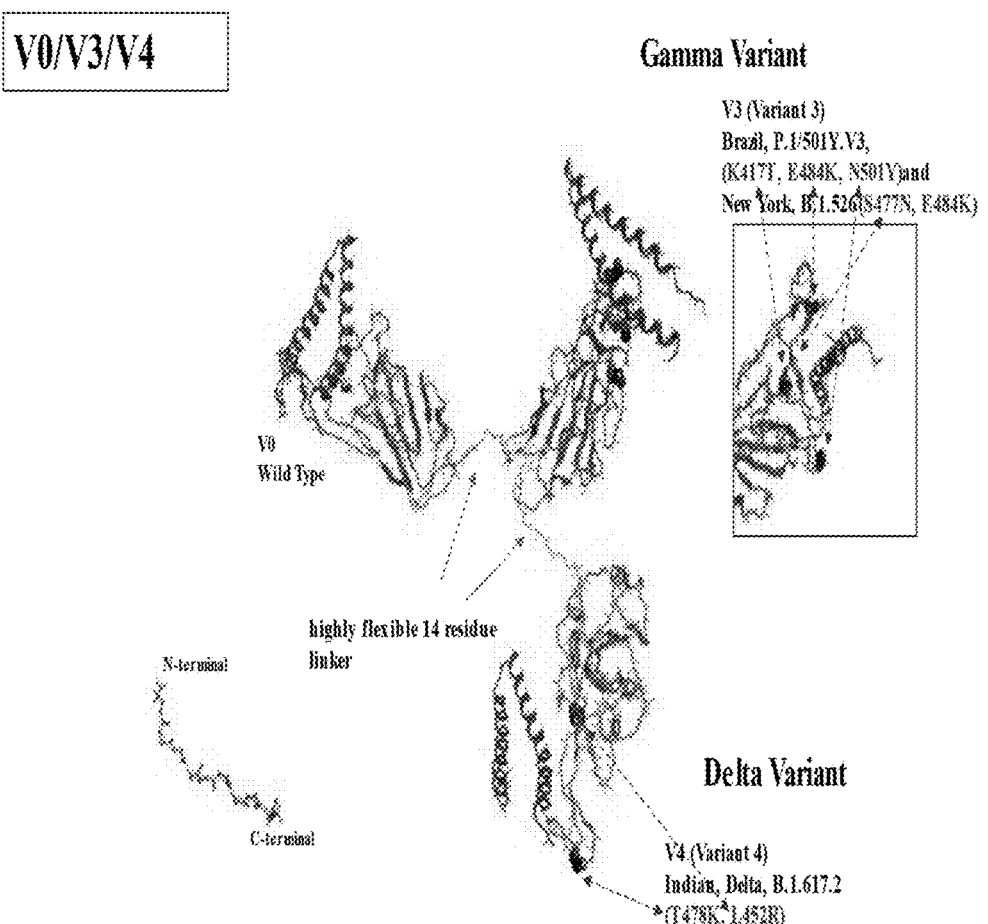

FIG. 10A-B. depicts the construction of a 3D-structural model (A) and amino acid residues (B) of SC-RBDs with three variants (Vo/V3/V4) as a comprehensive COVID-19 variant vaccine. The three RBD domains including wild type (V0), the combination of Gamma variant (Brazil P.1/501Y) and New York, B.1.526 (V3) and Delta variant (Indian variant), B.1.617.2, T478K, L452R (V4) were linked together by one of the highly flexible linkers (14 amino acid residues:

*PTIKPSPPSKSPAP*: SEQ ID NO 16).

The constructed three RBD variants become a SC-polypeptide. The 3D-structure of RBD binding to ACE2 adopted from PBD 7E3J were used as templates.

Figure 11A:
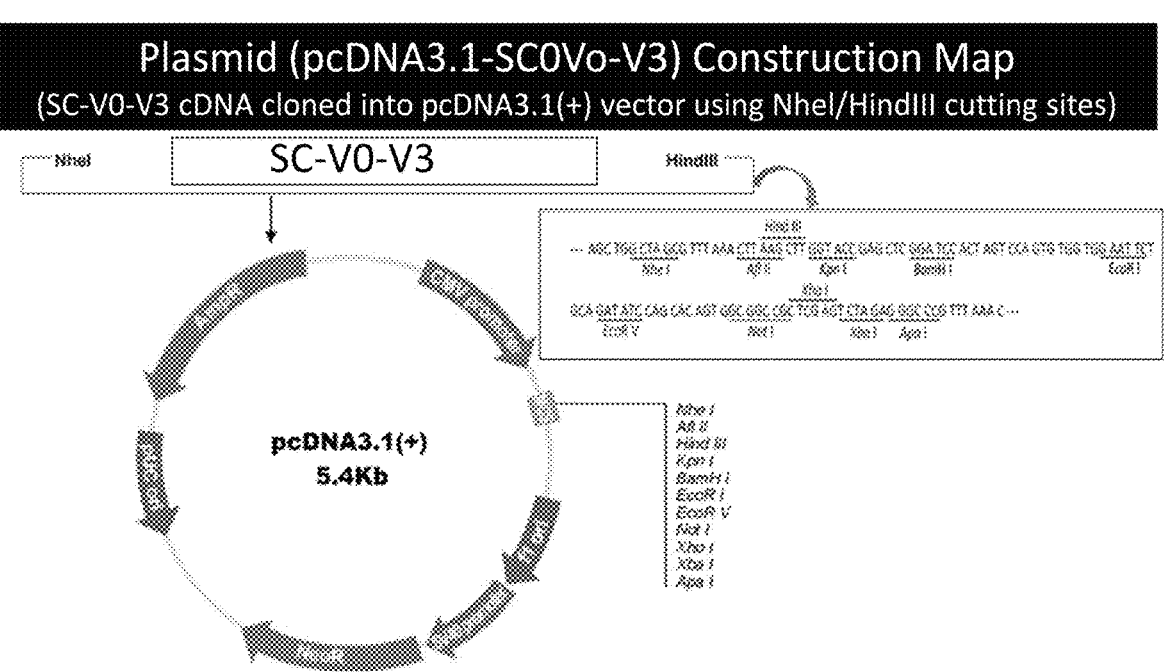
FIG. 11A-B. Depicts examples of prepared plasmids for producing SC-V0-V3 (FIG. 11A) and SC-V0/V3/V4 (FIG. 11B) vaccines. The cDNAs of the SC-V0-V3 (A) or SCOV0/V3/V4 were synthesized and then subcloned into pcDNA3.1 (+) vector to form expression plasmids suitable for preparation of the vaccines designed in mammalian cells and tissues and in vivo.
Figure 11B:
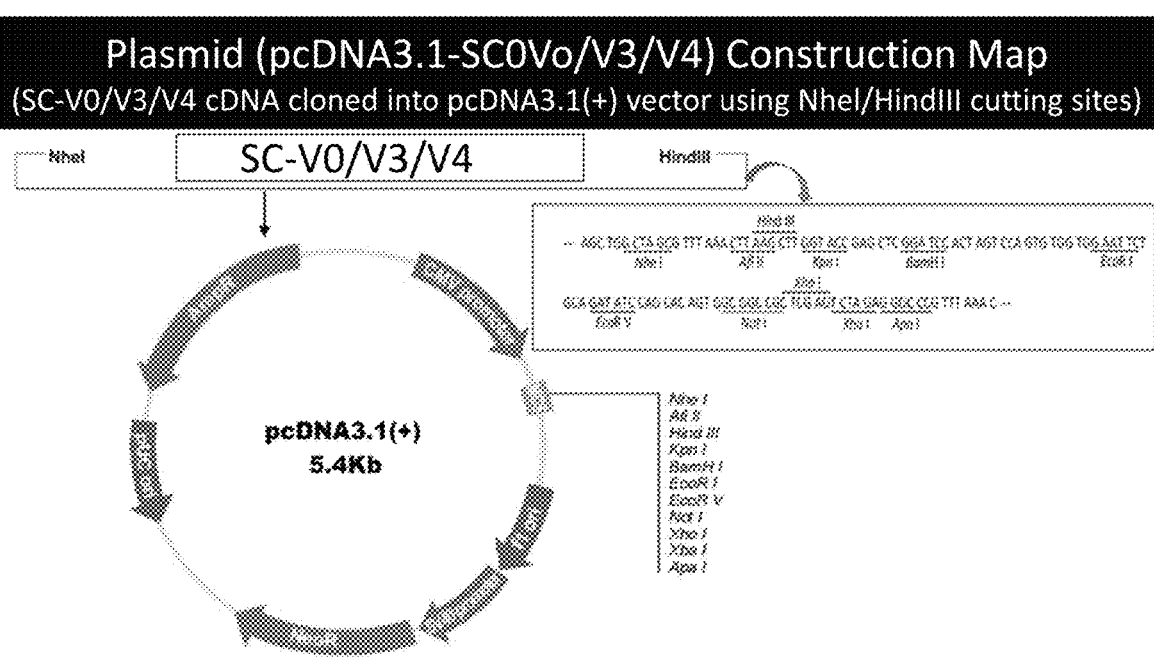

FIG. 11. Depicts examples of prepared plasmids for producing SC-V0-V3 and SC-V0/V3/V4 vaccines. The cDNAs of the SC-V0-V3 (A) or SC0V0/V3/V4 were synthesized and then subcloned into pcDNA3.1(+) vector to form expression plasmids suitable for preparation of the vaccines designed in mammalian cells and tissues and in vivo.

```
SEQUENCE LISTING
SEQ ID NO. 1:
MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA
```

-continued

ICHDQPELDSFKEELDKYFKNHTSPDVDLGDISGINASVV

NIQKEIDRLNEVAKNLNESLIDLQELGKYEQYIKWPWYIW

LGFIAGLIAIVMVTIMLCCMTSCCSCLKGCCSCGSCCKFD

EDDSEPVLKGVKLHYT

SEQ ID NO 2:
mysfvseetg tlivnsvllf lafvvfllvt lailtalrlc ayccnivnvs lvkpsfyvys rvknlnssrv pdllv SEQ ID NO 3:
madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq

SEQ ID NO 4: HAIMGVAFTW

SEQ ID NO 5: HAIMGVAFTWVMALACAAPPLV

SEQ ID NO 6:
MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

-continued

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDGKAHFPREGVFVSNGTHWFVTQRNFYEPQUITTDNT

FVSGNCDVVIGIVNNTVYDPLQPELDSFKEELDKYFKNHT

SPDVDLGDISGINASVVNIQKEIDRLNEVAKNLNESLIDL

QELGKYEQYIKWPWYIWLGFIAGLIAIVMVTIMLCCMTSC

CSCLKGCCSCGSCCKFDEDDSEPVLKGVKLHYT-P-HAIM

GVAFTW-P-mysfvseetg tlivnsvllf lafvvfllvt lailtalrlc ayccnivnvs lvkpsfyvys rvknlnssrv pdllv-P-HAIMGVAFTWVMALACAAPPLV-P-madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq

SEQ ID NO 7:
MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

-continued

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDQPELDSFKEELDKYFKNHTSPDVDLGDISGINASVV

NIQKEIDRLNEVAKNLNESLIDLQELGKYEQYIKWPWYIW

LGFIAGLIAIVMVTIMLCCMTSCCSCLKGCCSCGSCCKFD

EDDSEPVLKGVKLHYT-P-HAIMGVAFTW-P-mysfvseetg tlivnsvllf lafvvfllvt lailtalrlc ayccnivnvs lvkpsfyvys rvknlnssrv pdllv-P-

HAIMGVAFTW-P-madsngtitv eelkkllleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq

SEQ ID NO 8:
MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

-continued

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDGKAHFPREGVFVSNGTHWFVTQRNFYEPQUITTDNT

FVSGNCDVVIGIVNNTVYDPLQPELDSFKEELDKYFKNHT

SPDVDLGDISGINASVVNIQKEIDRLNEVAKNLNESLIDL

QELGKYEQYIKWPWYIWLGFIAGLIAIVMVTIMLCCMTSC

CSCLKGCCSCGSCCKFDEDDSEPVLKGVKLHYT-P-HAIM

GVAFTWVMALACAAPPLV-P-mysfvseetg tlivnsvllf lafvvfllvt lailtalrlc ayccnivnvs lvkpsfyvys rvknlnssrv pdllv-P-HAIMGVAFTW-P-madsngtitv eelkkllleqw nlvigflflt wicllqfaya nrnrflyiik liflwllwpv tlacfvlaav yrinwitggiaiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq

SEQ ID NO 9:
MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDGKAHFPREGVFVSNGTHWFVTQRNFYEPQUITTDNT

FVSGNCDVVIGIVNNTVYDPLQPELDSFKEELDKYFKNHT

SPDVDLGDISGINASVVNIQKEIDRLNEVAKNLNESLIDL

QELGKYEQYIKWPWYIWLGFIAGLIAIVMVTIMLCCMTSC

CSCLKGCCSCGSCCKFDEDDSEPVLKGVKLHYT-P HAIMG

VAFTWVMALACAAPPLV-P-mysfvseetg tlivnsvllf lafvvfllvt lailtalrlc ayccnivnvs lvkpsfyvys rvknlnssrv pdllv-P-HAIMGVAFTWVMALACAAPPLV-P- madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq SEQ ID NO 10:
madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq-P-HAIMGVAFTW-P-
mysfvseetg tlivnsvllf lafvvfllvt lailtalrlc ayccnivnvs lvkpsfyvys rvknlnssrv pdllv-P-HAIMGVAFTWVMALACAAPPLV

-P-MFVFLVLLPLVSSQCVNLTTRTQLPPAYTNSFTRGVY

YPDKVFRSSVLHSTQDLFLPFFSNVTWFHAIHVSGTNGTK

RFDNPVLPFNDGVYFASTEKSNIIRGWIFGTTLDSKTQSL

LIVNNATNVVIKVCEFQFCNDPFLGVYYHKNNKSWMESEF

RVYSSANNCTFEYVSQPFLMDLEGKQGNFKNLREFVFKNI

DGYFKIYSKHTPINLVRDLPQGFSALEPLVDLPIGINITR

FQTLLALHRSYLTPGDSSSGWTAGAAAYYVGYLQPRTFLL

KYNENGTITDAVDCALDPLSETKCTLKSFTVEKGIYQTSN

FRVQPTESIVRFPNITNLCPFGEVFNATRFASVYAWNRKR

ISNCVADYSVLYNSASFSTFKCYGVSPTKLNDLCFTNVYA

DSFVIRGDEVRQIAPGQTGKIADYNYKLPDDFTGCVIAWN

SNNLDSKVGGNYNYLYRLFRKSNLKPFERDISTEIYQAGS

TPCNGVEGFNCYFPLQSYGFQPTNGVGYQPYRVVVLSFEL

LHAPATVCGPKKSTNLVKNKCVNFNFNGLTGTGVLTESNK

KFLPFQQFGRDIADTTDAVRDPQTLEILDITPCSFGGVSV

ITPGTNTSNQVAVLYQDVNCTEVPVAIHADQLTPTWRVYS

TGSNVFQTRAGCLIGAEHVNNSYECDIPIGAGICASYQTQ

TNSPRRARSVASQSIIAYTMSLGAENSVAYSNNSIAIPTN

FTISVTTEILPVSMTKTSVDCTMYICGDSTECSNLLLQYG

SFCTQLNRALTGIAVEQDKNTQEVFAQVKQIYKTPPIKDF

GGFNFSQILPDPSKPSKRSFIEDLLFNKVTLADAGFIKQY

GDCLGDIAARDLICAQKFNGLTVLPPLLTDEMIAQYTSAL

LAGTITSGWTFGAGAALQIPFAMQMAYRFNGIGVTQNVLY

ENQKLIANQFNSAIGKIQDSLSSTASALGKLQDVVNQNAQ

ALNTLVKQLSSNFGAISSVLNDILSRLDKVEAEVQIDRLI

TGRLQSLQTYVTQQLIRAAEIRASANLAATKMSECVLGQS

KRVDFCGKGYHLMSFPQSAPHGVVFLHVTYVPAQEKNFTT

APAICHDGKAHFPREGVFVSNGTHWFVTQRNFYEPQIITT

DNTFVSGNCDVVIGIVNNTVYDPLQPELDSFKEELDKYFK

NHTSPDVDLGDISGINASVVNIQKEIDRLNEVAKNLNESL

IDLQELGKYEQYIKWPWYIWLGFIAGLIAIVMVTIMLCCM

TSCCSCLKGCCSCGSCCKFDEDDSEPVLKGVKLHYT

SEQ ID NO 11:
madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq-P-HAIMGVAFTW-P- mysfvseetg tlivnsvllf lafvvfllvt lailtalrlc ayccnivnvs lvkpsfyvys rvknlnssrv pdllv-P-

HAIMGVAFTW-P-

MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

VIRGDEVRQIAPGQTGKIADYNYKLPDDFTGCVIAWNSNN

-continued

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDGKAHFPREGVFVSNGTHWFVTQRNFYEPQUITTDNT

FVSGNCDVVIGIVNNTVYDPLQPELDSFKEELDKYFKNHT

SPDVDLGDISGINASVVNIQKEIDRLNEVAKNLNESLIDL

QELGKYEQYIKWPWYIWLGFIAGLIAIVMVTIMLCCMTSC

CSCLKGCCSCGSCCKFDEDDSEPVLKGVKLHYT

SEQ ID NO 12:
madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq P-HAIMGVAFTWVMALA CAAPPLV-P-mysfvseetg tlivnsvllf lafvvfllvt lailtalrlc ayccnivnvs lvkpsfyvys rvknlnssrv pdllv-P- HAIMGVAFTW-P-

MFVFLVLLPLVSSQCVNLTTRTQLPPAYTNSFTRGVYYPD

KVFRSSVLHSTQDLFLPFFSNVTWFHAIHVSGTNGTKRFD

NPVLPFNDGVYFASTEKSNIIRGWIFGTTLDSKTQSLLIV

NNATNVVIKVCEFQFCNDPFLGVYYHKNNKSWMESEFRVY

SSANNCTFEYVSQPFLMDLEGKQGNFKNLREFVFKNIDGY

FKIYSKHTPINLVRDLPQGFSALEPLVDLPIGINITRFQT

LLALHRSYLTPGDSSSGWTAGAAAYYVGYLQPRTFLLKYN

ENGTITDAVDCALDPLSETKCTLKSFTVEKGIYQTSNFRV

QPTESIVRFPNITNLCPFGEVFNATRFASVYAWNRKRISN

CVADYSVLYNSASFSTFKCYGVSPTKLNDLCFTNVYADSF

-continued

VIRGDEVRQIAPGQTGKIADYNYKLPDDFTGCVIAWNSNN

LDSKVGGNYNYLYRLFRKSNLKPFERDISTEIYQAGSTPC

NGVEGFNCYFPLQSYGFQPTNGVGYQPYRVVVLSFELLHA

PATVCGPKKSTNLVKNKCVNFNFNGLTGTGVLTESNKKFL

PFQQFGRDIADTTDAVRDPQTLEILDITPCSFGGVSVITP

GTNTSNQVAVLYQDVNCTEVPVAIHADQLTPTWRVYSTGS

NVFQTRAGCLIGAEHVNNSYECDIPIGAGICASYQTQTNS

PRRARSVASQSIIAYTMSLGAENSVAYSNNSIAIPTNFTI

SVTTEILPVSMTKTSVDCTMYICGDSTECSNLLLQYGSFC

TQLNRALTGIAVEQDKNTQEVFAQVKQIYKTPPIKDFGGF

NFSQILPDPSKPSKRSFIEDLLFNKVTLADAGFIKQYGDC

LGDIAARDLICAQKFNGLTVLPPLLTDEMIAQYTSALLAG

TITSGWTFGAGAALQIPFAMQMAYRFNGIGVTQNVLYENQ

KLIANQFNSAIGKIQDSLSSTASALGKLQDVVNQNAQALN

TLVKQLSSNFGAISSVLNDILSRLDKVEAEVQIDRLITGR

LQSLQTYVTQQLIRAAEIRASANLAATKMSECVLGQSKRV

DFCGKGYHLMSFPQSAPHGVVFLHVTYVPAQEKNFTTAPA

ICHDQPELDSFKEELDKYFKNHTSPDVDLGDISGINASVV

NIQKEIDRLNEVAKNLNESLIDLQELGKYEQYIKWPWYIW

LGFIAGLIAIVMVTIMLCCMTSCCSCLKGCCSCGSCCKFD

EDDSEPVLKGVKLHYT

SEQ ID NO 13:
madsngtitv eelkklleqw nlvigflflt wicllqfaya nrnrflyiik liflwllwpv tlacfvlaav yrinwitggi aiamaclvgl mwlsyfiasf rlfartrsmw sfnpetnill nvplhgtilt rplleselvi gavilrghlr iaghhlgrcd ikdlpkeitv atsrtlsyyk lgasqrvagd sgfaaysryr ignyklntdh ssssdniall vq-P

HAIMGVAFTWVMALACAAPPLV-P-mysfvseetg tlivnsvllf lafvvfllvt lailtalrlc ayccnivnvs lvkpsfyvys rvknlnssrv pdllv-P-

HAIMGVAFTWVMALACAAPPLV-P-MFVFLVLLPLVSS

QCVNLTTRTQLPPAYTNSFTRGVYYPDKVFRSSVLHSTQD

LFLPFFSNVTWFHAIHVSGTNGTKRFDNPVLPFNDGVYFA

STEKSNIIRGWIFGTTLDSKTQSLLIVNNATNVVIKVCEF

QFCNDPFLGVYYHKNNKSWMESEFRVYSSANNCTFEYVSQ

PFLMDLEGKQGNFKNLREFVFKNIDGYFKIYSKHTPINLV

RDLPQGFSALEPLVDLPIGINITRFQTLLALHRSYLTPGD

SSSGWTAGAAAYYVGYLQPRTFLLKYNENGTITDAVDCAL

DPLSETKCTLKSFTVEKGIYQTSNFRVQPTESIVRFPNIT

NLCPFGEVFNATRFASVYAWNRKRISNCVADYSVLYNSAS

-continued

FSTFKCYGVSPTKLNDLCFTNVYADSFVIRGDEVRQIAPG

QTGKIADYNYKLPDDFTGCVIAWNSNNLDSKVGGNYNYLY

RLFRKSNLKPFERDISTEIYQAGSTPCNGVEGFNCYFPLQ

SYGFQPTNGVGYQPYRVVVLSFELLHAPATVCGPKKSTNL

VKNKCVNFNFNGLTGTGVLTESNKKFLPFQQFGRDIADTT

DAVRDPQTLEILDITPCSFGGVSVITPGTNTSNQVAVLYQ

DVNCTEVPVAIHADQLTPTWRVYSTGSNVFQTRAGCLIGA

EHVNNSYECDIPIGAGICASYQTQTNSPRRARSVASQSII

AYTMSLGAENSVAYSNNSIAIPTNFTISVTTEILPVSMTK

TSVDCTMYICGDSTECSNLLLQYGSFCTQLNRALTGIAVE

QDKNTQEVFAQVKQIYKTPPIKDFGGFNFSQILPDPSKPS

KRSFIEDLLFNKVTLADAGFIKQYGDCLGDIAARDLICAQ

KFNGLTVLPPLLTDEMIAQYTSALLAGTITSGWTFGAGAA

LQIPFAMQMAYRFNGIGVTQNVLYENQKLIANQFNSAIGK

IQDSLSSTASALGKLQDVVNQNAQALNTLVKQLSSNFGAI

SSVLNDILSRLDKVEAEVQIDRLITGRLQSLQTYVTQQLI

RAAEIRASANLAATKMSECVLGQSKRVDFCGKGYHLMSFP

QSAPHGVVFLHVTYVPAQEKNFTTAPAICHDGKAHFPREG

VFVSNGTHWFVTQRNFYEPQUITTDNTFVSGNCDVVIGIV

NNTVYDPLQPELDSFKEELDKYFKNHTSPDVDLGDISGIN

-continued

ASVVNIQKEIDRLNEVAKNLNESLIDLQELGKYEQYIKWP

WYIWLGFIAGLIAIVMVTIMLCCMTSCCSCLKGCCSCGSC

CKFDEDDSEPVLKGVKLHYT

TABLE 1

Table 1. SC-viral membrane protein complex vs S-protein

| Vaccine Design | Blocking S-protein invasion | Blocking E-protein Ion Channel activity | Blocking M-protein function | Predicted immunogenicity |
|---|---|---|---|---|
| SC-complex | X | X | X | ++++ |
| S-protein | X | – | – | ++ |
| S-protein mRNA | X | – | – | ++ |
| S-protein cDNA | X | – | – | ++ |

TABLE 2

Comparison of the amino acid sequences of four SC-SEM membrane protein complexes of COVID-19 a). SC-SEM-1: N-terminus-S-protein-10aa-E-protein-22aa-M-protein-C-terminus
b). SC-SEM-2: N-terminus-S-protein-22aa-E-protein-22aa-M protein-C-terminus
c). Reversed sequence: SC-MES-1(R): N-Terminus-M-protein-22aa-E-protein-10aa-S-protein-C-terminus
d). Reversed sequence: SC-MES-2(R): N-Terminus-M-protein-22aa-E-22aa-S-protein-C-terminus

What is claimed:

1. A coronavirus single-chain (SC) membrane protein comprising a viral spike (S) protein, a viral envelope (E) protein, and a viral membrane (M) protein and, optionally, one or more linker sequences wherein:
 (i) the viral(S) protein comprises the amino acid sequence of SEQ ID NO: 1, or an amino acid sequence having at least 95% sequence identity to SEQ ID NO: 1;
 (ii) the viral (E) protein comprises the amino acid sequence of SEQ ID NO: 2, or an amino acid sequence having at least 95% sequence identity to SEQ ID NO: 2; and
 (iii) the viral (M) protein comprises the amino acid sequence of SEQ ID NO: 3, or a sequence having at least 95% sequence identity to SEQ ID NO: 3.

2. The coronavirus SC membrane protein of claim 1, comprising;
 (i) the amino acid sequence of SEQ ID NO: 6 or an amino acid sequence having at least 95%, sequence identity to SEQ ID NO: 6;
 (ii) the amino acid sequence of SEQ ID NO: 7 or an amino acid sequence having at least 95% sequence identity to SEQ ID NO: 7;
 (iii) the amino acid sequence of SEQ ID NO: 8 or an amino acid sequence having at least 95% sequence identity to SEQ ID NO: 8; or
 (iv) the amino acid sequence of SEQ ID NO: 9 or an amino acid sequence having at least 95% sequence identity to SEQ ID NO: 9.

3. The coronavirus SC membrane protein of claim 1, wherein the linker sequence is a polypeptide having 10-50 amino acids.

4. The coronavirus SC membrane protein of claim 3, wherein the linker sequence is selected from the group consisting of HAIMGVAFTW (SEQ ID NO: 4) and HAIMGVAFTWVMALACAAPPLV (SEQ ID NO:5).

5. A nucleic acid molecule encoding for the coronavirus SC membrane protein of claim 1.

6. A recombinant expression vector comprising the nucleic acid molecule of claim 5.

7. A pharmaceutical composition comprising (i) the coronavirus SC membrane protein of claim 1 and/or (ii) a nucleic acid encoding said coronavirus SC membrane protein; and a pharmaceutical acceptable carrier.

8. A diagnostic method of detecting a coronavirus-specific antibody in a sample through immunoassays, said method comprising contacting a sample with the coronavirus SC membrane protein of claim 1 for detecting a coronavirus-specific antibody.

9. A method of treating or preventing coronavirus infection in a subject in need thereof comprising administering the coronavirus SC membrane protein of claim 1 to the subject in need thereof.

10. The method of claim 9, wherein the coronavirus infection is caused by SARS-COV-2 or a variant thereof.

11. A method of treating or preventing coronavirus infection in a subject in need thereof comprising administering the nucleic acid molecule of claim 5 to the subject in need thereof.

12. The nucleic acid molecule of claim 5 wherein the nucleic acid molecule is an RNA used for vaccination.

13. A vaccine composition comprising:
 (i) the coronavirus SC membrane protein of claim 1; and/or
 (ii) a nucleic acid molecule of claim 5;
 and an adjuvant.

14. The vaccine composition of claim 13, wherein the vaccine is a nanoparticle-based vaccine.

15. A vaccine composition compromising nanoliposomes encapsulated with the nucleic acid molecule of claim 5.

16. A method for immunizing a subject comprising administering to the subject the vaccine composition of claim 13.

17. A method of treating or preventing clinical signs caused by coronavirus infection in a subject in need thereof, the method comprising administering to the subject a therapeutically effective amount of the vaccine composition of claim 13.

18. A vaccination kit comprising the vaccine composition of claim 13.

19. A diagnostic method for detecting a coronavirus-specific antibody in a sample derived from a test subject comprising (i) contacting the coronavirus SC membrane protein of claim 1 with the test sample and (ii) detecting the presence of a coronavirus SC membrane protein/antibody complex.

20. A diagnostic kit for performing the diagnostic method of claim 19, wherein the diagnostic kit comprises the coronavirus SC membrane protein of claim 1.

21. A nanoparticle comprising the coronavirus SC membrane protein of claim 1 and/or the nucleic acid molecule of claim 5.

* * * * *